(12) United States Patent
Braido et al.

(10) Patent No.: US 9,737,264 B2
(45) Date of Patent: Aug. 22, 2017

(54) SENSORS FOR PROSTHETIC HEART DEVICES

(71) Applicant: St. Jude Medical, Cardiology Division, Inc., St. Paul, MN (US)

(72) Inventors: Peter N. Braido, Wyoming, MN (US); Chad Joshua Green, Forest Lake, MN (US); Neelakantan Saikrishnan, Plymouth, MN (US); Mina S. Fahim, Shoreview, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 36 days.

(21) Appl. No.: 14/825,579

(22) Filed: Aug. 13, 2015

(65) Prior Publication Data

US 2016/0045312 A1    Feb. 18, 2016

Related U.S. Application Data

(60) Provisional application No. 62/038,512, filed on Aug. 18, 2014.

(51) Int. Cl.
*A61F 2/24* (2006.01)
*A61B 5/00* (2006.01)
(Continued)

(52) U.S. Cl.
CPC ............ *A61B 5/6862* (2013.01); *A61B 5/026* (2013.01); *A61B 5/0215* (2013.01);
(Continued)

(58) Field of Classification Search
None
See application file for complete search history.

(56) References Cited

U.S. PATENT DOCUMENTS

| 4,275,469 A | 6/1981 | Gabbay |
| 4,491,986 A | 1/1985 | Gabbay |

(Continued)

FOREIGN PATENT DOCUMENTS

| DE | 19857887 B4 | 5/2005 |
| DE | 10121210 B4 | 11/2005 |

(Continued)

OTHER PUBLICATIONS

International Search Report and Written Opinion for Application No. PCT/US2015/044969 dated Dec. 11, 2015.
(Continued)

*Primary Examiner* — Thomas J Sweet
*Assistant Examiner* — Megan Wolf
(74) *Attorney, Agent, or Firm* — Lerner, David, Littenberg, Krumholz & Mentlik, LLP

(57) ABSTRACT

An implantable device system includes an implantable device, such as an annuloplasty ring, for controlling at least a shape and/or size of a heart valve annulus. The implantable device includes an arcuate body and an adjustment system configured to adjust the shape and/or size of the arcuate body. An adjustment tool is configured to be coupled to the adjustment system so that the adjustment tool can be used to activate and control adjustment of the arcuate body. A sensor system is configured to be coupled to the implantable device. The sensor system includes a first sensor configured to measure physiological data at an inflow portion of the valve annulus when the implantable device is implanted into the valve annulus, and a second sensor configured to measure physiological data at an outflow portion of the valve annulus when the implantable device is implanted into the valve annulus.

13 Claims, 36 Drawing Sheets

(51) Int. Cl.
*A61F 2/844* (2013.01)
*A61B 5/0215* (2006.01)
*A61B 5/02* (2006.01)
*A61B 5/026* (2006.01)
*A61B 17/00* (2006.01)
*A61B 17/12* (2006.01)

(52) U.S. Cl.
CPC ...... *A61B 5/02028* (2013.01); *A61B 5/02158* (2013.01); *A61B 5/6847* (2013.01); *A61B 17/0057* (2013.01); *A61B 17/12122* (2013.01); *A61F 2/2412* (2013.01); *A61F 2/2418* (2013.01); *A61F 2/2445* (2013.01); *A61F 2/2448* (2013.01); *A61F 2/2472* (2013.01); *A61F 2/844* (2013.01); *A61B 2017/00022* (2013.01); *A61B 2017/00575* (2013.01); *A61B 2017/00632* (2013.01); *A61B 2562/0247* (2013.01); *A61F 2210/0066* (2013.01); *A61F 2220/0016* (2013.01); *A61F 2220/0075* (2013.01); *A61F 2230/0008* (2013.01); *A61F 2230/0034* (2013.01); *A61F 2230/0065* (2013.01); *A61F 2250/001* (2013.01); *A61F 2250/0002* (2013.01); *A61F 2250/0004* (2013.01); *A61F 2250/0063* (2013.01); *A61F 2250/0065* (2013.01)

(56) References Cited

U.S. PATENT DOCUMENTS

| | | | |
|---|---|---|---|
| 4,759,758 | A | 7/1988 | Gabbay |
| 4,878,906 | A | 11/1989 | Lindemann et al. |
| 4,922,905 | A | 5/1990 | Strecker |
| 4,994,077 | A | 2/1991 | Dobben |
| 5,411,552 | A | 5/1995 | Andersen et al. |
| 5,480,423 | A | 1/1996 | Ravenscroft et al. |
| 5,487,760 | A | 1/1996 | Villafana |
| 5,847,760 | A | 12/1998 | Elmaliach et al. |
| 5,855,601 | A | 1/1999 | Bessler et al. |
| 5,935,163 | A | 8/1999 | Gabbay |
| 5,961,549 | A | 10/1999 | Nguyen et al. |
| 6,083,257 | A | 7/2000 | Taylor et al. |
| 6,090,140 | A | 7/2000 | Gabbay |
| 6,214,036 | B1 | 4/2001 | Letendre et al. |
| 6,264,691 | B1 | 7/2001 | Gabbay |
| 6,267,783 | B1 | 7/2001 | Letendre et al. |
| 6,287,339 | B1 * | 9/2001 | Vazquez ............ A61F 2/2403 623/2.11 |
| 6,331,163 | B1 | 12/2001 | Kaplan |
| 6,368,348 | B1 | 4/2002 | Gabbay |
| 6,419,695 | B1 | 7/2002 | Gabbay |
| 6,468,660 | B2 | 10/2002 | Ogle et al. |
| 6,488,702 | B1 | 12/2002 | Besselink |
| 6,517,576 | B2 | 2/2003 | Gabbay |
| 6,533,810 | B2 | 3/2003 | Hankh et al. |
| 6,582,464 | B2 | 6/2003 | Gabbay |
| 6,610,088 | B1 | 8/2003 | Gabbay |
| 6,685,625 | B2 | 2/2004 | Gabbay |
| 6,719,789 | B2 | 4/2004 | Cox |
| 6,730,118 | B2 | 5/2004 | Spenser et al. |
| 6,783,556 | B1 | 8/2004 | Gabbay |
| 6,790,230 | B2 | 9/2004 | Beyersdorf et al. |
| 6,869,444 | B2 | 3/2005 | Gabbay |
| 6,893,460 | B2 | 5/2005 | Spenser et al. |
| 6,908,481 | B2 | 6/2005 | Cribier |
| 7,025,780 | B2 | 4/2006 | Gabbay |
| 7,137,184 | B2 | 11/2006 | Schreck |
| 7,160,322 | B2 | 1/2007 | Gabbay |
| 7,247,167 | B2 | 7/2007 | Gabbay |
| 7,267,686 | B2 | 9/2007 | DiMatteo et al. |
| 7,374,573 | B2 | 5/2008 | Gabbay |
| 7,381,218 | B2 | 6/2008 | Schreck |
| 7,452,371 | B2 | 11/2008 | Pavcnik et al. |
| 7,524,331 | B2 | 4/2009 | Birdsall |
| RE40,816 | E | 6/2009 | Taylor et al. |
| 7,585,321 | B2 | 9/2009 | Cribier |
| 7,731,742 | B2 | 6/2010 | Schlick et al. |
| 7,846,203 | B2 | 12/2010 | Cribier |
| 7,846,204 | B2 | 12/2010 | Letac et al. |
| 7,909,770 | B2 | 3/2011 | Stern et al. |
| 7,914,569 | B2 | 3/2011 | Nguyen et al. |
| D648,854 | S | 11/2011 | Braido |
| D652,926 | S | 1/2012 | Braido |
| D652,927 | S | 1/2012 | Braido et al. |
| D653,341 | S | 1/2012 | Braido et al. |
| D653,342 | S | 1/2012 | Braido et al. |
| D653,343 | S | 1/2012 | Ness et al. |
| D654,169 | S | 2/2012 | Braido |
| D654,170 | S | 2/2012 | Braido et al. |
| D660,432 | S | 5/2012 | Braido |
| D660,433 | S | 5/2012 | Braido et al. |
| D660,967 | S | 5/2012 | Braido et al. |
| 2002/0036220 | A1 | 3/2002 | Gabbay |
| 2003/0023303 | A1 | 1/2003 | Palmaz et al. |
| 2003/0130726 | A1 | 7/2003 | Thorpe et al. |
| 2004/0049262 | A1 | 3/2004 | Obermiller et al. |
| 2004/0093075 | A1 | 5/2004 | Kuehne |
| 2005/0060030 | A1 * | 3/2005 | Lashinski ............ A61B 5/6882 623/2.37 |
| 2005/0096726 | A1 | 5/2005 | Sequin et al. |
| 2005/0154321 | A1 | 7/2005 | Wolinsky et al. |
| 2005/0165317 | A1 | 7/2005 | Turner et al. |
| 2005/0256566 | A1 | 11/2005 | Gabbay |
| 2006/0008497 | A1 | 1/2006 | Gabbay |
| 2006/0122692 | A1 | 6/2006 | Gilad et al. |
| 2006/0149360 | A1 | 7/2006 | Schwammenthal et al. |
| 2006/0173532 | A1 | 8/2006 | Flagle et al. |
| 2006/0178740 | A1 | 8/2006 | Stacchino et al. |
| 2006/0206202 | A1 | 9/2006 | Bonhoeffer et al. |
| 2006/0241744 | A1 | 10/2006 | Beith |
| 2006/0241745 | A1 | 10/2006 | Solem |
| 2006/0259137 | A1 | 11/2006 | Artof et al. |
| 2006/0265056 | A1 | 11/2006 | Nguyen et al. |
| 2006/0276813 | A1 | 12/2006 | Greenberg |
| 2007/0067027 | A1 * | 3/2007 | Moaddeb ............ A61F 2/2448 623/2.11 |
| 2007/0067029 | A1 | 3/2007 | Gabbay |
| 2007/0093890 | A1 | 4/2007 | Eliasen et al. |
| 2007/0100435 | A1 | 5/2007 | Case et al. |
| 2007/0118210 | A1 | 5/2007 | Pinchuk |
| 2007/0129637 | A1 | 6/2007 | Wolinsky et al. |
| 2007/0213813 | A1 | 9/2007 | Von Segesser et al. |
| 2007/0233228 | A1 | 10/2007 | Eberhardt et al. |
| 2007/0244545 | A1 | 10/2007 | Birdsall et al. |
| 2007/0288087 | A1 | 12/2007 | Fearnot et al. |
| 2008/0021552 | A1 | 1/2008 | Gabbay |
| 2008/0027483 | A1 * | 1/2008 | Cartledge ............ A61B 5/061 606/201 |
| 2008/0039934 | A1 | 2/2008 | Styrc |
| 2008/0051838 | A1 * | 2/2008 | Shuros ............ A61F 2/2403 607/2 |
| 2008/0082164 | A1 | 4/2008 | Friedman |
| 2008/0097595 | A1 | 4/2008 | Gabbay |
| 2008/0114452 | A1 | 5/2008 | Gabbay |
| 2008/0125853 | A1 | 5/2008 | Bailey et al. |
| 2008/0140189 | A1 | 6/2008 | Nguyen et al. |
| 2008/0147183 | A1 | 6/2008 | Styrc |
| 2008/0154355 | A1 | 6/2008 | Benichou et al. |
| 2008/0154356 | A1 | 6/2008 | Obermiller et al. |
| 2008/0243245 | A1 | 10/2008 | Thambar et al. |
| 2008/0255662 | A1 | 10/2008 | Stacchino et al. |
| 2008/0262602 | A1 | 10/2008 | Wilk et al. |
| 2008/0269879 | A1 | 10/2008 | Sathe et al. |
| 2009/0112309 | A1 | 4/2009 | Jaramillo et al. |
| 2009/0138079 | A1 | 5/2009 | Tuval et al. |
| 2009/0234404 | A1 * | 9/2009 | Fitzgerald ............ A61N 1/36514 607/9 |
| 2010/0036484 | A1 | 2/2010 | Hariton et al. |
| 2010/0049306 | A1 | 2/2010 | House et al. |
| 2010/0087907 | A1 | 4/2010 | Lattouf |
| 2010/0131055 | A1 | 5/2010 | Case et al. |
| 2010/0168778 | A1 | 7/2010 | Braido |

(56) References Cited

U.S. PATENT DOCUMENTS

| | | |
|---|---|---|
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2011/0029072 A1 | 2/2011 | Gabbay |
| 2013/0006352 A1* | 1/2013 | Yaron .................. A61F 2/2445 623/2.37 |
| 2016/0045316 A1 | 2/2016 | Braido et al. |
| 2016/0256274 A1* | 9/2016 | Hayoz .................. A61F 2/2445 |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1050265 A2 | 11/2000 |
| EP | 1584306 A1 | 10/2005 |
| EP | 1598031 A2 | 11/2005 |
| EP | 1360942 B1 | 12/2005 |
| FR | 2850008 A1 | 7/2004 |
| FR | 2847800 B1 | 10/2005 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 03103539 A1 | 12/2003 |
| WO | 2005055883 A1 | 6/2005 |
| WO | 2006073626 A2 | 7/2006 |
| WO | 2008006003 A2 | 1/2008 |
| WO | 2008024180 A1 | 2/2008 |
| WO | 2008071817 A1 | 6/2008 |
| WO | 2009006602 A1 | 1/2009 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |
| WO | 2012106344 A1 | 8/2012 |
| WO | 2015058808 A1 | 4/2015 |

OTHER PUBLICATIONS

International Search Report and Written Opinion for Application No. PCT/US2015/044962 dated Oct. 30, 2015.

Catheter-implanted prosthetic heart valves, Knudsen, L.L., et al., The International Journal of Artificial Organs, vol. 16, No. 5 1993, pp. 253-262.

Transluminal Aortic Valve Placement, Moazami, Nader, et al., ASAIO Journal, 1996; 42:M381-M385.

Transluminal Catheter Implanted Prosthetic Heart Valves, Andersen, Henning Rud, International Journal of Angiology 7:102-106 (1998).

Transluminal implantation of artificial heart valves, Andersen, H. R., et al., European Heart Journal (1992) 13, 704-708.

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

* cited by examiner

SENSORS FOR PROSTHETIC HEART DEVICES

CROSS-REFERENCE TO RELATED APPLICATIONS

The present application claims the benefit of the filing date of U.S. Provisional Patent Application No. 62/038,512, titled "Prosthetic Heart Devices Having Diagnostic Capabilities," filed Aug. 18, 2014, the disclosure of which is hereby incorporated by reference herein

BACKGROUND

The present disclosure relates to heart valve replacement and repair devices such as annuloplasty rings. More particularly, the present disclosure relates to devices and methods for using annuloplasty rings having diagnostic capabilities.

Many anatomic structures in the mammalian body are hollow passages in which walls of tissue define an orifice, which serves as a conduit for blood, other physiologic fluids, nutrient matter, or waste matter passing within the structure. In many physiologic settings, dysfunction may result from a structural orifice which is too large, too small or misshapen. In some cases, dysfunction can be relieved by interventional changes in the orifice size or shape.

Thus in surgery, there is often a desire to reduce or reshape the internal circumference of an orifice or other open anatomic structure to reconfigure the orifice or opening to achieve a desired physiologic effect. Such surgical procedures may require interruption in the normal physiologic flow of blood, other physiologic fluids, or other structural contents through the orifice or structure. The exact amount of the narrowing or reshaping that would result in the desired effect may not be fully appreciated until physiologic flow through the orifice or structure is resumed.

One example of a dysfunction within an anatomic orifice is in the area of cardiac surgery, and specifically valvular repair. Mitral valve disease can be subdivided into intrinsic valve disturbances and pathology extrinsic to the mitral valve ultimately affecting valvular function. Although these subdivisions exist, many of the repair techniques and overall operative approaches are similar in the various pathologies that exist. These dysfunctions may lead to leaflets of the mitral valve failing to coapt correctly, reducing the effectiveness of the mitral valve in acting as a one-way valve. For example, chordae rupture is a common cause of mitral insufficiency, resulting in a focal area of regurgitation. Mitral valve prolapse is a fairly common condition that leads over time to valvular insufficiency. Papillary muscle dysfunction, whether due to infarction or ischemia from coronary artery disease, often leads to mitral insufficiency (commonly referred to as ischemic mitral insufficiency). In addition, in patients with dilated cardiomyopathy the etiology of mitral insufficiency is the lack of coaptation of the valve leaflets from a dilated ventricle, resulting in regurgitation.

Two goals of mitral valve repair may include fixing primary valvular pathology (if present) and supporting or reshaping the valve annulus or reducing the annular dimension using a prosthesis, which may be in the form of a ring or band. One problem encountered in mitral valve repair is the surgeon's inability to fully assess the effectiveness of the repair until the heart has been fully closed, and the patient is weaned off cardiopulmonary bypass. Once this has been achieved, valvular function can be assessed in the operating room using transesophageal echocardiography ("TEE"). If significant residual valvular insufficiency is then documented, the surgeon may need to re-arrest the heart, re-open the heart, and then re-repair or replace the valve. This increases overall operative, anesthesia, and bypass times, and therefore increases the overall operative risks. In addition, even after the surgical procedure has been completed, anatomic structures may change over time or prostheses used to narrow the orifice may become less effective days, months, or years after the procedure. As the effectiveness of the prosthesis declines, physiological problems, such as some amount of regurgitation through the valve, may begin to occur again.

BRIEF SUMMARY

According to one aspect of the disclosure, an implantable device system includes an implantable device and a sensor system. The implantable device may be configured to control at least one of a shape and a size of a heart valve annulus, and include an arcuate body. The sensor system may be configured to be coupled to the implantable device, and may include one, two, or more sensors. When using two sensors, the first sensor may be configured to measure physiological data at an inflow portion of the valve annulus when the implantable device is implanted into the valve annulus. The second sensor may be configured to measure physiological data at an outflow portion of the valve annulus when the implantable device is implanted into the valve annulus.

According to another aspect of the disclosure, a method of performing a first surgical procedure in a patient includes forming an incision in a heart of the patient. A device may be implanted into a heart valve annulus of the patient, the device configured to control at least one of a shape and size of the heart valve annulus and including an arcuate body. A sensor system may be coupled to the device, the sensor system including one, two, or more sensors. When the sensor system includes two sensors, a first sensor may be positioned in an inflow portion of the heart valve annulus and a second sensor may be positioned in an outflow portion of the heart valve annulus. A first set of physiological data may be measured across the heart valve annulus using the sensor system. A first amount of regurgitation across the heart valve annulus may be determined from the first set of physiological data a first amount of regurgitation across the heart valve annulus.

BRIEF DESCRIPTION OF THE DRAWINGS

FIG. 17 shows the implant in the folded position, and FIG. 18 shows the implant in the unfolded position.

DETAILED DESCRIPTION

As used herein, the term "inflow end," when used in connection with a prosthetic device implanted in the heart, refers to the end of the device closest to the point where antegrade blood flow initially begins to pass through the device, whereas the term "outflow end" refers to the end of the device closest to the point where antegrade blood flow finishes passing through the device.

Figure 1:
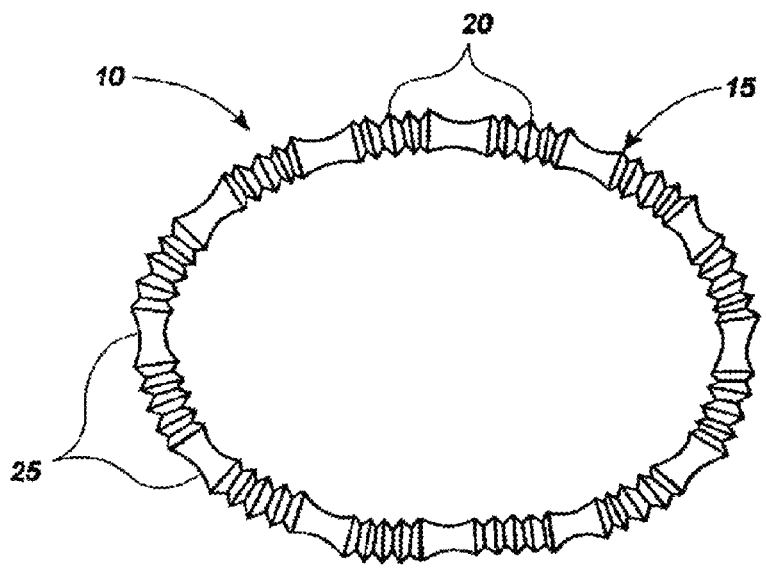
FIG. 1 is a front view of a first embodiment of an implant for reducing or reshaping the circumference of an anatomic orifice.

Referring now to the drawings, in which like numerals indicate like elements throughout the several views, an exemplary implant 10 comprising an implant body 15 is shown in FIG. 1. The implant body 15 may be provided in a shape and size determined by the anatomic needs of an intended native recipient anatomic site within a mammalian patient. Such a native recipient anatomic site may be, by way of illustration and not by way of limitation, a heart valve. Although the following disclosure generally focuses on mitral valve applications, it should be understood that the disclosure herein may apply equally to other heart valves, including the aortic valve, and other orifices in the body that may benefit from reshaping.

Figure 2:
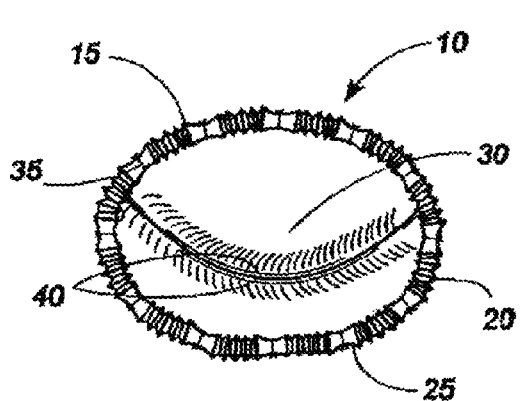
FIG. 2 is a front view of the implant of FIG. 1 secured to the annulus of a mitral valve, with the implant in an expanded position.
Figure 3:
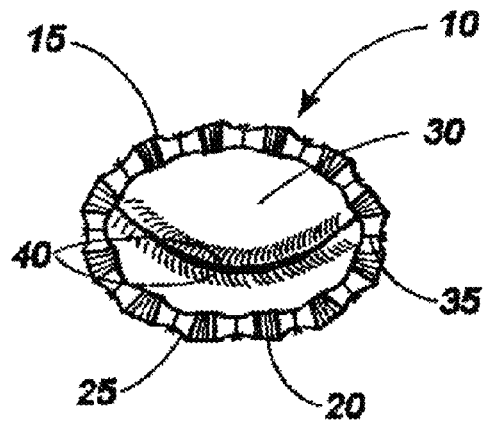
FIG. 3 is a front view of the implant of FIG. 1 secured to the annulus of a mitral valve, with the implant in a contracted position to reduce the size of the heart valve opening.

Implant 10 of FIG. 1 includes a generally circular implant body 15 which is provided with adjustable corrugated sections 20 alternating with intervening grommet-like attachment means 25 having narrowed intermediate neck portions. As can be seen in FIGS. 2 and 3, the implant body 15 may be secured to the annulus of a heart valve 30 by a fixation means such as a suture 35 secured over or through the attachment means 25. The corrugated sections 20 fold and unfold as the circumference of the implant body 15 shortens or lengthens. Adjustment of the implant 10 in situ may decrease the overall size of the heart valve 30, increasing the coaptation of the valve leaflets 40, and changing the configuration from that shown in FIG. 2 to that shown in FIG. 3.

Figure 4:
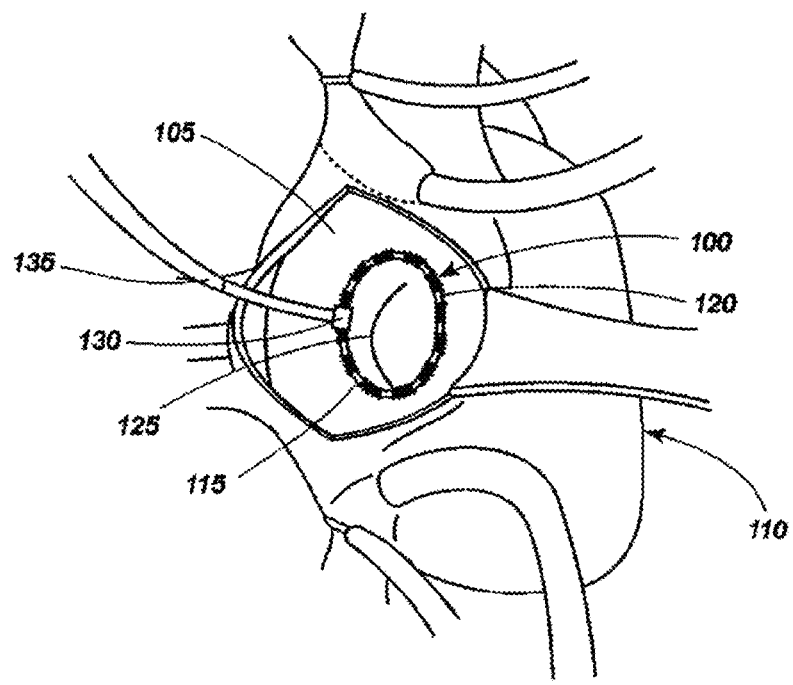
FIG. 4 is a schematic perspective view of a second embodiment of an implant for reducing or reshaping the circumference of an anatomic orifice, inserted through an open operative cardiac incision and secured around the mitral valve.
Figure 5:
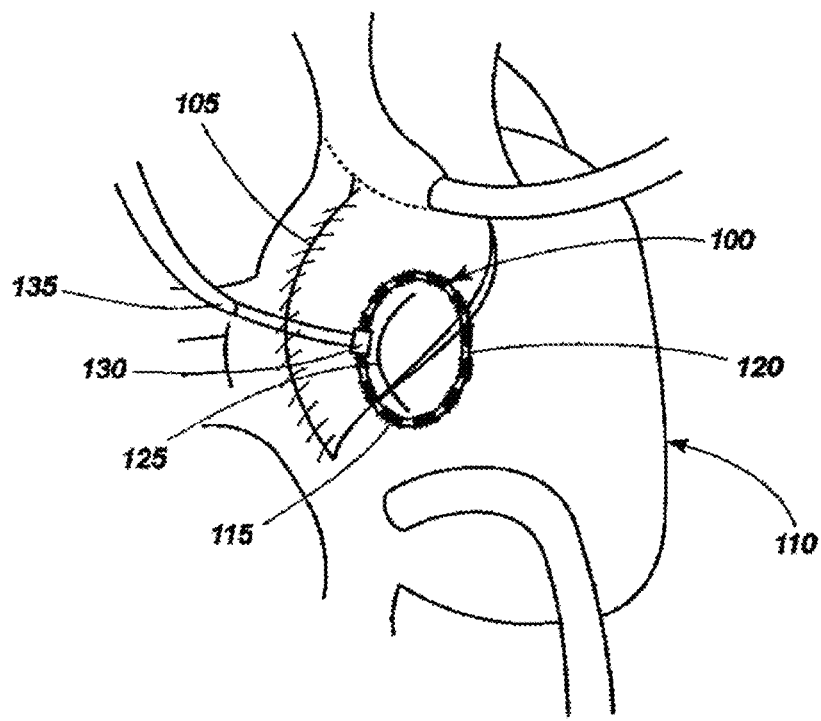
FIG. 5 is a schematic perspective view of the implant of FIG. 4, showing the cardiac incision closed, an adjustment tool extending through the closed incision, and adjustment of the implant possible after the patient has been taken "off pump."

An additional exemplary embodiment of an implant 100 according to the disclosure is shown in FIGS. 4 and 5, with an open operative cardiac incision 105 in a heart 110 shown in FIG. 4, and closure of the cardiac incision 105 in FIG. 5. As shown in FIG. 4, implant 100 comprises an implant body 115 with attachment means 120 that allows fixation to the annulus of a mitral valve 125. Implant 100 is further provided with an adjustment means 130 that is controlled by an attached or coupled adjustment tool 135. After closure of the myocardial incision 105 in FIG. 5, the adjustment tool 135 remains attached or coupled to the adjustment means 130, so that the size and shape of implant 100 may further be affected after physiologic flow through the heart 110 is resumed, but with the chest incision still open. Once the desired shape and function are achieved, the adjustment tool 135 may be disengaged from the adjustment means 130 and withdrawn from the myocardial incision 105. In various embodiments according to the present disclosure, the adjustment means 130 may be configured and placed to allow retention by or re-introduction of the adjustment tool 135 for adjustment following closure of the chest incision.

To use the implant 100 of FIGS. 4 and 5, the physician makes the open operative incision 105 in the heart 110, as shown in FIG. 4. The implant 100, mounted at the forward end of adjustment tool 135, is then advanced through the incision 105 and sutured to the annulus of the mitral valve 125. The adjustment tool 135 is then manipulated, e.g., rotated, depending upon the design of the adjustment means 130, to cause the adjustment means to reduce the size of the implant body 115, and hence the underlying mitral valve 125 to which it is sutured, to an approximate size. The myocardial incision 105 is then closed, as shown in FIG. 5, leaving the adjustment tool extending through the incision for post-operative adjustment.

Once the patient has been taken "off pump" and normal flow of blood through the heart 110 has resumed, but before the chest incision has been closed, further adjustments to the size of the mitral valve 125 can be made by manipulating the adjustment tool 135.

Figure 6:
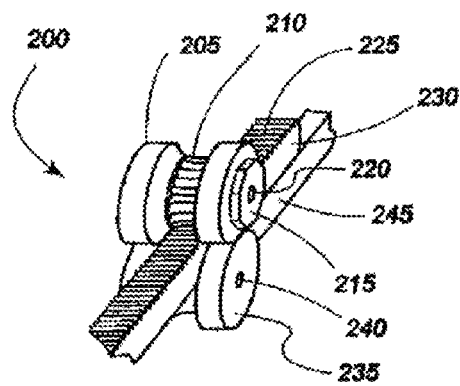
FIG. 6 is a perspective view of a first embodiment of an adjustment means for adjusting the circumference of an implant for reducing or reshaping the circumference of an anatomic orifice.
Figure 7:
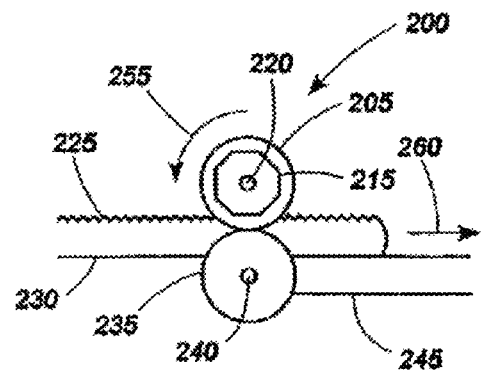
FIG. 7 is a right side view of the adjustment means of FIG. 6.
Figure 8:
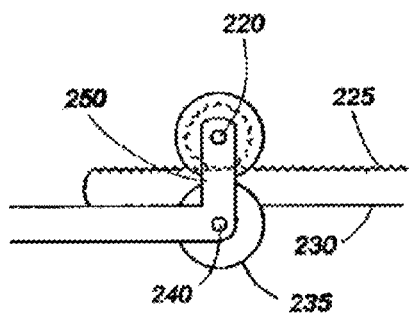
FIG. 8 is a left side view of the adjustment means of FIG. 6.

FIGS. 6-8 show an exemplary adjustment means 200 for adjusting the circumference of an annular implant such as the implant 100 previously described. The adjustment means 200 comprises a rack and pinion system in which a first cam 205 with geared teeth 210 and an engagement coupler 215 turns on a first axle 220. In this example, the first cam 205 engages a geared rack 225 on one or more surfaces of a first band 230. The first band 230 passes between the first cam 205 and a second cam 235 that turns on a second axle 240 that is joined to a second band 245. As shown in FIG. 8, the first and second axles 220, 240 are maintained in suitable spaced-apart relation by means of a bracket 250 formed at the end of the second band 245.

The adjustment means 200 may be set within a hollow annular implant 100 of the type previously described, though it is possible to use the adjustment means in a stand-alone configuration wherein the first and second bands 230, 245 are opposing ends of the same continuous annular structure. In either event, to adjust the length of an implant comprising the adjustment means 200, a tool such as a hex wrench engages the engagement coupler 215 on the first cam 205 and rotates the first cam in a counterclockwise direction as shown in FIG. 7, as indicated by the arrow 255. Rotation of the first cam 205 causes the teeth 210 to drive the rack 225 to move the first band 230 toward the right, as indicated by the arrow 260 in FIG. 7. This movement of the first band tightens the circumference of the annular implant. If the physician inadvertently adjusts the implant too tightly, reversing direction of the engagement coupler 215 will loosen the implant.

In embodiments according to the present disclosure, the first and second bands 230, 245 may be separate structures, or they may be opposing ends of the same continuous structure. In such an embodiment, when motion is imparted to the engagement coupler 215, the first cam 205 is rotated, causing the geared teeth 210 to engage the geared rack 225, and causing the first band 230 to move with respect to the second band 245 to adjust the circumference of an implant.

Figure 9:
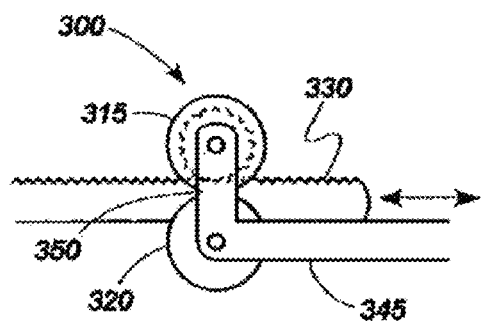
FIG. 9 is a right side view of a second embodiment of an adjustment means for adjusting the circumference of an implant for reducing or reshaping the circumference of an anatomic orifice.

FIG. 9 shows a somewhat different configuration of an exemplary adjustment means 300 according to the present disclosure, in which there is no engagement coupler, and a bracket 350 is provided on both sides of the cams to maintain the first cam 315 and the second cam 320 in close approximation. In one embodiment, the bracket is designed with close tolerances so as to press the first band 330 closely against the second band 345, thereby to hold the bands in fixed relative position by friction. In another embodiment, the brackets 350 are fabricated from an elastic material such that the cams 315, 320 can be spread apart to insert the first band 330 between the cams, whereupon the cams are pulled back together with sufficient force to hold the bands 330, 345 in fixed relative position by friction. In still another embodiment involving an elastic mounting arrangement between the cams 315, 320, the lower edge of the first band 330 and the upper edge of the second band 345 have mating frictional or mechanical surfaces, whereby the cams 315, 320 can be spread apart to permit relative movement between the bands or released to clamp the bands together in fixed relation.

Figure 10:
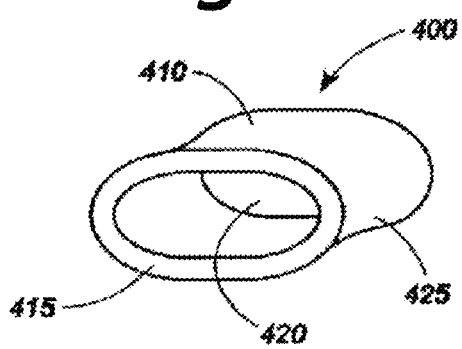
FIG. 10 is a perspective view of an embodiment of an attachment means for the implant of FIG. 1.

FIG. 10 shows an exemplary attachment means 400 for an implant according to the present disclosure. The attachment means 400 could be used, for example, in place of the attachment means 25 of the implant 10. The attachment means 400 takes the form of a grommet 410 comprising a wall 415 defining a lumen 420 and an attachment surface 425. Such an attachment means could be used with the implant body extending through the lumen 420 and with fixation devices such as sutures or wires either tied over or affixed through the attachment surface 425.

Figure 11:
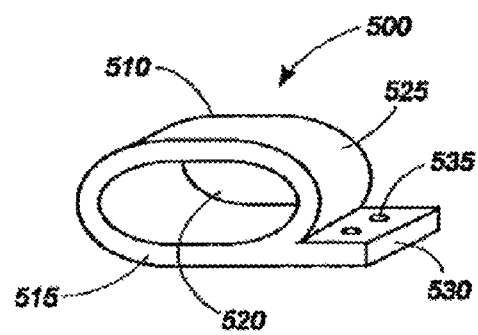
FIG. 11 is a perspective view of another embodiment of an attachment means for the implant of FIG. 1.

FIG. 11 shows another embodiment of an attachment means 500 for an implant according to the present disclosure. The attachment means 500 could also be used for example, in place of the attachment means 25 of the implant 10. FIG. 11 shows attachment means 500 in the form of a hollow tube or tube segment 510 comprising a wall 515 defining a lumen 520, an outer surface 525, and an attachment tab 530. Such an attachment means would be used with the implant body extending through the lumen 520 and with fixation devices such as sutures or wires either tied or otherwise affixed over or through the attachment tab 530. Such fixation devices might be placed through holes 535 provided in the attachment tab 530. Alternatively, a solid attachment tab 530 might be provided, and the fixation devices might be passed through the solid tab. Modifications of these attachment means may be used in conjunction with a sutureless attachment system.

Figure 12:
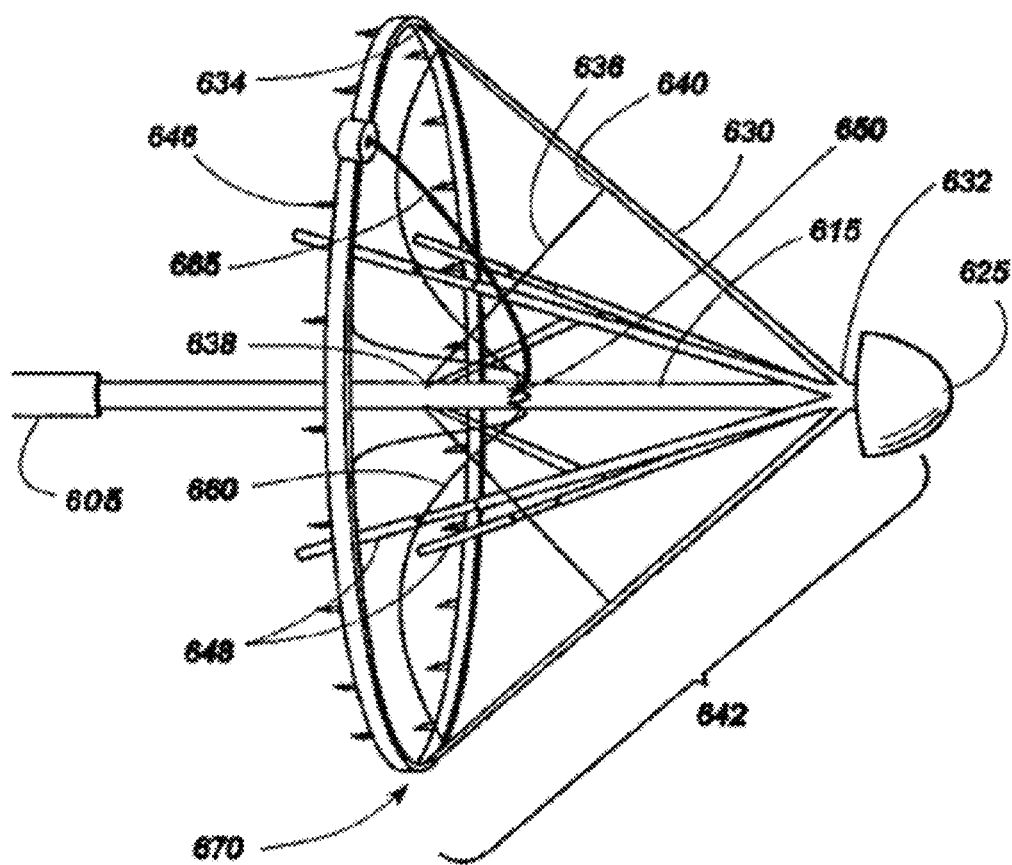
FIG. 12 is a perspective view of a third embodiment of an implant for reducing or reshaping the circumference of an anatomic orifice.
Figure 13:
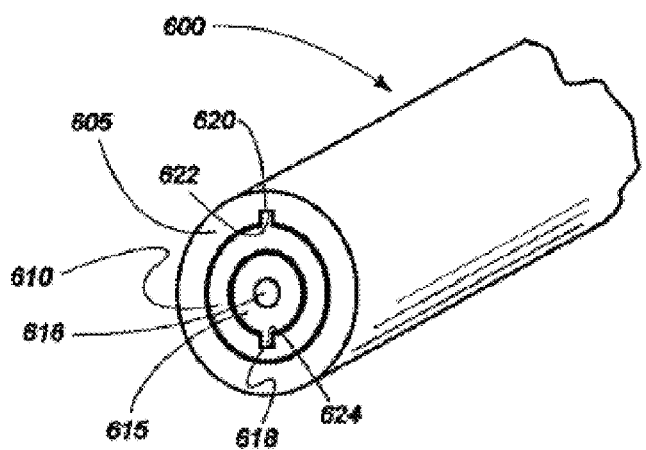
FIG. 13 is an enlarged perspective view of one end of the implant of FIG. 12 showing an optional keyed relationship between three coaxial cannulae to prevent relative rotation between the three components.

FIGS. 12-18 show another embodiment of a percutaneous annuloplasty device according to the present disclosure, in which an implant/delivery system array 600 includes a housing sheath 605 (not seen in FIG. 12), an actuating catheter 610 coaxially slidably mounted within the housing sheath 605, and a core catheter 615 coaxially slidably mounted within the actuating catheter 610. The core catheter has a central lumen 616 (FIG. 13). The actuating catheter 610 and core catheter 615 may be round tubular structures, or as shown in FIG. 13, either or both of the actuating and core catheters may be provided with one or more keyed ridges 618, 620, respectively, to be received by one or more reciprocal slots 622, 624 within the inner lumen of either the housing sheath 605 or the actuating catheter 610, respectively. Such keyed ridges 618, 620 would limit internal rotation of an inner element within an outer element, should such restriction be desirable to minimize or prevent the inner contents from inadvertent displacement due to undesired rotational motion during use.

The implant/delivery system array 600 includes a distal tip 625 at the forward end of the core catheter 615. One or more radial implant support arms 630 have their distal ends 632 pivotably or bendably mounted to the core catheter 615 adjacent its distal tip 625. The proximal ends 634 of the radial implant support arms 630 normally extend along the core catheter 615, but are capable of being displaced outward away from the core catheter.

One or more radial support struts 636 have their proximal ends 638 pivotably or bendably mounted to the distal end of the actuating catheter 610. The distal end 640 of each radial support strut 636 is pivotably or bendably attached to a midpoint of a corresponding radial implant support arm 630. As the actuating catheter 610 is advanced with respect to the core catheter 615, the radial support struts 636 force the radial implant support arms 630 upward and outward in the fashion of an umbrella frame. Thus, the actuating catheter 610, core catheter 615, radial support struts 636, and radial support arms 630 in combination form a deployment umbrella 642.

Figure 14:
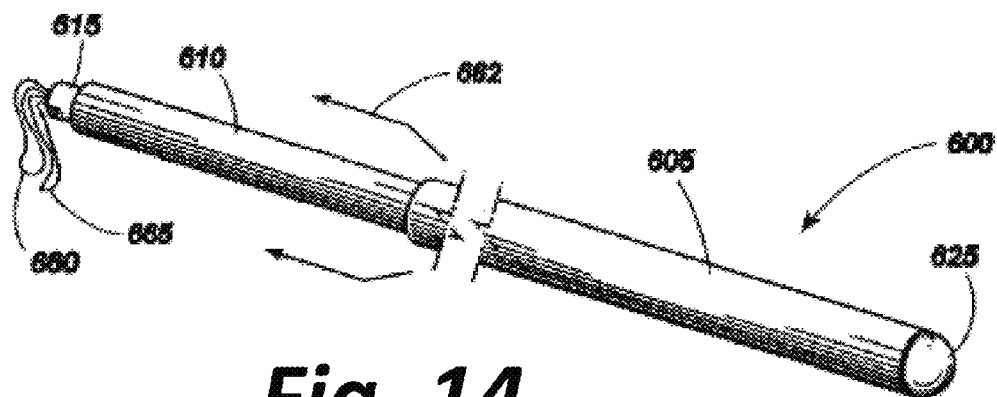
FIG. 14 is a perspective view of the implant of FIG. 12 showing the outer cannula extended to cover the implant.
Figure 15:
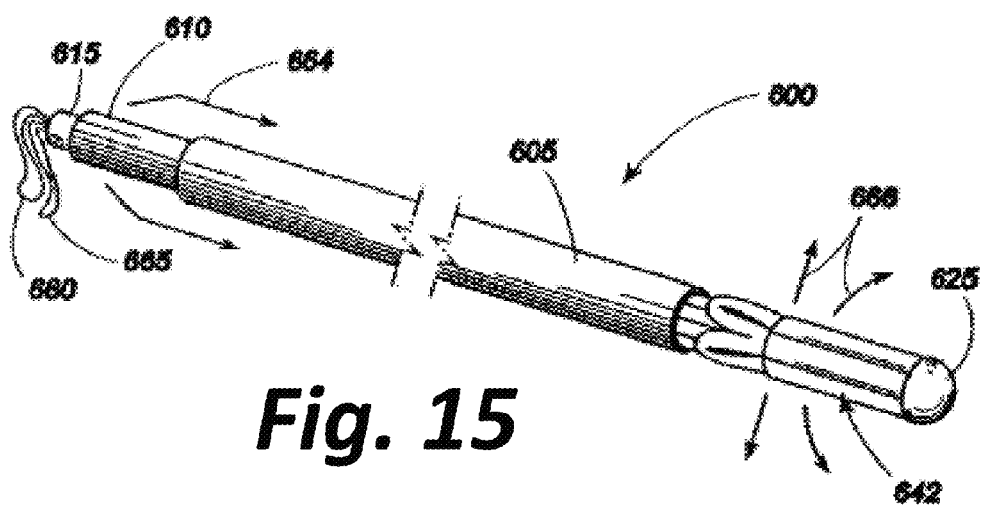
FIG. 15 is a perspective view of the implant of FIG. 12 showing the outer cannula retracted to expose the implant.
Figure 16:
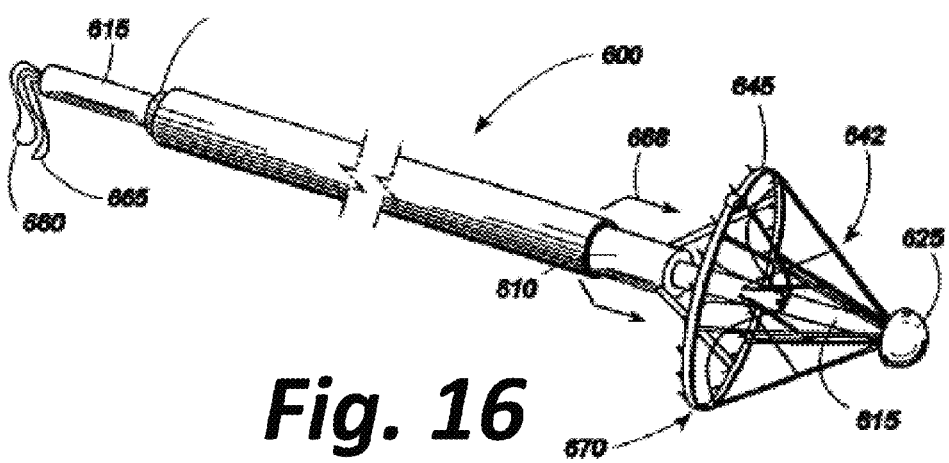
FIG. 16 is a perspective view of the implant of FIG. 12 showing the middle cannula extended to unfold the implant.

A prosthetic implant 645 is releasably attached to the proximal ends 634 of the radial implant support arms 630. Around the periphery of the prosthetic implant 645 and extending proximally therefrom are a plurality of retention barbs 646. In addition, one or more of the radial implant support arms 630 comprise touchdown sensors 648 whose proximal ends extend proximal to the implant 645. Extending through the central lumen 616 (FIG. 13) of the core catheter 615 in the exemplary embodiment 600 and out lateral ports 650 (FIG. 12) spaced proximally from the distal tip 625 are one or more release elements 660, which serve to release the implant 645 from the delivery system, and one or more adjustment elements 665 which serve to adjust the implant's deployed size and effect. Because the release elements 660 and adjustment elements 665 extend through the proximal end of the core catheter 615, as seen in FIGS. 14-16, these elements can be directly or indirectly instrumented or manipulated by the physician. A delivery interface 670 (FIGS. 12, 16) is defined in this example by the interaction of the deployment umbrella 642, the release elements 660, and the implant 645. In the disclosed embodiment, the release elements 660 may be a suture, fiber, or wire in a continuous loop that passes through laser drilled bores in the implant 645 and in the radial implant support arms 630, and then passes through the length of the core catheter 615. In such an embodiment, the implant 645 may be released from the delivery system at a desired time by severing the release element 660 at its proximal end, outside the patient, and then withdrawing the free end of the release element 660 through the core catheter 615.

FIGS. 14-16 show the operation of the implant/delivery system array 600, in which an umbrella-like expansion of the prosthetic implant 645 is achieved by sliding movement of the housing sheath 605, the actuating catheter 610, and the core catheter 615. Referring first to FIG. 14, the housing sheath 605 is extended to cover the forward ends of the actuating catheter 610 and core catheter 615 for intravascular insertion of the implant/delivery system array 600. From this starting position, the housing sheath 605 is retracted in the direction indicated by arrows 662. In FIG. 15 the housing sheath 605 has been retracted to expose the forward end of the actuating catheter 610 and the collapsed deployment umbrella 642. From this position, the actuating catheter 610 is advanced in the direction indicated by arrows 664. This will cause the deployment umbrellas to expand in the directions indicated by arrows 666. FIG. 16 shows the expansion of the deployment umbrella 642 produced by distal motion of the actuating catheter 610 relative to the core catheter 615. After the implant 645 has been positioned and adjusted to the proper size, the housing sheath 605 is advanced in the direction indicated by arrows 668 to collapse and to cover the deployment umbrella 642 for withdrawal of the device from the patient.

Figure 17:
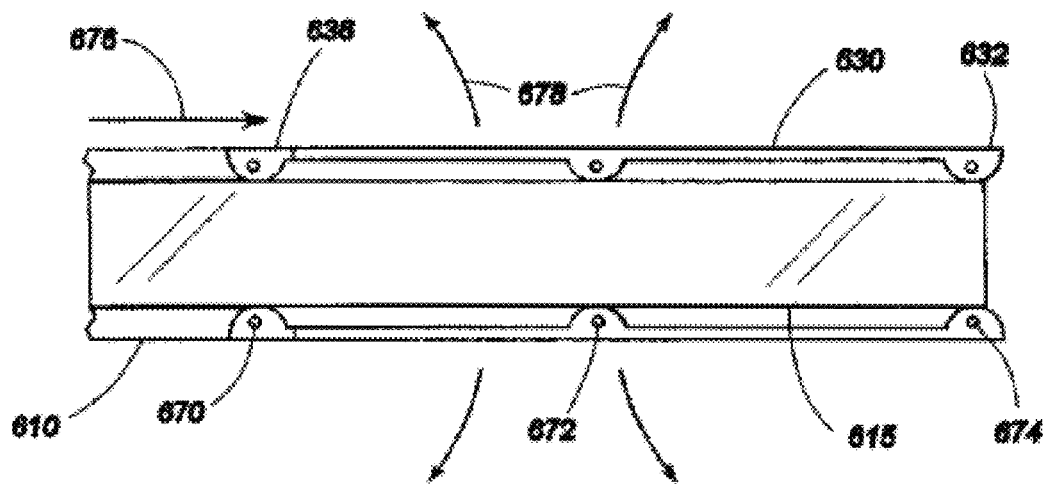
FIGS. 17 and 18 are schematic views illustrating how extension of the middle cannula causes the implant to unfold, where
Figure 18:
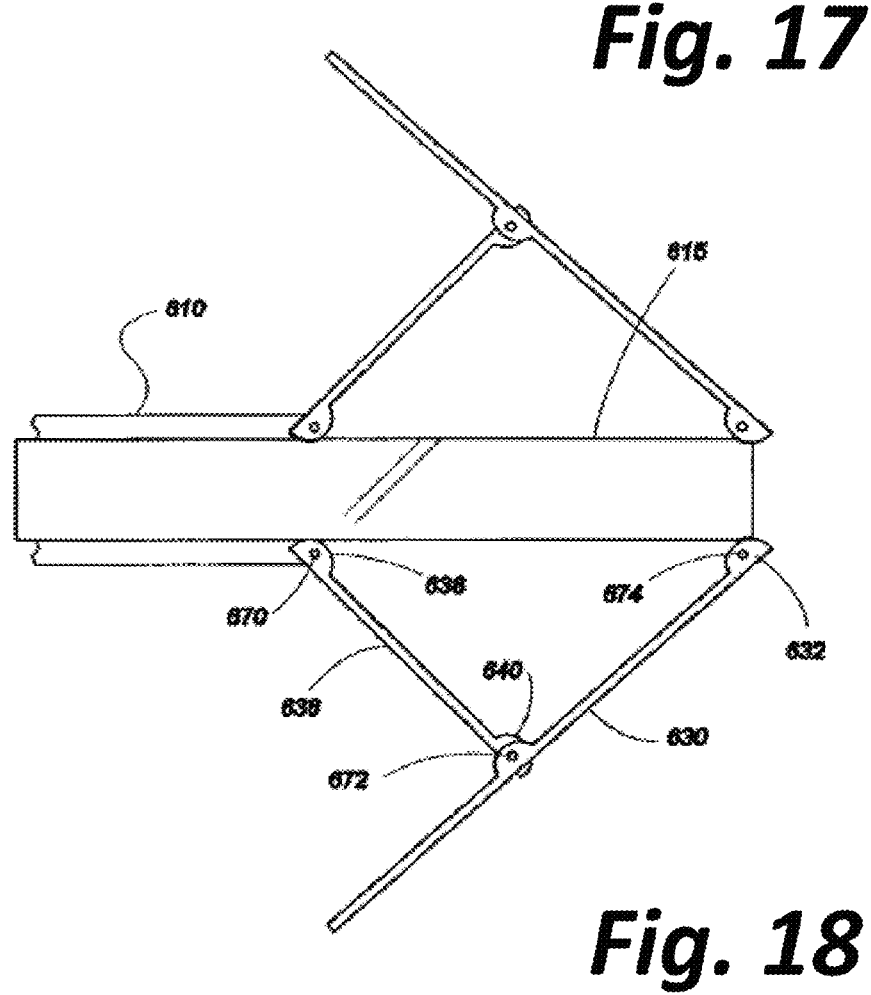

FIGS. 17 and 18 are schematic views illustrating the radial implant support arms 630 and the radial support struts 636 of the implant/delivery system array 600. In FIG. 17, a radial support strut 636 is pivotably attached at its proximal end 638 at a first pivotable joint 670 to the actuating catheter 610. The radial support strut 636 is attached at its distal end 640 to a second pivotable joint 672 at an intermediate point of a corresponding radial implant support arm 630. The radial implant support arm 630 is attached at its distal end 632 by a third pivotable joint 674 to the core catheter 615. FIG. 17 shows the assembly in a closed state. When the actuating catheter 610 is advanced distally over the core catheter 615, as shown by the arrows 676, the radial support strut 636 and the radial implant support arm 630 are extended by the motion at the first pivotable joint 670, the second pivotable joint 672, and the third pivotable joint 674, as shown by the arrows 678. This motion has the effect of expanding the deployment umbrella and folded implant (not shown in FIGS. 17 and 18), allowing the umbrella to achieve its greatest radial dimension prior to engagement and implantation as previously discussed with reference to FIGS. 12-16.

Figure 19:
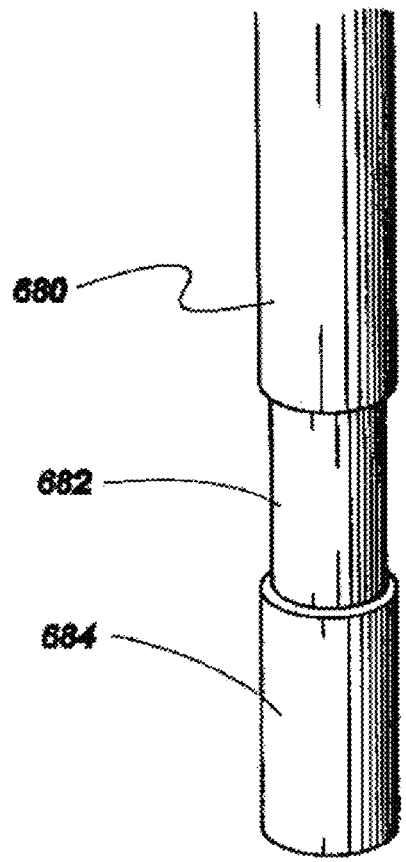
FIG. 19 is a partial perspective view of the lower end of a touchdown sensor of the implant of FIG. 12, showing the sensor in an uncompressed condition.
Figure 20:
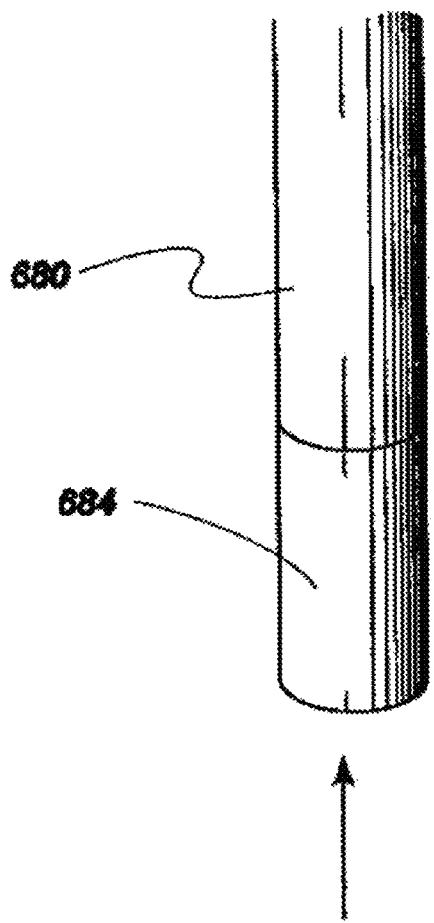
FIG. 20 is a partial perspective view of the lower end of the touchdown sensor of FIG. 19, showing the sensor in a compressed condition.

FIGS. 19 and 20 show further details of the touchdown sensors 648 shown in FIG. 12. The touchdown sensor 648 of FIGS. 19 and 20 includes a distal segment 680, an intermediate segment 682, and a proximal segment 684. The distal segment 680 is spring-mounted, so that it is capable of slidable, telescoping displacement over the intermediate segment 682 to achieve a seamless junction with the proximal segment 684 upon maximal displacement. When the touchdown sensor 648 is in its normal condition, the spring extends the proximal segment 684 such that the sensor assumes the orientation shown in FIG. 19. When the implant 645 (FIG. 12) is seated against the periphery of an anatomical opening, the proximal segment 684 of the sensor 648 is compressed against the distal segment 680, as shown in FIG. 20. The distal segment 680 and the proximal segment 684 are both constructed of, are sheathed by, or otherwise covered with a radio-opaque material. However, the intermediate segment 682 is not constructed or coated with such a radio-opaque material, and is therefore radiolucent. Therefore, when the distal segment 680 is at rest, it is fully extended from the proximal segment 684, and the radiolucent gap represented by the exposed intermediate segment 682 is visible on radiographic examination. However, when the distal segment 680 is brought to maximum closeness with the proximal segment 684, no such gap is radiographically visible, and the touchdown sensor is said to be "activated". This embodiment allows radiographic monitoring of the position of the touchdown sensor 648 with respect to the degree of extension of the distal segment 680. In the embodiment according to the present disclosure as shown, one or more touchdown sensors 648 are employed to ascertain that the delivery system for the prosthetic device is located in the proper position to deploy the implant into the mitral annulus. As this anatomic structure cannot be directly identified on fluoroscopy or standard radiographic procedures, such precise location could be otherwise difficult.

Touchdown detectors within the embodiments according to the present disclosure can have a multiplicity of forms, including the telescoping, spring-loaded, radio-opaque elements joined by a non-radio-opaque element as in the aforementioned example. In embodiments employing magnetic resonance imaging, touchdown detectors according to the present disclosure may utilize metallic segments interposed by nonmetallic segments in a similar telescoping, spring-loaded array. Other embodiments include a visually-evident system with telescoping, spring-loaded elements with color coded or other visual features for procedures in which direct or endoscopic observation would be possible. Still other embodiments of touchdown detectors according to the present disclosure include touchdown detectors provided with microswitches at their tips, such that momentary contact of sufficient pressure completes an electrical circuit and signals the activation of the touchdown detector to the operator. Still other touchdown detectors according to the present disclosure are provided with fiberoptic pathways for Raman laser spectroscopy or other spectral analytical techniques which are capable of detecting unique tissue qualities of the tissue at the desired site for implantation. In addition, still other embodiments according to the present disclosure include touchdown detectors containing electrodes or other electronic sensors capable of detecting and signaling the operator when a desired electrophysiologic, impedance, or other measurable quality of the desired tissue is detected for proper implantation. Such electrophysiologic touchdown detectors may include electrical circuits that produce visual, auditory, or other signals to the operator that the detectors are activated and that the implant is in the proper position for attachment.

In yet other embodiments according to the present disclosure, other intracardiac or extracardiac imaging techniques including, but not limited to, intravascular ultrasound, nuclear magnetic resonance, virtual anatomic positioning systems, or other imaging techniques may be employed to confirm proper positioning of the implant, obviating the need for the touchdown sensors as previously described.

Figure 21:
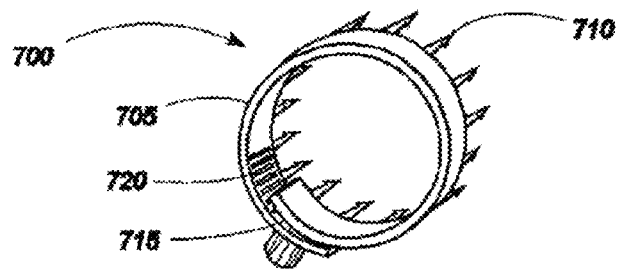
FIG. 21 is a perspective end view of a fourth embodiment of an implant for reducing or reshaping the circumference of an anatomic orifice.
Figure 22:
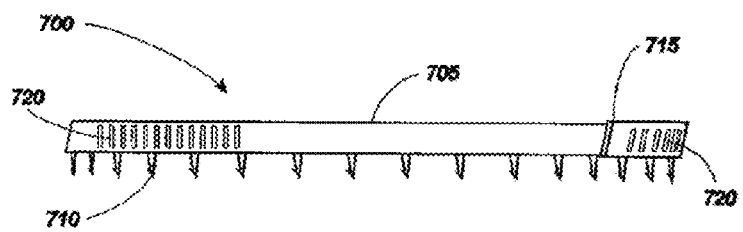
FIG. 22 is a side view of the implant of FIG. 21 with the implant opened up to show its full length.
Figure 23:
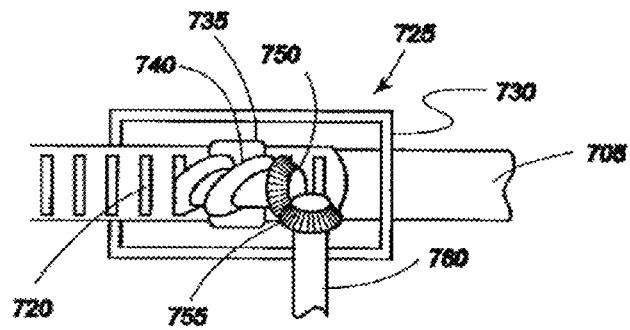
FIG. 23 is a side view of the adjustment mechanism for the implant of FIG. 21.

FIGS. 21-24 show details of another implant 700 that may be implanted using implant/delivery system array 600 according to the present disclosure. In this embodiment, the implant body 705 is band-like and flexible. Through much of its length, the implant body 705 is provided with a series of retention barbs 710 which are oriented to facilitate placement, retention, and removal of the device. The implant body 705 is also provided with an adjustable section 715, which is provided in this example with a series of adjustment stops 720. The adjustment stops 720 may be slots, holes, detents, dimples, ridges, teeth, raised elements, or other mechanical features to allow measured adjustment of the implant 700 in use. In the embodiment shown in FIGS. 21-24, the adjustment stops 720 are engaged by a geared connector 725. FIG. 21 is a perspective end view showing the implant body 705 curved on itself, with the retention barbs 710 to the exterior, and with the adjustable section 715 passing through its engagement with the geared connector 725 and curving internally within the implant body 705 to form a closed, round structure. FIG. 23 shows details of an exemplary geared connector 725, in which a housing 730 is connected to the implant body 705. The housing 730 contains and supports a mechanical worm 740 with an attached first geared head 750 which mates with a second geared head 755. The second geared head 755 is attached to an adjustment stem 760 which is machined to receive a screwdriver-like adjustment element. The various embodiments according to the present disclosure may require a number of forms of adjustment elements. In the present example, the adjustment element is provided as a finely coiled wire with a distal tip machined to be received by a receiving slot in the adjustment stem 760 (not shown). The relationship between the distal tip of the adjustment element and the adjustment stem 760 is mechanically similar to a screwdriver bit and screwhead, such that torsion imparted to the adjustment element by the operator will result in the turning of the adjustment stem 760 and second geared head 755 allows motion of the first geared head 750 and worm 740, which creates motion of the adjustable implant section 715 as the worm engages with the series of adjustment stops 720. Excess length of the adjustable section 715 passes through a band slot 735 (FIG. 23), thus allowing the band to move concentrically inside the closed implant body 705. The adjustment element in this embodiment may be designed to remain in place after the deployment umbrella has been retracted and withdrawn. The connection between the adjustment element's distal tip and the adjustment stem 760 may be a simple friction connection, a mechanical key/slot formation, or may be magnetically or electronically maintained.

Figure 24:
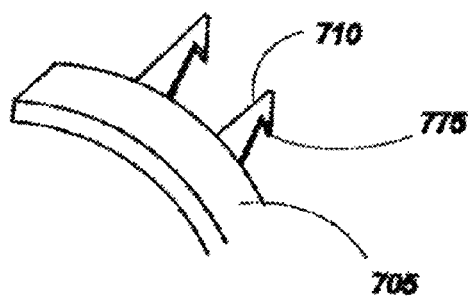
FIG. 24 is an enlarged view of two of the retention barbs of the implant of FIG. 21.

As further shown in FIG. 21, the exemplary embodiment employs unidirectional retention barbs 710 which are attached to the outer perimeter of the implant body 705. The retention barbs 710 are oriented in a consistent, tangential position with respect to the implant body 705 such that rotational motion of the implant body will either engage or release the retention barbs 710 upon contact with the desired tissue at the time of deployment. This positioning of the retention barbs 710 allows the operator to "screw in" the implant 700 by turning the implant 700 upon its axis, thus engaging the retention barbs 710 into the adjacent tissue. As shown in FIG. 24, the retention barbs 710 may each be further provided with a terminal hook 775 at its free end which would allow for smooth passage through tissue when engaging the retention barbs 710 by rotating the implant 700, without permitting the implant 700 to rotate in the opposite direction because of the action of the terminal hooks 775 grasping the surrounding tissue (much like barbed fish hooks). The terminal hooks 775 thus ensure the seating of the implant 700 into the surrounding tissue.

Figure 25:
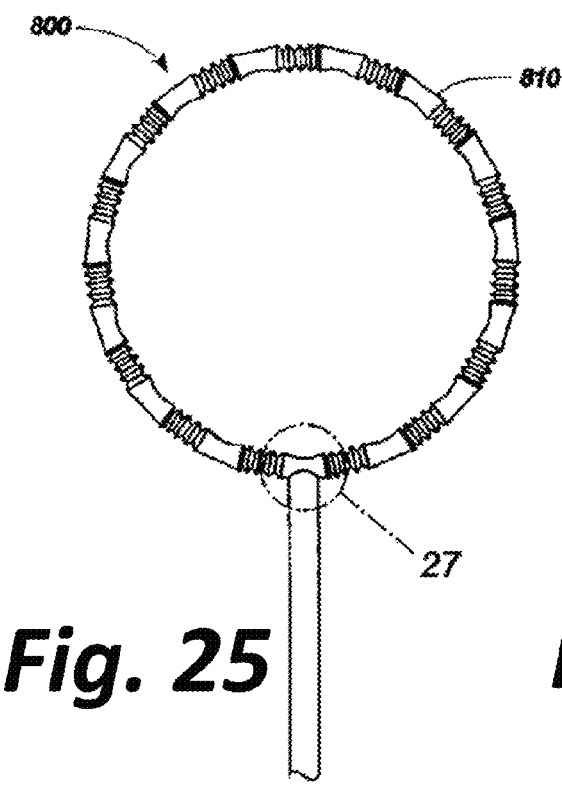
FIG. 25 is a front view of a fifth embodiment of an implant for reducing or reshaping the circumference of an anatomic orifice, with the implant shown in its expanded configuration.
Figure 26:
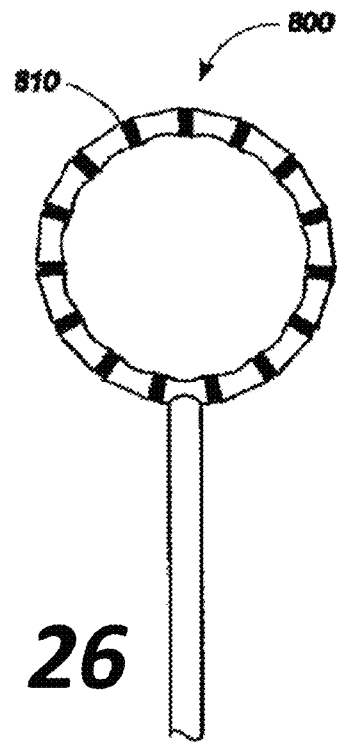
FIG. 26 is a front view of the implant of FIG. 25, with the implant shown in its contracted configuration.
Figure 27:
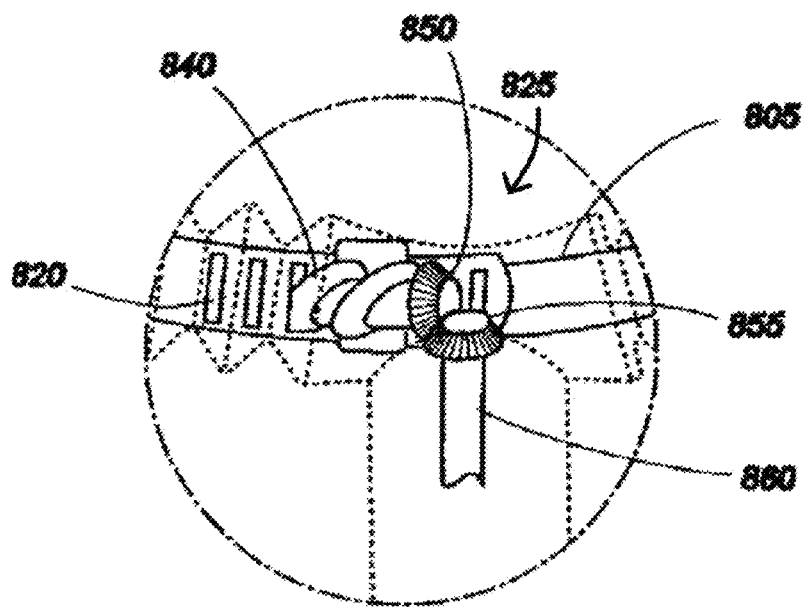
FIG. 27 is an enlarged view of the area indicated by the circle 27 in FIG. 25, with the outer body removed to show interior detail.

FIGS. 25-27 illustrate another embodiment of an implant 800 as contemplated according to the present disclosure. The implant 800 includes a band 805 (FIG. 27), but the retention barbs of the previous example have been eliminated in favor of an outer fabric implant sheath 810. The fabric sheath 810 can be sutured or otherwise affixed to the anatomic tissue in a desired location. The circumference of the implant body 800 is adjusted through a geared connector 825 similar to the geared connector of the band-like implant array shown in FIG. 23. More specifically, adjustment stops 820 on the band are engaged by a mechanical worm 840 with an attached first geared head 850. The first geared head 850 mates with a second geared head 855. The second geared head 855 is attached to an adjustment stem 860 which is machined to receive a screwdriver-like adjustment element.

Figure 28:
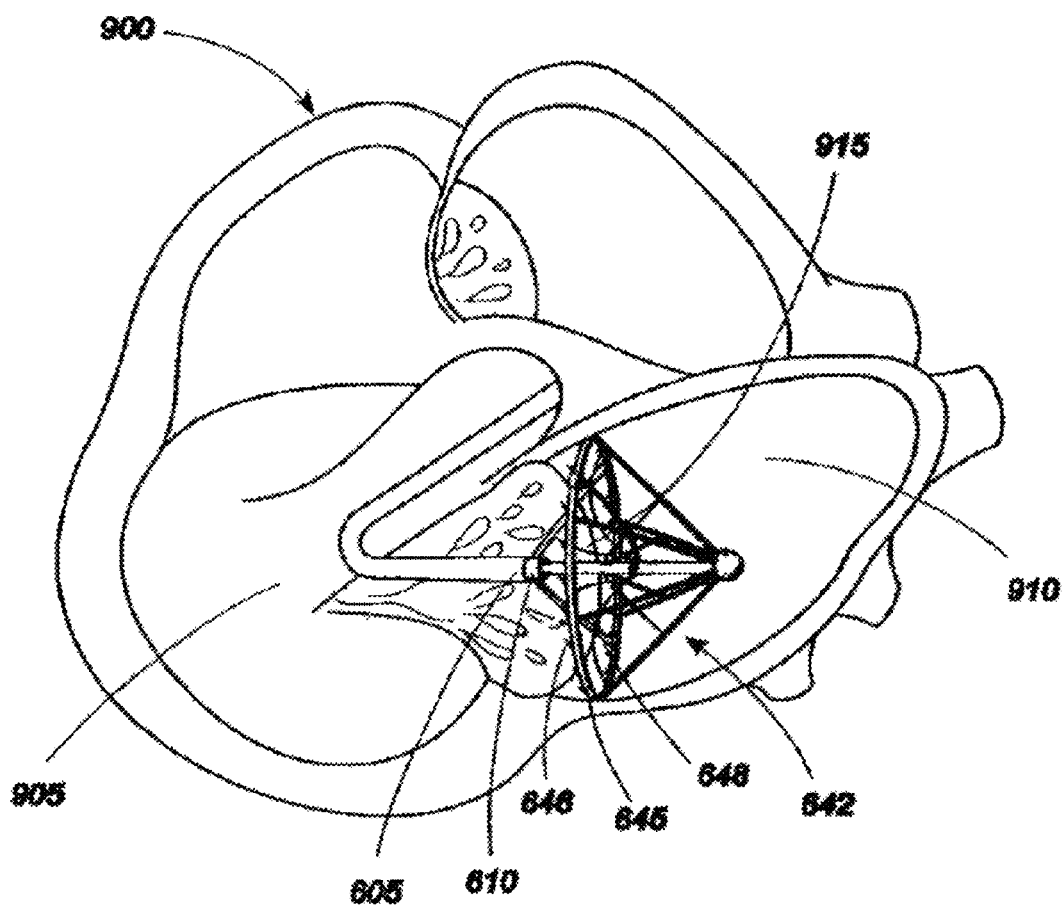
FIG. 28 is a schematic view showing the implant of FIG. 12 anatomically positioned at the mitral annulus in a heart with the implant in a fully expanded state.

FIG. 28 illustrates an example of the method of use of the implant/delivery system array 600 of FIG. 12 for positioning an implant 645 in a patient with ischemic annular dilatation and mitral regurgitation. Peripheral arterial access is obtained via conventional cutdown, arterial puncture, or other standard access techniques. After access to the arterial system is attained, guidewire placement is performed and intravascular access to the heart 900 is obtained using fluoroscopic, ultrasound, three-dimensional ultrasound, magnetic resonance, or other real-time imaging technique. The guidewire, deployment device and implant are passed through the aortic valve in a retrograde fashion into the left ventricle 905 and then into the left atrium 910. At this point, the operator retracts the housing sheath 605, thus unsheathing the collapsed deployment umbrella 642 and implant 645. The deployment umbrella 642 is then distended by the distal motion of the actuating catheter, causing the radial support arms and struts to fully distend. At this point, the touchdown detectors 648 are not in contact with any solid structures, and are fully extended with their radiolucent gaps visible on the imaging system. Once the deployment umbrella is distended, the entire assembly is pulled back against the area of the mitral valve 915. At least two touchdown detectors 648 are employed in one embodiment according to the present disclosure. When all touchdown detectors show the disappearance of their intermediate, non-opaque, intermediate segments and are thus activated, then the deployment umbrella must be in contact with the solid tissue in the region of the mitral annulus/atrial tissue, and further implant deployment and adjustment may proceed. However, if any one touchdown detector is not activated, and a radiolucent gap persists, then the device is not properly positioned, and may be repositioned before further deployment. Thus, the touchdown detector system may assist in the deployment and adjustment of prosthetic devices by the delivery system according to the present disclosure. Once properly positioned, the operator rotates the actuation catheter in a prescribed clockwise or counterclockwise manner to engage the retention barbs on the implant into the tissue in the region of the mitral annulus/atrial tissue. Should repositioning be required, a reverse motion would disengage the retention barbs from the annular/atrial tissue, and repositioning may be performed, again using the touchdown detectors for proper placement. Once firmly seated, the adjustment element(s) are operated to achieve the desired degree of annular reduction. Real-time transesophageal echocardiography, intravascular echocardiography, intracardiac echocardiography, or other modalities for assessing mitral function may then be employed to assess the physiologic effect of the repair on mitral function, and additional adjustments may be performed. Once a desired result has been achieved, the release elements are activated to detach the implant from the deployment umbrella. The operator then retracts the actuating catheter and extends the housing sheath, collapsing the deployment umbrella and covering the components for a smooth and atraumatic withdrawal of the device from the heart and vascular system.

If desired, the adjustment element may be left in position after the catheter components are withdrawn for further physiologic adjustment. In yet other embodiments according to the present disclosure, a catheter-based adjustment element may subsequently be re-inserted through a percutaneous or other route. Such an adjustment element may be steerably operable by the operator, and may be provided with magnetic, electronic, electromagnetic, or laser-guided systems to allow docking of the adjustment element with the adjustment mechanism contained within the implant. In still other embodiments, the adjustment mechanism may be driven by implanted electromechanical motors or other systems, which may be remotely controlled by electronic flux or other remote transcutaneous or percutaneous methods.

In the case of pulmonic valve repair, initial catheter access may be achieved through a peripheral or central vein. Access to the pulmonary valve may also be achieved from below the valve once central venous access is achieved by traversing the right atrium, the tricuspid valve, the right ventricle, and subsequently reaching the pulmonic valve.

In yet other embodiments according to the present disclosure, catheter access to the left atrium can be achieved from cannulation of central or peripheral veins, thereby achieving access to the right atrium. Then a standard atrial transseptal approach may be utilized to access the left atrium by creation of an iatrogenic atrial septal defect (ASD). In such a situation, the mitral valve may be accessed from above the valve, as opposed to retrograde access. The implant and a reversed deployment umbrella may be utilized with implant placement in the atrial aspect of the mitral annulus, with the same repair technique described previously. The iatrogenic ASD may then be closed using standard device methods. Access to the aortic valve may also be achieved from above the aortic valve via arterial access in a similar retrograde fashion.

In various embodiments anticipated by the present disclosure, the implant body may be straight, curved, circular, ovoid, polygonal, or some combination thereof. In various embodiments anticipated by the present disclosure, the implant may be capable of providing a uniform or non-uniform adjustment of an orifice or lumen within the body. The implant body may further completely enclose the native recipient anatomic site, or it may be provided in an interrupted form that encloses only a portion of the native recipient anatomic site. In still other embodiments of the present disclosure, the implant body may be a solid structure, while in yet other embodiments the implant body may form a tubular or otherwise hollow structure. In one embodiment of the present disclosure, the body may further be a structure with an outer member, an inner member, and optional attachment members. In such an embodiment, the outer member of the implant body may serve as a covering for the implant, and is designed to facilitate and promote tissue ingrowth and biologic integration to the native recipient anatomic site. The outer member in such an embodiment may be fabricated of a biologically compatible material, such as Dacron, PTFE, malleable metals, other biologically compatible materials or a combination of such biologically compatible materials in a molded, woven, or nonwoven configuration. The outer member in such an embodiment also serves to house the inner member. In this embodiment, the inner member provides an adjustment means that, when operated by an adjustment mechanism, is capable of altering the shape and/or size of the outer member in a defined manner. It should be understood that the implant body may be either adjustable or non-adjustable.

In alternate embodiments according to the present disclosure, the adjustment means may be located external to or incorporated within the outer member. In yet additional alternate embodiments contemplated by the present disclosure, the implant body may consist of an adjustment means without a separate outer member covering said adjustment means.

In various embodiments according to the present disclosure, the adjustment means may include a mechanism which may be threaded or non-threaded, and which may be engaged by the action of a screw or worm screw, a friction mechanism, a friction-detent mechanism, a toothed mechanism, a ratchet mechanism, a rack and pinion mechanism, or such other devices to permit discrete adjustment and retention of a desired size and desired position, once the proper size is determined.

In yet other embodiments according to the present disclosure, the adjustment means may comprise a snare or purse string-like mechanism in which a suture, a band, a wire or other fiber structure, braided or non-braided, monofilament or multifilament, is capable of affecting the anatomic and/or physiologic effects of the implant device on a native anatomic recipient site upon varying tension or motion imparted to said wire or fiber structure by a surgeon or other operator. Such an adjustment means may be provided as a circular or non-circular structure in various embodiments. Changes in tension or motion may change the size and/or shape of the implant.

In various embodiments according to the present disclosure, the adjustment means may be a metallic, plastic, synthetic, natural, biologic, or any other biologically compatible material, or combination thereof. Such adjustment means may further be fabricated by extrusion or other molding techniques, machined, or woven. Furthermore, in various embodiments of the present disclosure, the adjustment means may be smooth or may include slots, beads, ridges, or any other smooth or textured surface.

In various embodiments of the present disclosure, the implant body may be provided with one or more attachment members such as grommets or openings or other attachment members to facilitate attachment of the implant to the native recipient site. In alternate embodiments, the implant body may attach to or incorporate a mechanical tissue interface system that allows a sutureless mechanical means of securing the implant at the native recipient site. In still other alternate embodiments, sutures or other attachment means may be secured around or through the implant body to affix the implant body to the native recipient site. In yet other embodiments of the present disclosure, mechanical means of securing the implant body to the native recipient site may be augmented or replaced by use of fibrin or other biologically-compatible tissue glues or similar adhesives.

In additional various embodiments according to the present disclosure, the adjustable implant may be employed to adjustably enlarge or maintain the circumference or other dimensions of an orifice, ostium, lumen, or anastomosis in which a disease process tends to narrow or constrict such circumference or other dimensions.

In various embodiments according to the present disclosure, an adjustment mechanism may be provided to interact with the adjustment means to achieve the desired alteration in the size and/or position of the adjustment means. Such an adjustment mechanism may include one or more screws, worm-screw arrays rollers, gears, frictional stops, a friction-detent system, ratchets, rack and pinion arrays, microelectromechanical systems, other mechanical or electromechanical devices or some combination thereof.

In some embodiments as contemplated by the present disclosure, an adjustment tool may be removably or permanently attached to the adjustment mechanism and disposed to impart motion to the adjustment mechanism and, in turn, to the adjustment means to increase or decrease the anatomic effect of the implant on the native recipient site.

In alternate embodiments according to the present disclosure, micromotor arrays with one or more micro-electromechanical motor systems with related electronic control circuitry may be provided as an adjustment means, and may be activated by remote control through signals conveyed by electromagnetic radiation or by direct circuitry though electronic conduit leads which may be either permanently or removably attached to said micromotor arrays.

In still other various embodiments according to the present disclosure, the adjustment mechanism may be provided with a locking mechanism disposed to maintain the position of the adjustment means in a selected position upon achievement of the optimally desired anatomic and/or physiologic effect upon the native recipient site and the bodily organ to which it belongs. In other embodiments, no special locking mechanism may be necessary due to the nature of the adjustment means employed.

In yet other alternate embodiments according to the present disclosure, the adjustment means and/or the outer member structure may be a pliable synthetic material capable of rigidification upon exposure to electromagnetic radiation of selected wavelength, such as ultraviolet light. In such embodiments, exposure to the desired electromagnetic radiation may be achieved by external delivery of such radiation to the implant by the surgeon, or by internal delivery of such radiation within an outer implant member using fiberoptic carriers placed within said outer implant member and connected to an appropriate external radiation source. Such fiberoptic carriers may be disposed for their removal in whole or in part from the outer implant member after suitable radiation exposure and hardening of said adjustment means.

The present disclosure also provides methods of using an implant device, which may be adjustable or non-adjustable, to selectively alter the anatomic structure and/or physiologic effects of tissues forming a passageway for blood, other bodily fluids, nutrient fluids, semi-solids, or solids, or wastes within a mammalian body. Various embodiments for such uses of adjustable implants include, but are not limited to, open surgical placement of said adjustable implants at the native recipient site through an open surgical incision, percutaneous or intravascular placement of said implants under visual control employing fluoroscopic, ultrasound, magnetic resonance imaging, or other imaging technologies, placement of said implants through tissue structural walls, such as the coronary sinus or esophageal walls, or methods employing some combination of the above techniques. In various embodiments as contemplated by the present disclosure, adjustable implants may be placed and affixed in position in a native recipient anatomic site by trans-atrial, trans-ventricular, trans-arterial, trans-venous (i.e., via the pulmonary veins) or other routes during beating or non-beating cardiac surgical procedures or endoscopically or percutaneously in other surgical procedures.

Furthermore, alternate methods for use of an adjustable implant device may provide for the periodic, post-implantation adjustment of the size of the anatomic structure receiving said implant device as needed to accommodate growth of the native recipient site in a juvenile patient or other changes in the physiologic needs of the recipient patient.

Adjustment of the adjustable implants and the methods for their use as disclosed herein contemplate the use by the surgeon or operator of diagnostic tools to provide an assessment of the nature of adjustment needed to achieve a desired effect. Such diagnostic tools include, but are not limited to, transesophageal echocardiography, echocardiography, diagnostic ultrasound, intravascular ultrasound, virtual anatomic positioning systems integrated with magnetic resonance, computerized tomographic or other imaging technologies, endoscopy, mediastinoscopy, laparoscopy, thoracoscopy, radiography, fluoroscopy, magnetic resonance imaging, computerized tomographic imaging, intravascular flow sensors, thermal sensors or imaging, remote chemical or spectral analysis, or other imaging or quantitative or qualitative analytic systems.

In one aspect, the implant/delivery system of the present disclosure comprises a collapsible, compressible, or distensible prosthetic implant and a delivery interface for such a prosthetic implant that is capable of delivering the prosthetic implant to a desired anatomic recipient site in a collapsed, compressed, or non-distended state, and then allowing controlled expansion or distension and physical attachment of such a prosthetic implant by a user at the desired anatomic recipient site. Such a system permits the delivery system and prosthetic implant to be introduced percutaneously through a trocar, sheath, via Sullinger technique, needle, or endoscopically through a natural bodily orifice, body cavity, or region and maneuvered by the surgeon or operator to the desired anatomic recipient site, where the delivery system and prosthetic implant may be operably expanded for deployment. When desirable, the implant/delivery system according to the present disclosure is also capable of allowing the user to further adjust the size or shape of the prosthetic implant once it has been attached to the desired anatomic recipient site. The delivery system according to the present disclosure is then capable of detaching from its interface with the prosthetic implant and being removed from the anatomic site by the operator. The delivery system and prosthetic implant may be provided in a shape and size determined by the anatomic needs of an intended native recipient anatomic site within a mammalian patient. Such a native recipient anatomic site may be a heart valve or other anatomic sites, including anatomic orifices, within a mammalian body that are creating dysfunction that might be relieved by an implant capable of changing the size and shape of that site and maintaining a desired size and shape after surgery.

In various embodiments contemplated by the present disclosure, the delivery system may be a catheter, wire, filament, rod, tube, endoscope, or other mechanism capable of reaching the desired recipient anatomic site through an incision, puncture, trocar, or through an anatomic passageway such as a vessel, orifice, or organ lumen, or trans-abdominally or trans-thoracically. In various embodiments according to the present disclosure, the delivery system may be steerable by the operator. The delivery system may further have a delivery interface that would retain and convey a prosthetic implant to the desired recipient anatomic site. Such a delivery interface may be operably capable of distending, reshaping, or allowing the independent distension or expansion of such a prosthetic implant at the desired recipient anatomic site. Furthermore, such a delivery interface may provide an operable means to adjust the distended or expanded size, shape, or physiologic effect of the prosthetic implant once said implant has been attached in situ at the desired recipient anatomic site. In various embodiments according to the present disclosure, such adjustment may be carried out during the procedure in which the implant is placed, or at a subsequent time. Depending upon the specific anatomic needs of a specific application, the delivery interface and the associated prosthetic implant may be straight, curved, circular, helical, tubular, ovoid, polygonal, or some combination thereof. In still other embodiments of the present disclosure, the prosthetic implant may be a solid structure, while in yet other embodiments the prosthetic implant may form a tubular, composite, or otherwise hollow structure. In one embodiment of the present disclosure, the prosthetic implant may further be a structure with an outer member, an inner member, and optional attachment members. In such an embodiment, the outer member of the prosthetic implant may serve as a covering for the implant, and is designed to facilitate and promote tissue ingrowth and biologic integration to the native recipient anatomic site. The outer member in such an embodiment may be fabricated of a biologically compatible material, such as Dacron, PTFE, malleable metals, other biologically compatible materials or a combination of such biologically compatible materials in a molded, woven, or nonwoven configuration. The outer member in such an embodiment also serves to house the inner member. In this embodiment, the inner member provides an adjustment means that, when operated by an adjustment mechanism, is capable of altering the shape and/or size of the outer member in a defined manner.

In various embodiments according to the present disclosure, the delivery interface would have an attachment means to retain and convey the prosthetic implant en route to the native anatomic recipient site and during any in situ adjustment of the prosthetic implant once it has been placed by the operator. Such an attachment means would be operably reversible to allow detachment of the prosthetic implant from the delivery interface once desired placement and adjustment of the prosthetic implant has been accomplished.

Figure 29:
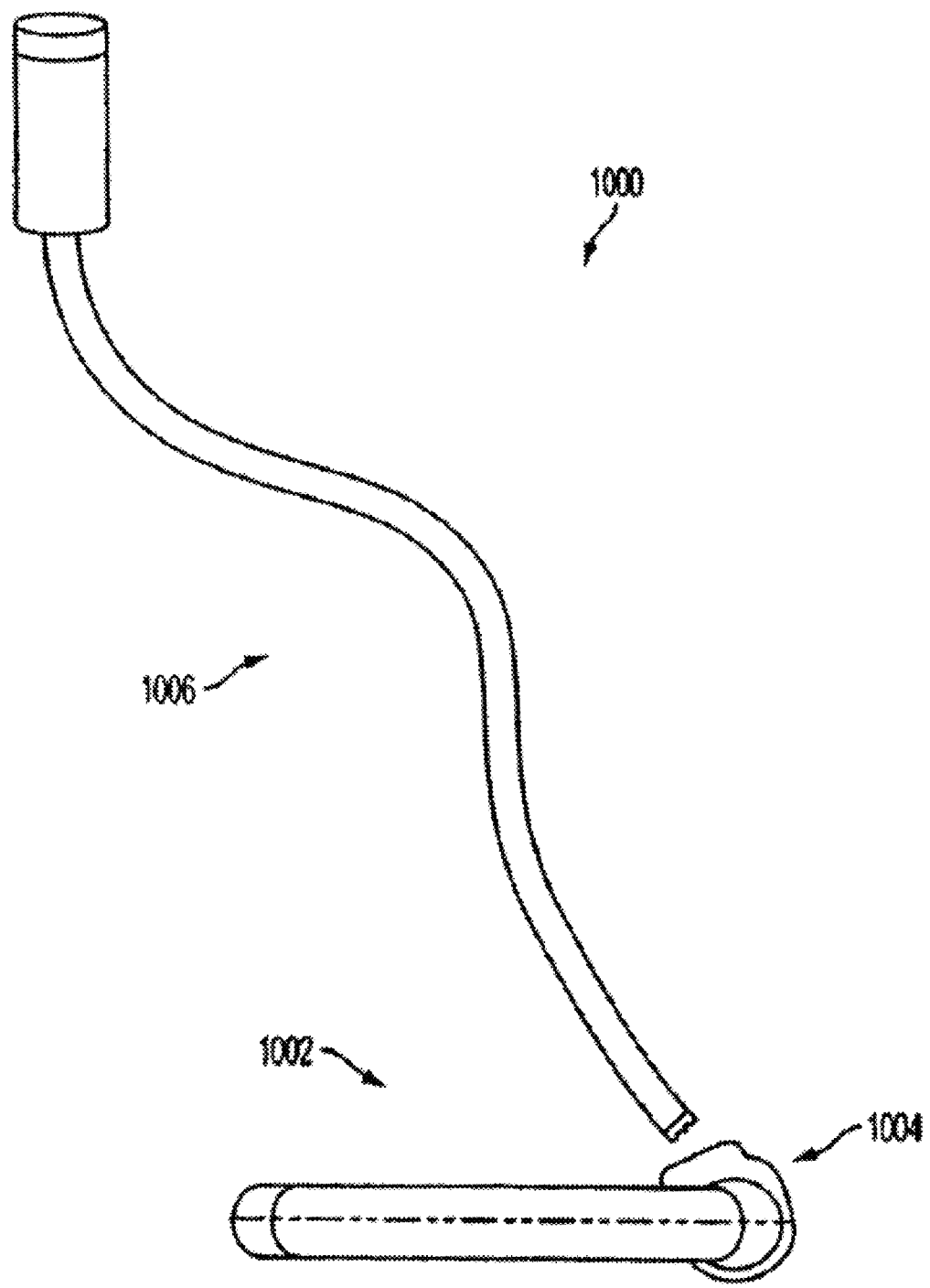
FIG. 29 is a schematic view of an embodiment of an implantable device.

In one embodiment of the present disclosure, illustrated in FIG. 29, an implantable device system 1000 for controlling at least the size or shape of an anatomical structure or lumen includes an implantable device 1002 and an adjustment tool 1006. The anatomical structure or lumen is an anatomic site with dysfunction that can be relieved by the implantable device 1002 to change the size or shape of the anatomic site.

The implantable device 1002, in one exemplary embodiment, has a diameter no larger than about 3.5 mm. In another embodiment, the implantable device 1002 is configured to have variable size relative to its placement at an annulus of a heart valve. The implantable device 1002 has an adjustment mechanism 1004 configured to adjust the dimensions of the implantable device 1002. In one embodiment, the torqueable adjustment tool 1006 provides adjustment of the dimensions of the implantable device 1002. The adjustment mechanism 1004, in some embodiments, may be oriented to receive the adjustment tool from a direction generally perpendicular to the primary plane defined by the implantable device 1002. Such an orientation is advantageous for intravenous access of the tool and in situ adjustment of the implantable device 1002. The implantable device 1002 can have a configuration in which there are different pulling rates at different sections of the implantable device 1002. The implantable device 1002 may optionally include a flexible tube (1032, FIG. 36) and an outer fabric sheath (810, FIGS. 25 and 26), which are not shown in the subsequent figures for clarity. The outer fabric sheath can be sutured, stapled, clipped, coiled, or otherwise affixed to anatomic tissue in a desired location. Generally, the desired location is considered to be the internal surface of the area to be controlled, such as, for example, an interior wall of an organ, artery, or other internal anatomic passage. Also, while the implantable device 1002 is generally shown in the subsequent figures to have a "D"-shaped configuration, it should be understood that other shapes can be used in accordance with embodiments of the present disclosure.

Still referring to FIG. 29, in certain embodiments, the adjustment tool 1006 is at least partially hollow, and in one specific embodiment at least 50% hollow. The adjustment tool 1006 may be an elongated tool, which has a proximal end and a distal end releasably attached to the adjustment mechanism 1004 of implantable device 1002. The adjustment tool 1006 may extend from its distal end coupled to the adjustment mechanism 1004 to a control interface (e.g., handle) at its proximal end located preferably outside of the patient's body. The adjustment tool 1006, when coupled to the adjustment mechanism 1004 of implantable device 1002, can provide a preferential shape change of the implantable device 1002 in planar and non-planar directions. The adjustment tool 1006 can adjust the implantable device 1002 in terms of narrowing or widening the dimensions of the implantable device 1002.

Figure 30A:
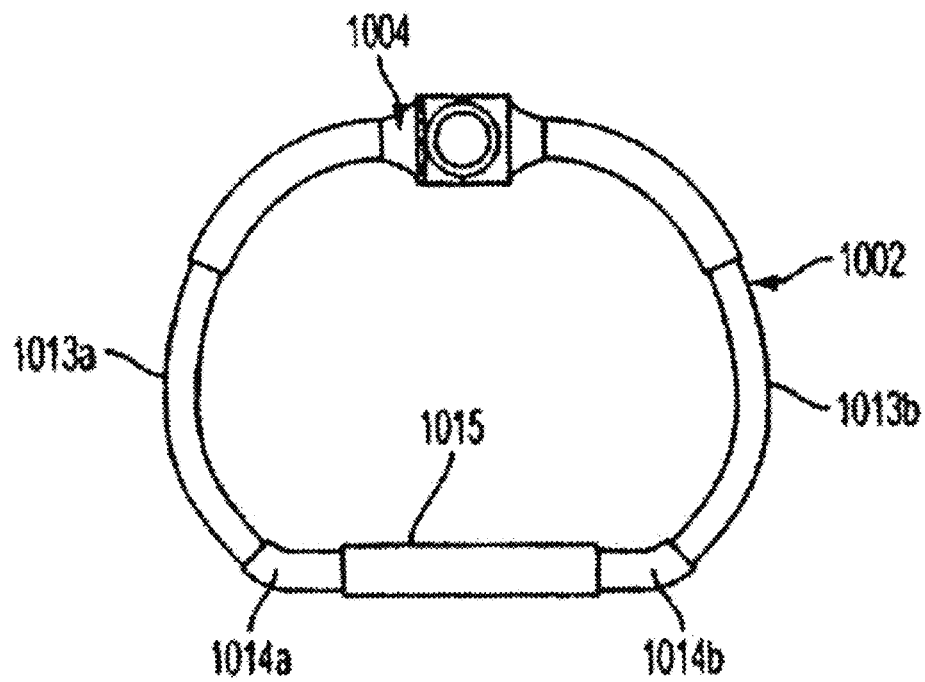
FIG. 30A is a front view of the implantable device of FIG. 29.
Figure 30B:
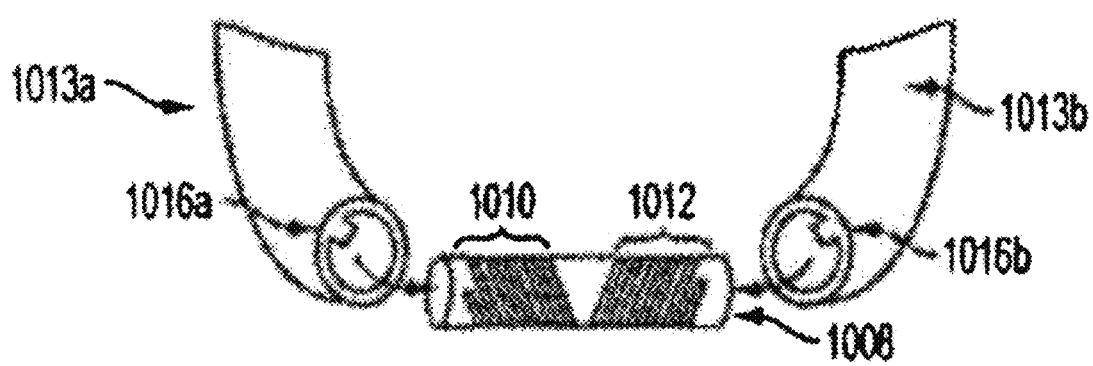
FIG. 30B is an enlarged schematic view of a threaded member in the implantable device of FIG. 29.

FIG. 30A is a front view of the implantable device 1002 without showing an optional flexible outer tube and fabric sheath. The implantable device includes adjustment mechanism 1004 and adjustable tube portions 1013a and 1013b, which slide within hollow tube portions 1014a and 1014b, and retaining tube 1015. FIG. 30B is a schematic view of a disassembled portion of implantable device 1002 with retaining tube 1015 removed. As shown in FIG. 30B, in various embodiments, the implantable device 1002 includes a threaded rod 1008 threaded with right-hand helical grooves 1010 and left-hand helical grooves 1012. Other embodiments may include a threaded rod 1008 with helical grooves in a single direction (e.g., all right-hand grooves or all left-hand grooves). Threaded rod 1008 may be a rigid material such as titanium, stainless steel, or a polymer. Adjustable tube portions 1013a and 1013b enclose at least a portion of grooves 1010 and 1012 so that pins 1016a, 1016b or protuberances on the inside diameter of the adjustable tube portions 1013a, 1013b are engaged by the grooves 1010 and 1012, respectively. In other embodiments, pins 1016a, 1016b may be replaced by threads along the inside diameter of the adjustable tube portions 1013a, 1013b. Helical grooves 1010 and 1012 may be single channels or multiple channels to engage single pins 1016a, 1016b or multiple pins. Hollow tube portions 1014a, 1014b are relatively rigid to maintain the curvature of the adjustable tube portions 1013a, 1013b regardless of the adjustment position.

The implantable device 1002 can have a coating including, but not limited to, heparin, an antibiotic, collagen, an agent that promotes tissue in-growth, PGLA, a decalcification agent and the like. The implantable device 1002 can be made of a variety of materials including, but not limited to, a shape-memory alloy (SMA), a shape-memory polymer (SMP), titanium, stainless steel, polymer, a suture-based material, a biological material and the like.

Figure 31:
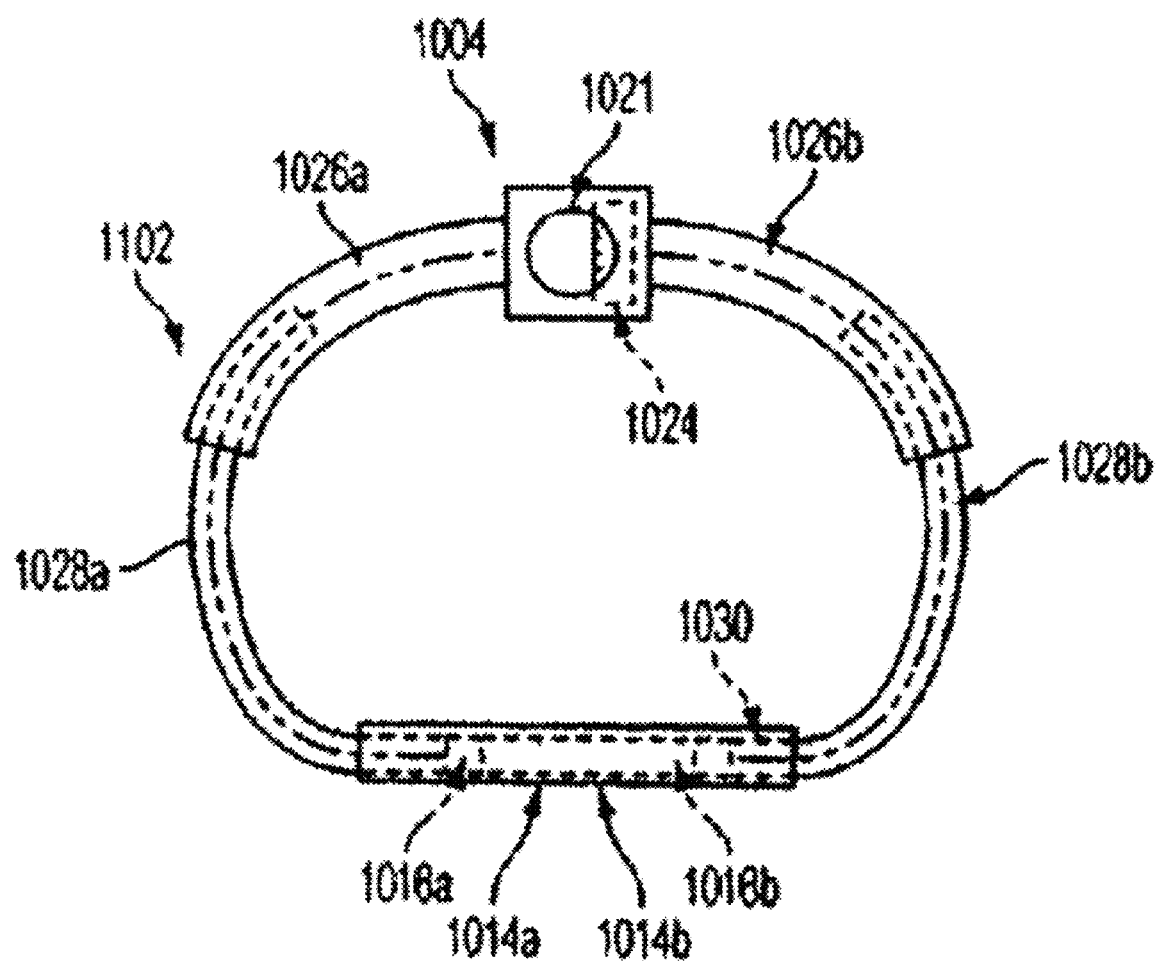
FIG. 31 is a front view of an embodiment of an implantable device having outer tubing and inner tubing in a relative first position.
Figure 32:
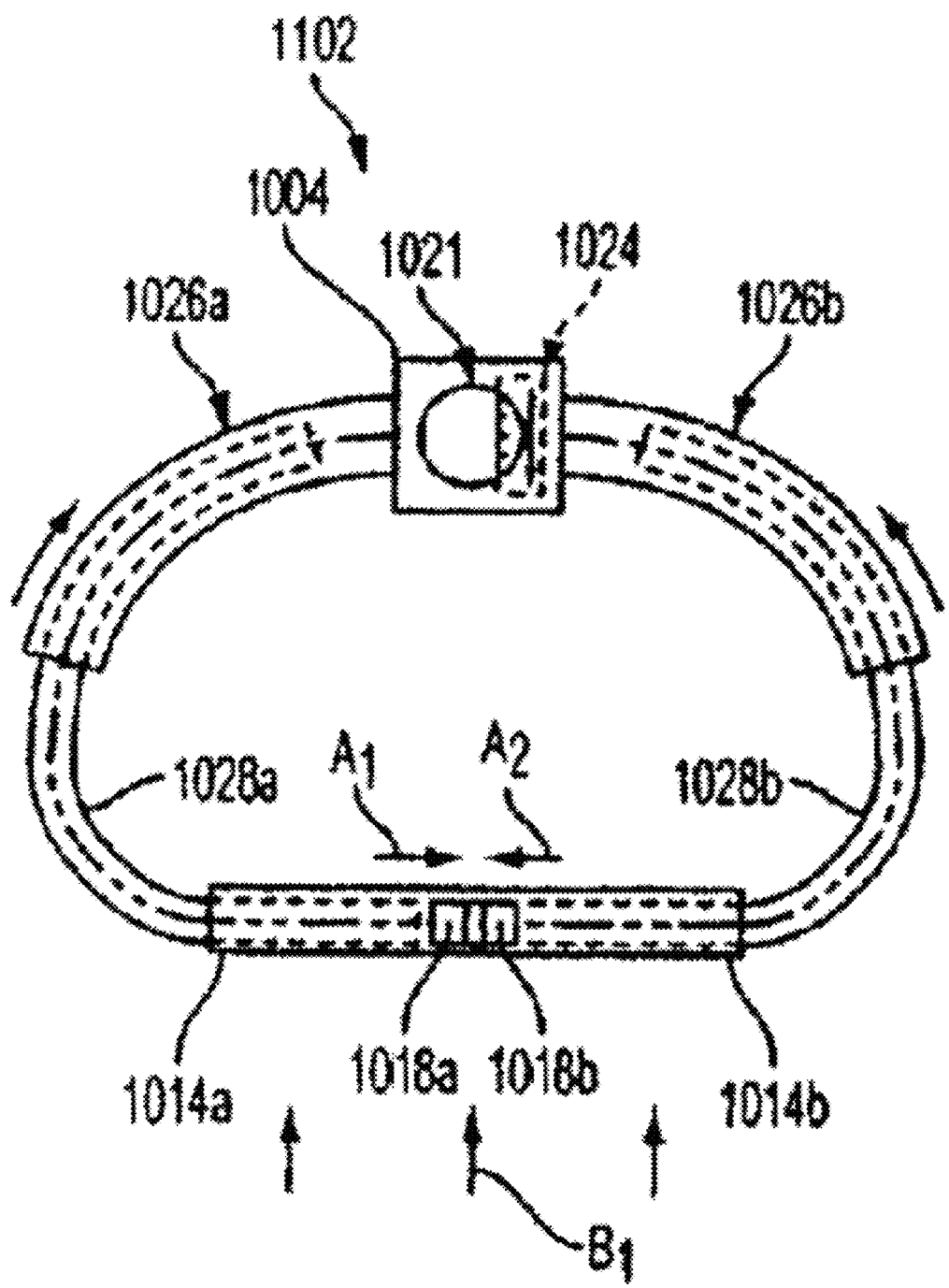
FIG. 32 is a front view of the implantable device of FIG. 31 having the outer tubing and inner tubing in a relative second position.
Figure 33:
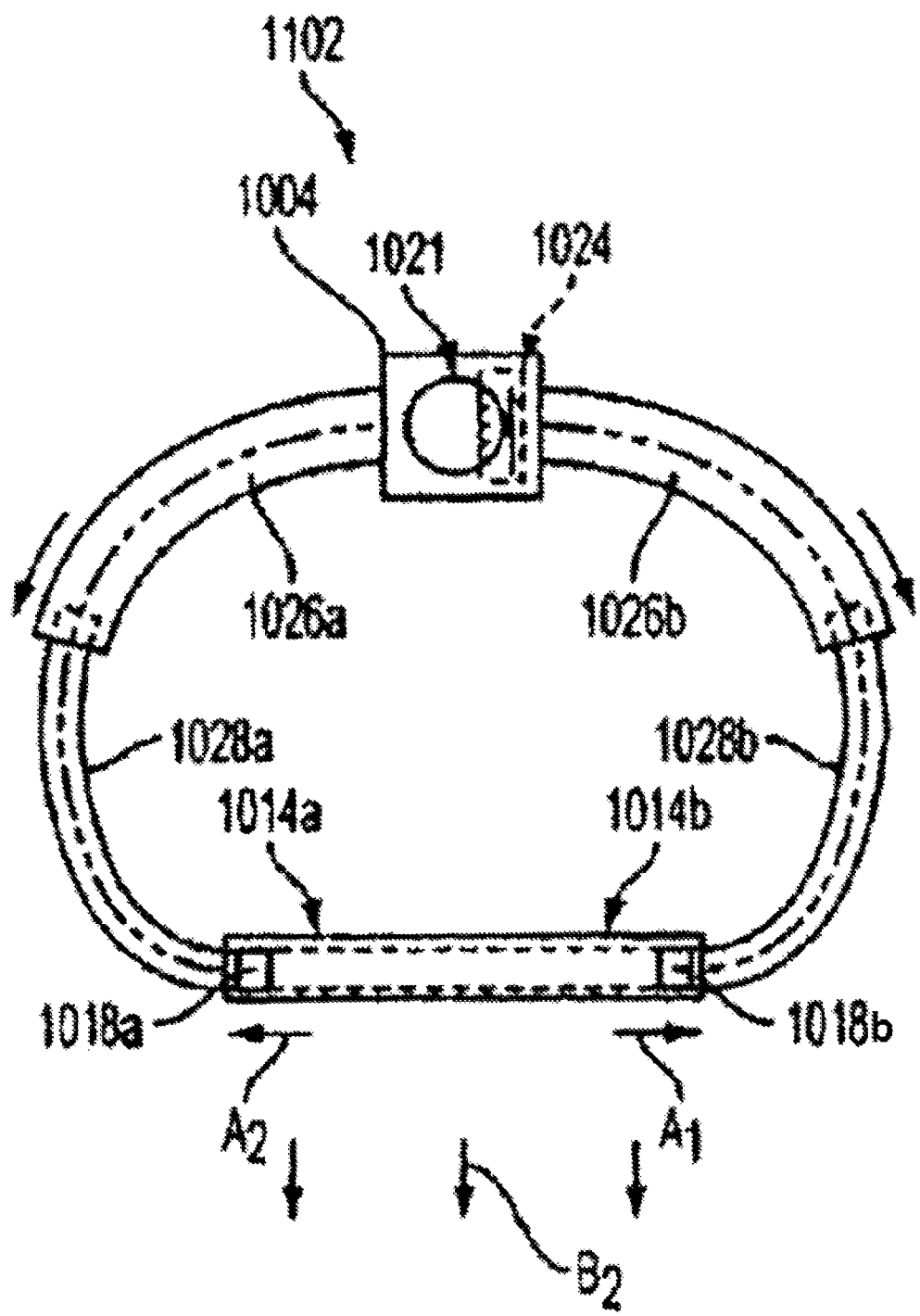
FIG. 33 is a front view of the implantable device of FIG. 31 having the outer tubing and inner tubing in a relative third position.
Figure 34:
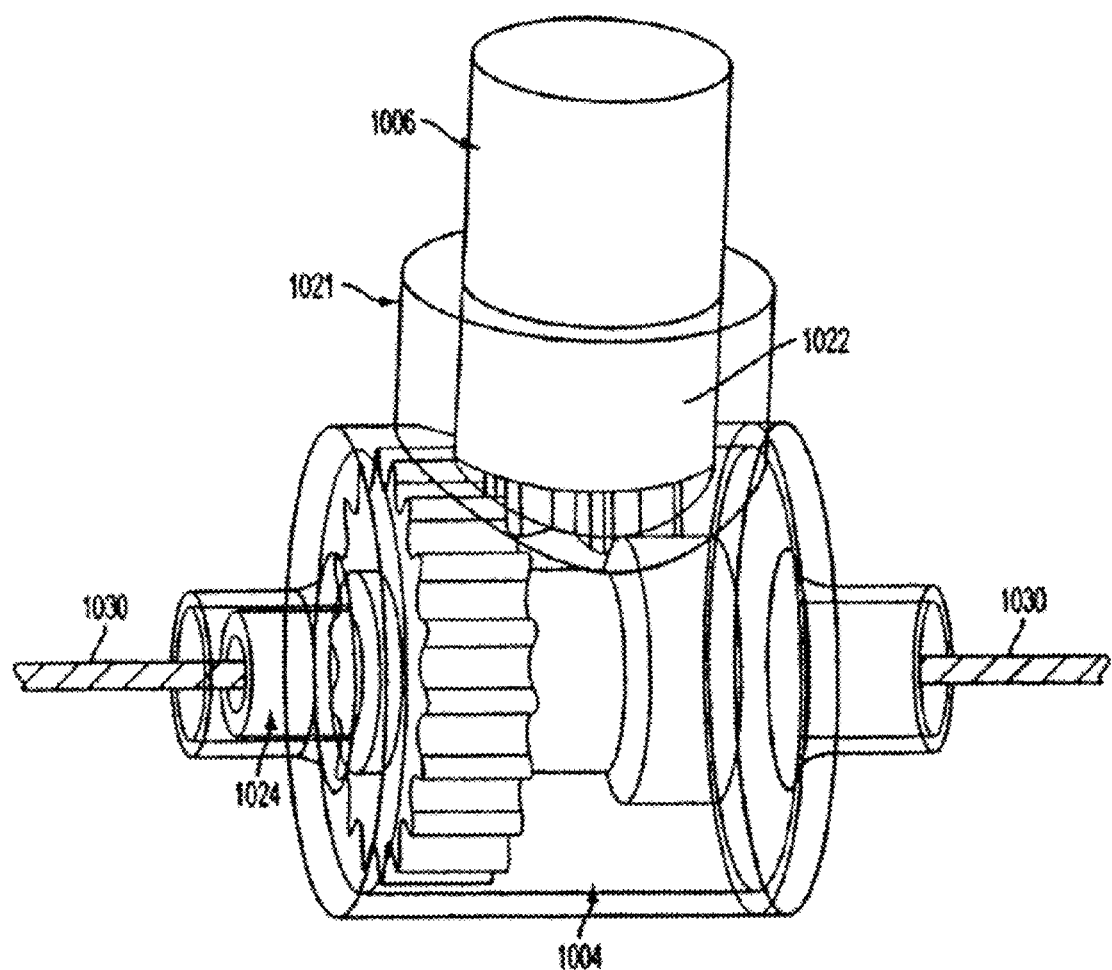
FIG. 34 is a schematic view of an embodiment of an adjustment mechanism showing the interior thereof, with the distal tip of an adjustment tool coupled to an adjustment mechanism.
Figure 35:
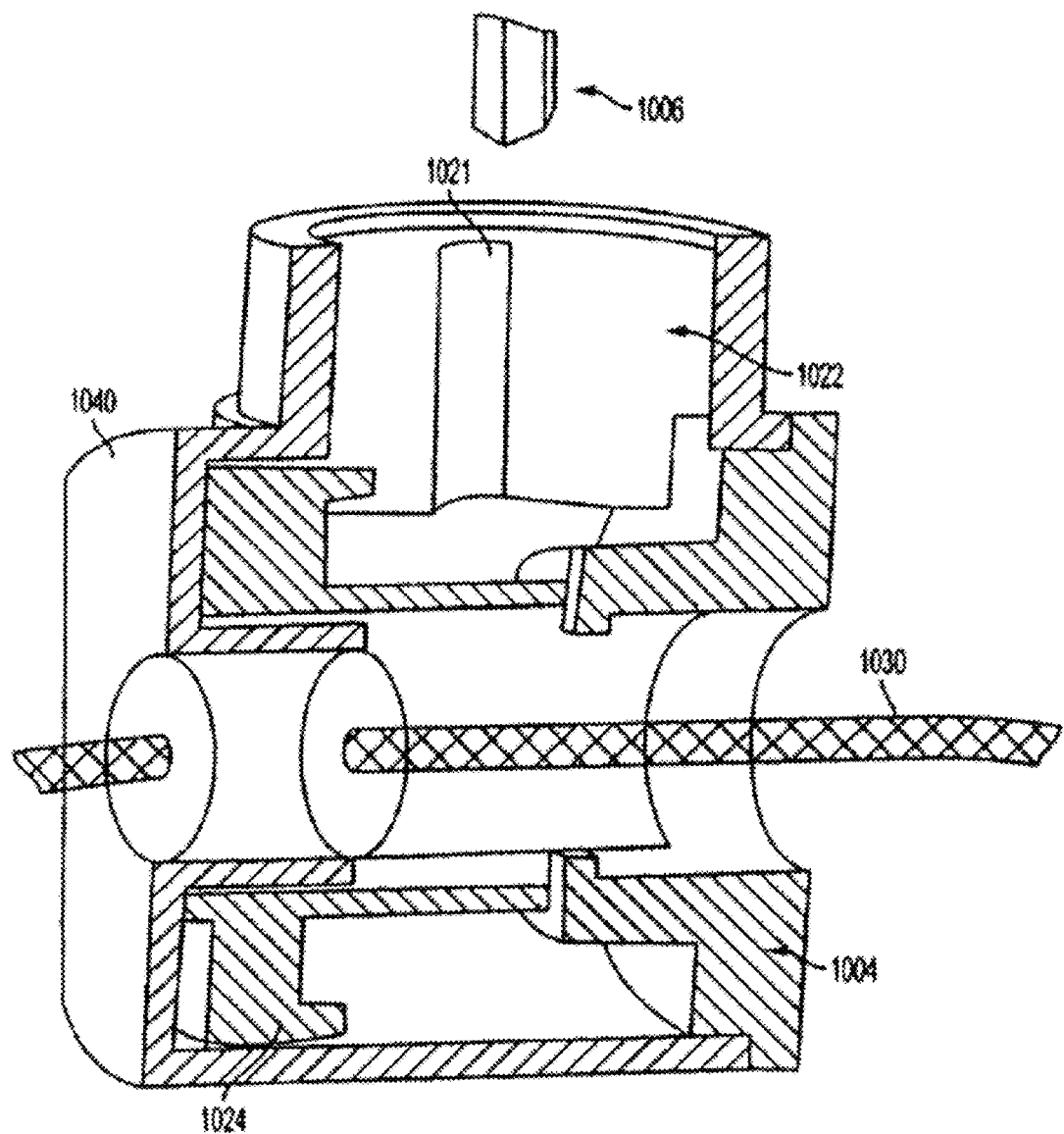
FIG. 35 is a schematic cross-sectional view of the adjustment mechanism of FIG. 34.

In another embodiment of the present disclosure, illustrated in FIGS. 31 through 35, the adjustment mechanism 1004 provides translated motion through rotation. FIGS. 31 through 33 illustrate a theory of operation of an embodiment of the present disclosure, while FIGS. 34 and 35 show details of the adjustment mechanism 1004.

Referring to now FIG. 31, adjustment mechanism 1004 of implantable device 1102 is shown including a docking port 1021 to receive the distal tip of the adjustment tool 1006 (FIG. 29). In this embodiment, implantable device 1102 includes a set of inner tubing 1028a, 1028b and a set of outer tubing 1026a, 1026b that can move relative to each other. The ends of the inner tubing 1028a, 1028b that do not engage the outer tubing 1026a, 1026b are secured to a set of hollow tubing 1014a, 1014b so that the inner tubing 1028a, 1028b does not move relative to the hollow tubing 1014a, 1014b. Although hollow tubing 1014a, 1014b may be separate pieces that are permanently abutted when assembled, in some embodiments, the hollow tubing 1014a, 1014b may be formed from a single tubing piece. An inner cable 1030 passes through the various tubing. Thus, the rigidity of the hollow tubing can be used to maintain the shape of implantable device 1102 in certain dimensions so that adjustment of the device can be restricted to a preferred dimension, for example, an anterior-posterior dimension.

As shown in more detail in FIGS. 34 and 35, adjustment mechanism 1004 may include a pinion gear 1022 (which may be integral to docking port 1021) and a crown gear 1024. FIG. 34 provides an isometric view of the adjustment mechanism 1004, and FIG. 35 provides a cut-away view of the adjustment mechanism 1004. As can be seen in the figures, the pinion gear 1022 engages the crown gear 1024. In some embodiments, the pinion gear 1022 may be eliminated from adjustment mechanism 1004, and the distal tip of the adjustment tool 1006 may serve as the pinion gear when the tool is coupled to the docking port 1021. When coupled to the docking port 1021, the adjustment tool 1006 can rotate the pinion gear 1022.

Referring back to FIG. 31, the implantable device 1102 is shown generally at the middle of its adjustment range. Outer tubing 1026*a*, 1026*b* is affixed to the adjustment mechanism 1004 and extends along a portion of the circumference of implantable device 1102. Inner tubing 1028*a*, 1028*b* is affixed to hollow tubing 1014*a*, 1014*b*, respectively. Similar to the single threaded rod 1008 of FIG. 30B, threaded rods 1018*a*, 1018*b* sit inside the hollow tubing 1014*a*, 1014*b* and are threadedly engaged therewith. Threaded rods 1018*a*, 1018*b* may be a rigid material such as titanium, stainless steel, or a polymer. Hollow tube portions 1014*a*, 1014*b* enclose the threaded rods 1018*a*, 1018*b* such that rotation of the threaded rods 1018*a*, 1018*b* causes them to move axially within the hollow tube portions 1014*a*, 1014*b*. The threaded rod 1018*a* may have right-handed threads, and the threaded rod 1018*b* may have left handed threads. Other embodiments may include threaded rods 1018*a*, 1018*b* with threads in a single direction (e.g., all right-hand threads or all left-hand threads).

The crown gear 1024, and one end of each threaded rod 1018*a*, 1018*b* are all attached to an inner cable 1030. Inner cable 1030 may be a cable or tube of any material with sufficient flexibility to conform to the shape of the implantable device 1102 while translating torque. For example, suitable material for inner cable 1030 may include titanium or stainless steel. As shown more clearly in FIGS. 34 and 35, the rotation of crown gear 1024 imparts rotation to cable 1030 in the same direction.

Referring to FIG. 32, when the handle of adjustment tool 1006 (not shown in this figure) is rotated clockwise in docking port 1021, it causes clockwise rotation of the pinion gear 1022 (in FIG. 34). Rotation of the pinion gear 1022 in turn rotates crown gear 1024. The rotation of crown gear 1024 causes rotation of inner cable 1030, which imparts rotational movement to each threaded rod 1018*a*, 1018*b*. The rotation applied to the threaded rods 1018*a*, 1018*b* causes them to advance into their respective hollow tubing 1014*a*, 1014*b* in the directions A1, A2 shown. As shown in FIG. 32, when threaded rods 1018*a*, 1018*b* advance toward the middle of the hollow tubing 1014*a*, 1014*b*, the overall circumference of the implantable device 1002 is reduced. Advancing the threaded rods 1018*a*, 1018*b* drives the inner cable 1030 into the hollow tubing 1014*a*, 1014*b*. Translation of inner cable 1030 into the hollow tubing 1014*a*, 1014*b* causes the hollow tubing 1014*a*, 1014*b* to move towards adjustment mechanism 1004 in the direction B1 shown. Inner tubing 1028*a*, 1028*b* slides into outer tubing 1026*a*, 1026*b* to accommodate movement of the inner cable 1030.

Referring to FIG. 33, the handle of adjustment tool 1006 (not shown in this figure) is rotated counter-clockwise in docking port 1021 to cause counter-clockwise rotation of the pinion gear 1022 (FIG. 34). Rotation of the pinion gear 1022 in turn rotates crown gear 1024. The rotation of crown gear 1024 causes rotation of inner cable 1030, which imparts rotational movement to each threaded rod 1018*a*, 1018*b*. The rotation applied to the threaded rods 1018*a*, 1018*b* causes them to begin to withdraw from their respective hollow tubing 1014*a*, 1014*b* in the directions A2, A1 shown.

As shown in FIG. 33, as threaded rods 1018*a*, 1018*b* withdraw from the middle of the hollow tubing 1014*a*, 1014*b*, the overall circumference of the implantable device 1002 is increased. Withdrawal of the threaded rods 1018*a*, 1018*b* pushes the inner cable 1030 out of the hollow tubing 1014*a*, 1014*b*. Translation of inner cable 1030 out of the hollow tubing 1014*a*, 1014*b* causes the hollow tubing 1014*a*, 1014*b* to move away from adjustment mechanism 1004 in the direction B2 shown. Inner tubing 1028*a*, 1028*b* telescopes out of outer tubing 1026*a*, 1026*b* to accommodate movement of the inner cable 1030.

Figure 36:
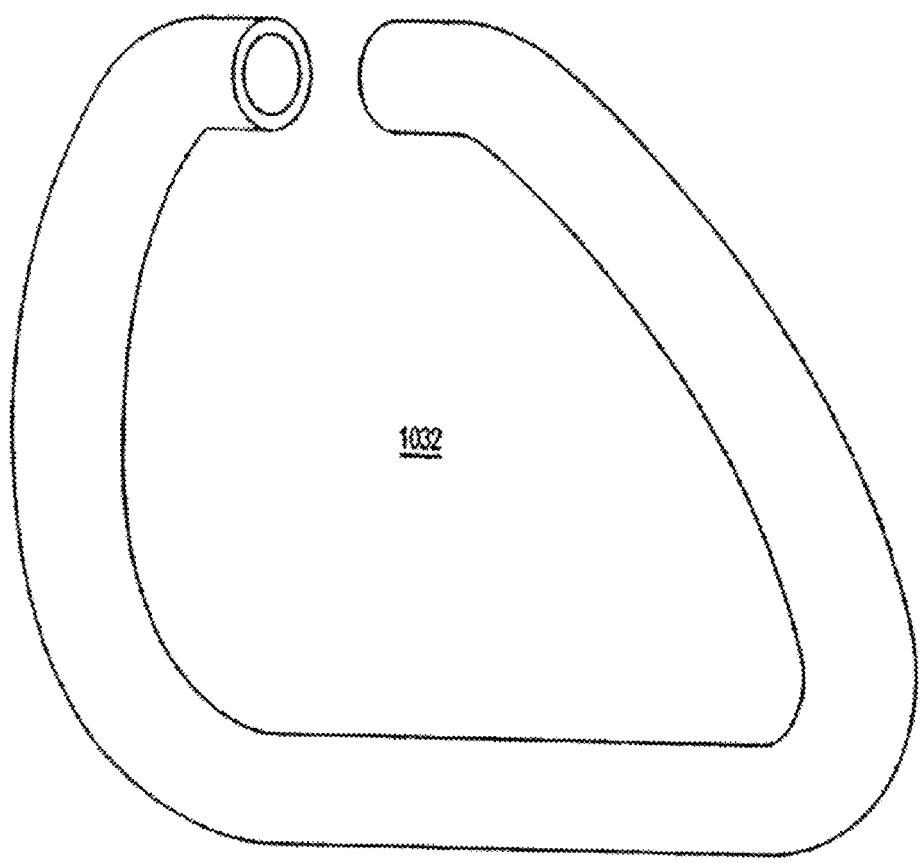
FIG. 36 is a perspective view of an embodiment of a flexible tube cover for an implant device.

The inner tubing 1028*a*, 1028*b*, the outer tubing 1026*a*, 1026*b*, and the hollow tubing 1014*a*, 1014*b* may be covered by a flexible tube 1032, such as a silicone tube, shown in FIG. 36. In one embodiment, outer flexible tube 1032 is provided with no seam in the axial direction of the tube to allow for better tissue ingrowth after the implant procedure. In other embodiments inner tubing 1028*a*, 1028*b* may be eliminated, as shown in FIG. 37.

Figure 37:
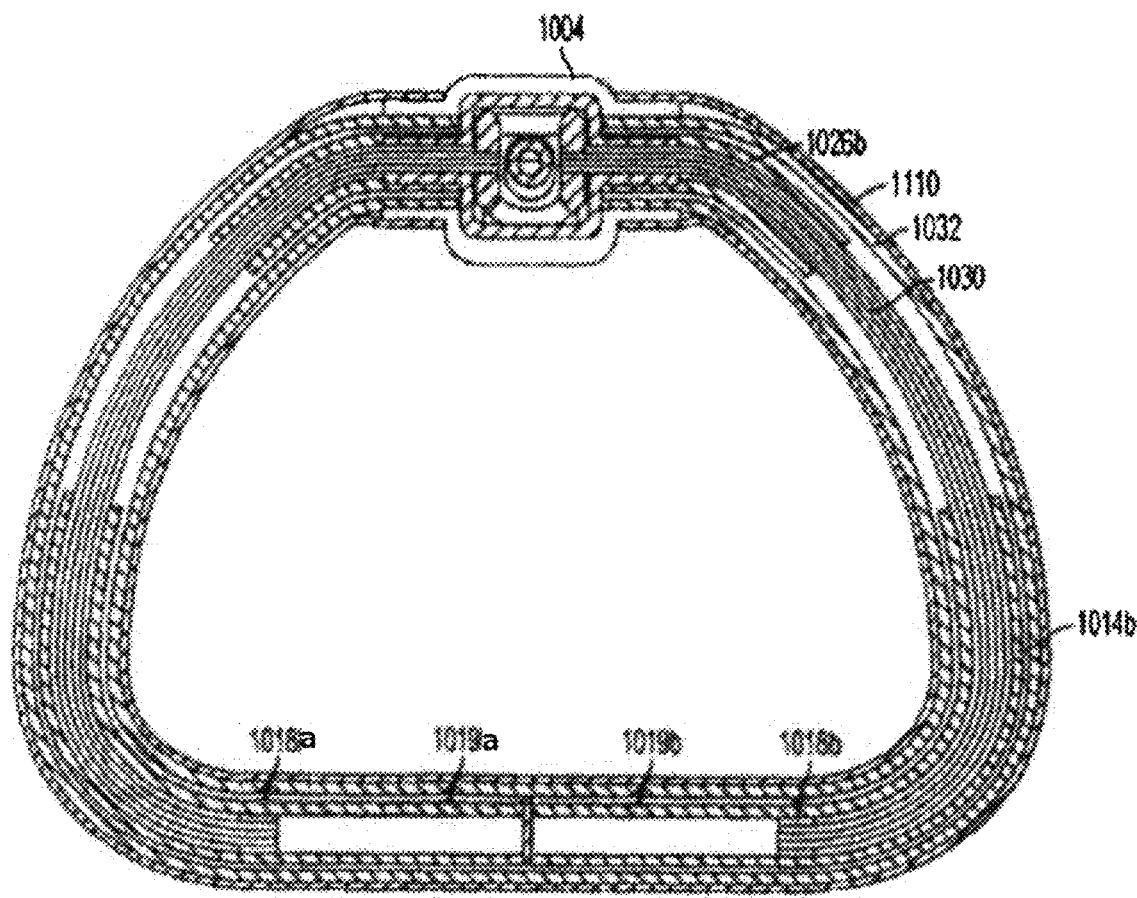
FIG. 37 is a cross-sectional view of an assembled embodiment of an adjustable implant device.

FIG. 37 provides an assembled cross-sectional view of an implantable device 1202 according to an embodiment of the disclosure. The implantable device includes the adjustment mechanism 1004, the outer tubing 1026*a*, 1026*b*, the hollow tubing 1014*a*, 1014*b*, the inner cable 1030, and the threaded rods 1018*a*, 1018*b* as discussed in relation to FIGS. 31-33. As shown in FIG. 37, hollow tubing 1014*a*, 1014*b* may extend further along the length of inner cable 1030 than shown in the embodiment of FIGS. 31-33 to better maintain a preferred shape of the implant. Hollow tubing 1014*a*, 1014*b* may be threaded to receive the threaded rods 1018*a*, 1018*b*, or hollow tubing 1014*a*, 1014*b* may optionally include a threaded insert (spar 1019*a*, 1019*b*) affixed to the inner diameter of hollow tubing 1014*a*, 1014*b*. In operation, as previously described, an adjustment tool may impart motion to the adjustment mechanism 1004. Gears in the adjustment mechanism translate motion to the inner cable 1030 that, in turn, translate motion to the attached threaded rods 1018*a*, 1018*b*. Depending on the direction of rotation, the rotation of threaded rods 1018*a*, 1018*b* causes the threaded rods 1018*a*, 1018*b* to be drawn toward or away from the middle of the hollow tubing 1014*a*, 1014*b*, thus reducing or increasing the overall circumference of the implantable device 1002. The flexible outer tube 1032 and a seal jacket 1100 (also shown in FIG. 38) encapsulate the device so that no moving parts are exposed. The flexible outer tube 1032 provides sufficient rigidity to maintain a generally planar dimension, while allowing the device to adjust shape generally in a preferred dimension, such as the anterior-posterior dimension. As shown in FIG. 37, the flexible outer tube 1032 may be further covered by an outer fabric sheath 1110 or thin sewing cuff. Elimination of the inner tubing (1028*a*, 1028*b* of FIG. 33) eliminates the need for telescoping parts and prevents the possibility of telescoping tubes being sutured or clipped together during attachment of the implant.

Figure 38:
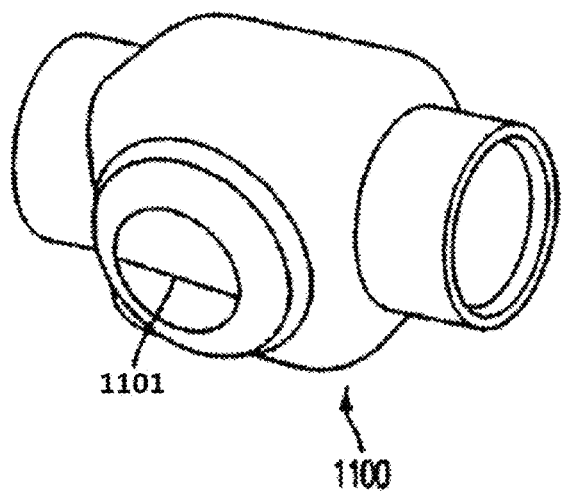
FIG. 38 is an enlarged perspective view of an embodiment of a seal jacket for an adjustment mechanism.

Referring to FIG. 38, the adjustment mechanism 1004 can include a seal jacket 1100. FIG. 38 shows an embodiment of the seal jacket 1100. The seal jacket 1100 may include a cover 1101 for the docking port 1021 (FIG. 31) of the adjustment mechanism 1004. The cover 1101 may be in the form of a slit septum, flaps, elastic material or the like. The seal jacket cover 1101 may be included as part of a seal jacket 1100 that covers the entire housing of the adjustment mechanism 1004 or a separate piece. In one embodiment, the seal jacket 1100 may be secured to the flexible tube 1032. The seal jacket 1100 and flexible tube 1032 may be secured by an adhesive bond, a wrap, sutures, or the like. The cover 1101 provides access for an adjustment tool to couple to the docking port, while reducing the possibility of thrombus. In some embodiments, seal jacket cover 1101 and/or the seal jacket 1100 may be made of silicone, and covered by a polyester sewing layer or fabric sheath (e.g., 1110 of FIG. 37). In various embodiments, the seal jacket fits over the housing of an adjustment mechanism 1004 that includes a crown gear coupled to a cable, can provide pinion access, and the like. In operation, the distal tip of an adjustment tool passes through the cover 1101 to engage the rotatable gear of adjustment mechanism 1004.

Figure 39:
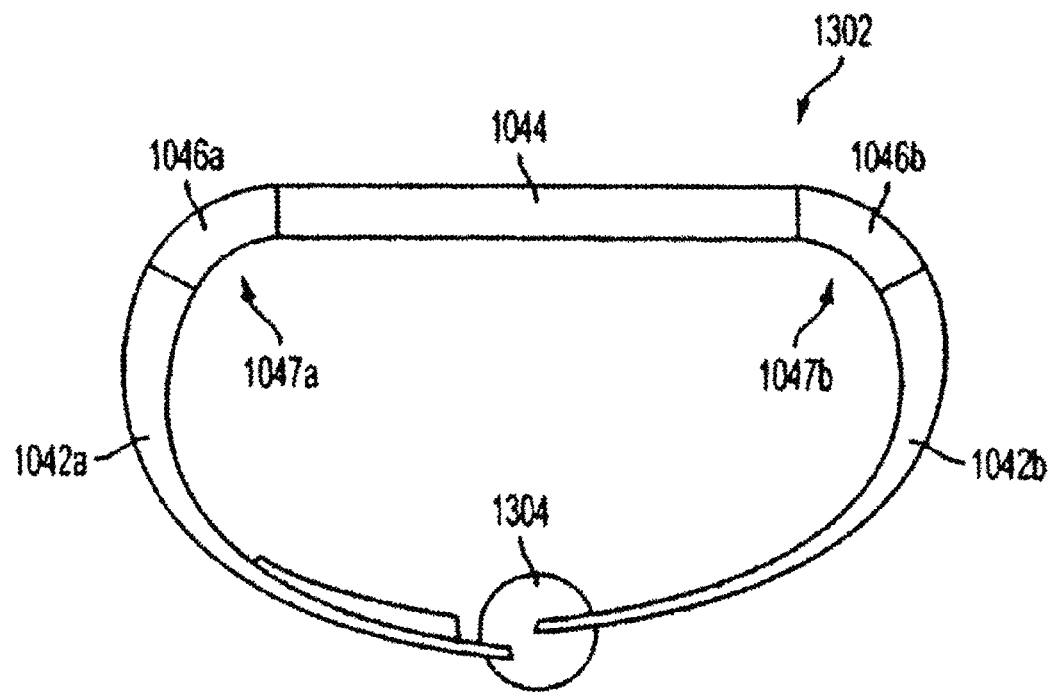
FIG. 39 is a schematic view of an embodiment of an adjustment band and an adjustment mechanism in an implantable device of the present disclosure.

FIG. 39 shows an embodiment of implantable device 1302 including a first adjustment band 1042a and a second adjustment band 1042b. The first and second adjustment bands 1042a, 1042b can be overlapped, and the amount of overlap is affected by how the implantable device 1302 is sized. The first and second bands 1042a, 1042b can be slidable relative to each other. An adjustment mechanism 1304 is coupled to the first band 1042a and the second band 1042b, and pulls or pushes them toward or away from each other. The first band 1042a and the second band 1042b can have flexible portions 1046a, 1046b configured to create a flexible zone at the primary bend regions 1047a, 1047b. The flexible portions 1046a, 1046b can have varying lengths and may also include one or more rigid portions 1044. These rigid portions 1044 can include welded braids or bands, or have a higher durometer material than the flexible portions 1046a, 1046b. The flexible portions 1046a, 1046b and rigid portions 1044 may be part of the same material as the first and second bands 1042a, 1042b, or one or more portions may be separate material that is joined to form a continuous piece.

The first and second bands 1042a, 1042b can have different sizes or the same size. In one specific embodiment, the first and second bands 1042a, 1042b are about 0.5 to about 3 mm in thickness and about 5 to about 10 mm in width. The first and second bands 1042a, 1042b can be made of a variety of materials including, but not limited to, an SMA, an SMP, titanium, stainless steel, polymer, a suture-based material, a biological material and the like. In one embodiment, the first and second bands 1042a, 1042b include a plurality of band layers. At least a portion of the first and second bands 1042a, 1042b may have superelastic properties. Implantable device 1302 may include a flexible, extruded outer layer (not shown) or hollow tube, such as flexible tube 1032 of FIG. 36, to encase the structure formed by the first and second bands 1042a, 1042b flexible portions 1046a, 1046b, and rigid portions 1044. The parts of the first and second bands 1042a, 1042b that extend past adjustment mechanism 1304 can be contained within the hollow interior of the outer layer.

Figure 40:
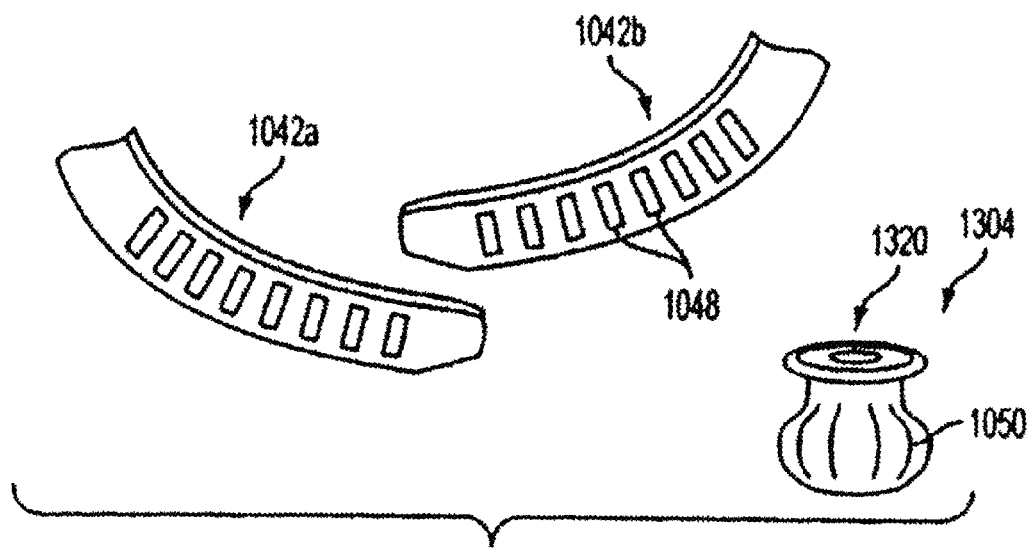
FIG. 40 is an enlarged disassembled view of part of the adjustment band and adjustment mechanism of FIG. 39.

FIG. 40 provides a more detailed schematic view of the unassembled adjustment bands and adjustment mechanism of FIG. 39. The first and second bands 1042a, 1042b may include a series of adjustment stops 1048. Adjustment stops 1048 may be in the form of holes, detents, dimples, ridges, teeth, raised elements, other mechanical features or the like. These holes 1048 on each of the bands 1042a, 1042b are coupled to adjustment mechanism 1304. The adjustment mechanism 1304 may be generally cylindrical (such as a spool) with a series of teeth 1050 or protrusions radially positioned to engage the adjustment stops 1048. Adjustment mechanism 1304 may also include a docking port 1320 to receive an adjustment tool to trigger rotational movement of the adjustment mechanism.

Figure 41:
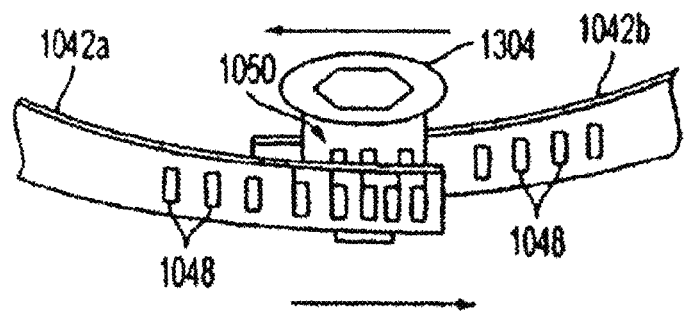
FIG. 41 is an enlarged assembled view of the adjustment band and adjustment mechanism of FIG. 39.

FIG. 41 provides an assembled view of the adjustment bands and adjustment mechanism of FIG. 40. When mounted in a housing (not shown in FIG. 41), the adjustment mechanism 1304 may be mounted on an axis to allow for rotational movement. The first and second bands 1042a, 1042b pass on either side of adjustment mechanism 1304 so that the teeth 1050 engage the adjustment stops 1048 in each of the bands 1042a, 1042b. Rotating the adjustment mechanism in turn tightens or loosens the bands.

Figure 42:
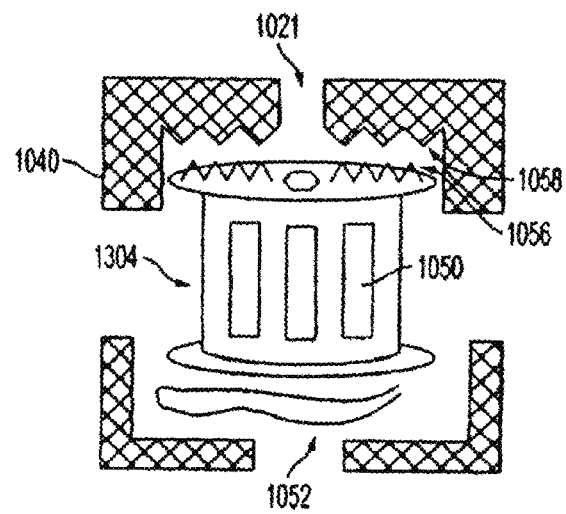
FIG. 42 is an enlarged cut-away schematic view of an embodiment of the gearbox for the adjustment band of FIG. 39.

FIG. 42 is a cut-away view of an embodiment of the gearbox for the adjustment band of FIG. 39. In this embodiment, the adjustment mechanism 1304 rests on a spring 1052 inside a housing 1040 for the adjustment mechanism. The housing 1040 includes access and guidance for the first and second bands (1042a, 1042b of FIG. 41) to couple with the teeth 1050 of the adjustment mechanism 1304. The spring 1052 forces the adjustment mechanism 1304 upward so that teeth 1056 on the top of the adjustment mechanism 1304 engage with teeth 1058 on the inside upper surface of the housing 1040. Engagement of the adjustment mechanism teeth 1056 with the housing teeth 1058 locks the adjustment mechanism 1304 in place to prevent rotational movement. Downward force, applied for example by an adjustment tool, against the spring 1052 disengages the teeth 1056 and 1058 so that the adjustment mechanism 1304 can be rotated to adjust the size or shape of implantable device 1302.

Figure 43:
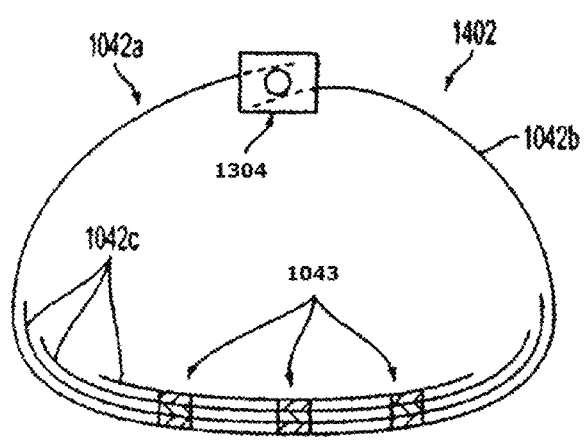
FIG. 43 is a schematic view of an embodiment of an implantable device with a sliding band that can be opened and closed to effect a preferential shape change.

In another embodiment, FIG. 43 provides a schematic view of an implantable device 1402 of the present disclosure with a plurality of sliding bands that can be opened and closed to effect a shape change. As with the previous embodiments of FIGS. 39-42, the first and second bands 1042a, 1042b pass on either side of adjustment mechanism 1304 so that the teeth 1050 engage the adjustment stops 1048 in each of the bands 1042a, 1042b. Additional bands 1042c may be incorporated to increase the stiffness at different areas of the implantable device 1402 to provide preferential shape change. The additional bands 1042c may be secured to the first and second bands 1042a, 1042b using welds 1043, adhesive or other mechanical techniques known in the art.

Figure 44:
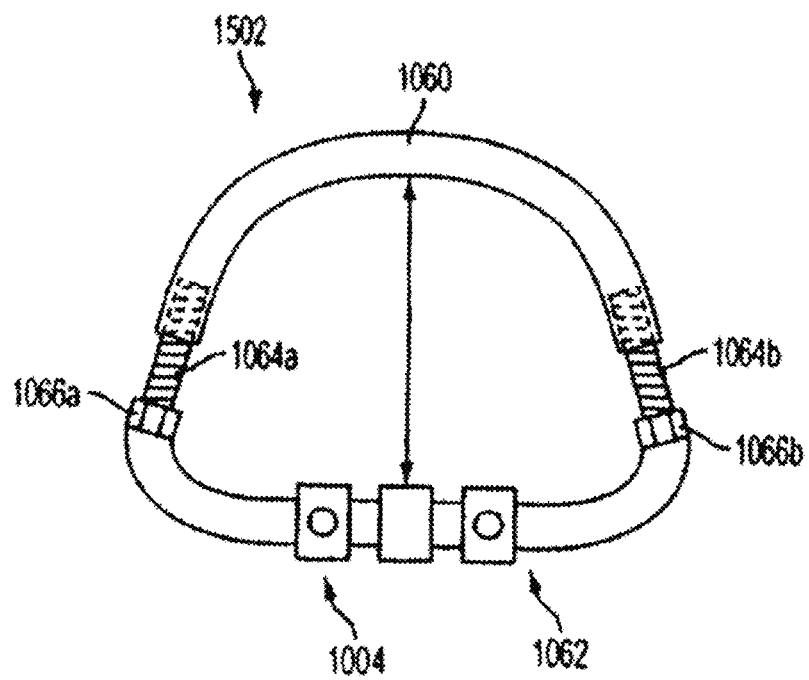
FIG. 44 is a front view of an alternate embodiment of the implantable device of the present disclosure with two adjustable screws used to achieve different pulling rates.

As illustrated in FIG. 44, in another embodiment, an implantable device 1502 has an anterior portion 1060, a posterior portion 1062 and dual threads that provide preferential adjustment of one side or the other of implantable device 1502. The implantable device 1502 has two independently adjustable threaded portions 1064a, 1064b used to achieve different pulling rates and/or lateral dimensions. The adjustable threaded portions 1064a, 1064b can be connected to one or more adjustment mechanisms 1004 of the implantable device 1502 and positioned at either the posterior or anterior portions of the implantable device 1502. In one embodiment, the posterior portion 1062 may be a rigid member which includes threaded hex screws 1066a, 1066b, internal threads or similar structures. In one embodiment, the hex screws 1066a, 1066b are attached in a manner that allows rotation of the hex screws so that the threads may engage adjustable threaded portions 1064a, 1064b. Rigid posterior portion 1062 may include one or more adjustment mechanisms 1004 that can receive a tool to impart rotational motion through an inner tube or cable to one or more of hex screws 1066a, 1066b, as described above. Anterior portion 1060 may be a flexible tube to accommodate shape change as the anterior and posterior portions 1060, 1062 move relative to each other.

In another embodiment, differently pitched threads or other mechanisms may be used to provide non-symmetrical shape change of the implant device. For example, referring to FIG. 44, wider threads on threaded portion 1064b, in relation to the threads of threaded portion 1064a, would allow an adjustment mechanism 1004 to expand or contract the implantable device 1502 more rapidly on the side of threaded portion 1064b to provide preferential shape change for a selected region while using a single adjustment mechanism.

Figure 45:
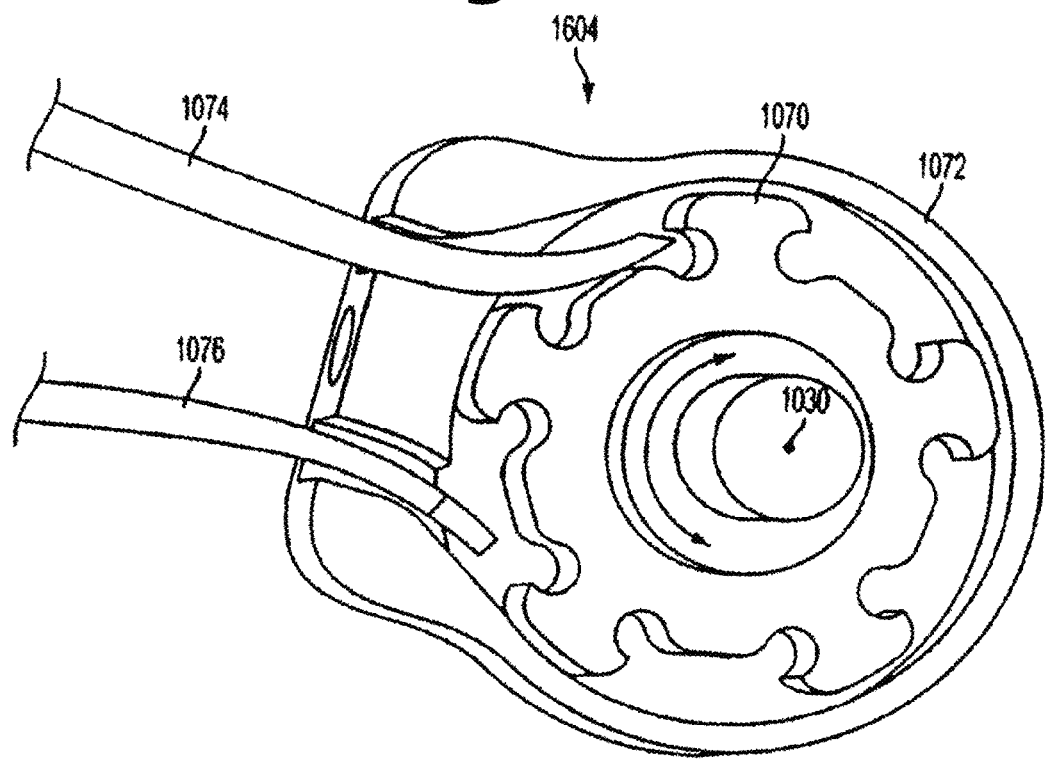
FIG. 45 is an enlarged perspective view of an embodiment of the implantable device of the present disclosure with the cover removed to illustrate reciprocating motion and a clover gear.

FIG. 45 is a schematic view of an embodiment of an adjustment mechanism 1604 for an implantable device. An adjustment tool may impart reciprocating motion to the adjustment mechanism 1604 that includes a clover gear 1070 mounted in a housing 1072. The inner cable 1030 (FIG. 31) of the implantable device, for example, is affixed to the clover gear 1070 such that rotation of the clover gear transmits torque through the inner cable 1030 to a screw or other adjustable portion of the implantable device as previously disclosed. In this embodiment, the adjustment tool can provide reciprocating action to provide for adjustment. The adjustment mechanism takes an axial force applied to the control portion at the proximal end of the adjustment tool and converts it to a rotational force applied to the inner cable 1030 of the implantable device. Reciprocating axial force may be provided from an adjustment tool by using spring-mounted buttons pressed by the user. Pressing a first button may transmit a downward axial motion to a first ribbon 1074 which engages the clover gear 1070 to cause clockwise rotation of the clover gear 1070. A spring or other return force pushes the first ribbon back to its original position after each click or press of the button. Similarly, pressing a second button may transmit a downward axial motion to a second ribbon 1076 that engages the clover gear 1070 to cause counter-clockwise rotation of the clover gear 1070.

In another embodiment, the adjustment tool provides coarse adjustment and fine adjustment. This varied adjustment can be achieved with the adjustment tool having screws with different threads.

Figure 46:
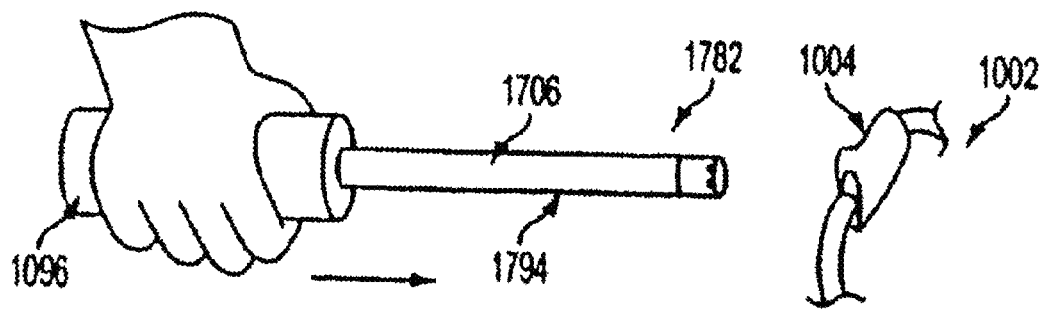
FIG. 46 is a schematic partial view of an embodiment of an implantable device system of the present disclosure with an adjustment tool having high column strength and stiffness.

FIG. 46 provides a schematic view of an embodiment of the implantable device system 1000 including an adjustment tool 1706 with high column strength and stiffness. The adjustment tool 1706 has a shaft 1794 and a handle 1096 with sufficient column strength to ensure a downward axial force on the handle 1096 provides proper engagement with the adjustment mechanism 1004 of the implantable device 1002. The handle 1096 may be a grip-like handle, as shown, or a smaller pen-type handle. The adjustment tool 1706 can include mechanical locking at the distal region 1782 to lock with the adjustment mechanism 1004. The mechanical locking is configured to provide engagement and disengagement tactile feel to the physician.

Figure 47:
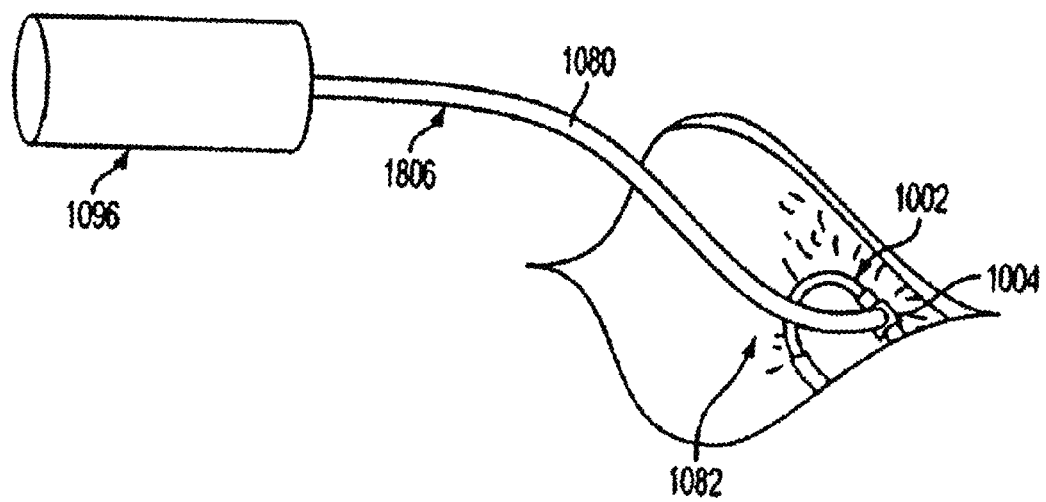
FIG. 47 is a schematic view of an embodiment of the implantable device of the present disclosure shown in vivo with an adjustment tool having reduced column stiffness.

FIG. 47 is a schematic view of another embodiment of the implantable device system 1000 including an adjustment tool 1806 with reduced column stiffness. The adjustment tool 1806 has a handle 1096 and a shaft 1080 with reduced column stiffness for greater flexibility and easier articulation of the adjustment tool 1806. The handle 1096 may be a grip-like handle, as shown, or a smaller pen-type handle. The easier articulation offered by this embodiment may facilitate user positioning of the device in vivo and clearing adjacent biological structures, particularly when it is docked to the adjustment mechanism 1004 of the implantable device 1002. Flexibility may be varied along the length of the adjustment tool shaft 1080. Flexibility may be increased at the distal region 1082 of the adjustment tool shaft 1080, particularly in the region immediately proximal to the gear/fitting at the distal tip of the adjustment tool 1806. This gear/fitting is constrained orthogonally to the adjustment mechanism 1004, and it is important that the adjustment tool 1806 be easy to insert/connect and remain clear of biological structures.

Figure 48:
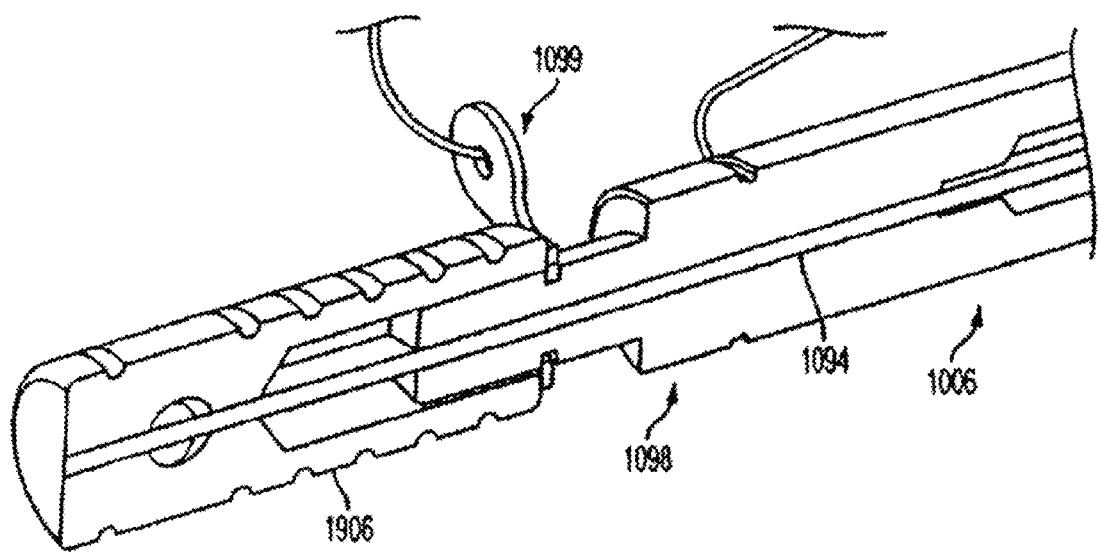
FIG. 48 is a partial cut-away view of an embodiment of the proximal portion of an adjustment tool.

FIG. 48 provides a cut-away view of an embodiment of the proximal end of the adjustment tool 1006. Referring to FIG. 48, adjustment tool 1006 includes a flexible cable 1094 or similar structure that is affixed to and rotates with a handle 1096. In other embodiments, the adjustment tool 1006 can have cables, a band, tubes, rods, and the like to impart rotational and/or axial motion from the proximal end to the distal tip of the tool 1006. The flexible cable 1094 may be enclosed by a flexible, low-friction cable jacket 1098 that allows the cable 1094 to rotate freely within the jacket 1098. In some embodiments, adjustment tool 1006 may also include a spring release mechanism to allow disengagement of the distal tip of the tool from the docking port 1021 (FIG. 31) with minimal force being applied to the sutures (or other mechanisms) securing the implant device to the tissue of an anatomic orifice or lumen. As shown in FIG. 48, in some embodiments, an e-clip 1099 or similar device may be used near the handle 1096 of the adjustment tool 1006 to secure the release mechanism in the docking station until adjustments are complete.

Figure 49:
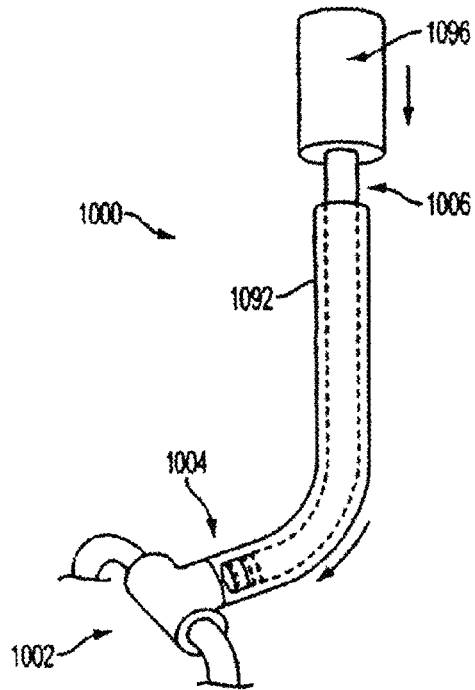
FIG. 49 is a partial view of another embodiment of an implantable device of the present disclosure with an articulated shape.

In one embodiment illustrated in FIG. 49, the adjustment tool 1006 may be inserted inside a rigid sheath 1092 that reaches the implantable device 1002. Thus, FIG. 49 is a partial view of an embodiment of the implantable device system 1000 of the present disclosure with an articulated shape. The rigidness of the sheath 1092 provides the necessary column strength to support the flexible adjustment tool 1006. An added benefit to this embodiment is that the sheath may be left in place, docked to the implantable device 1002. The flexible adjustment tool 1006 may be removed and then reinserted at some future time to engage with the adjustment mechanism 1004 of implantable device 1002.

The adjustment tool 1006 can have a handle 1096 that can be adjustable. The handle 1096 can have a length of at least 8 inches, and in one embodiment at least 10 inches. Other embodiments may have a shorter or longer handle length. The handle 1096 may be thick to provide a hand-grip, or, in other embodiments, smaller to provide a pen-like grip. The handle can have a device to quantify a size change of the implantable device 1002. For example, a half-turn of the adjustment tool handle can be correlated to a distance of travel of the threaded rods 1018a, 1018b (FIG. 31) of implantable device 1002, thus allowing for measured adjustment of the implant. The handle may include a click-counter or other known device to measure rotational movement. In one embodiment, the adjustment tool 1006 may be included in a percutaneous delivery catheter.

A sensor, such as the touchdown sensor described in relation to FIGS. 12-18 above, can be coupled to the implantable device 1002. A variety of different sensors can be utilized, including but not limited to, sensors that measure pressure, temperature and flow across the implantable device 1002. Pacing leads are coupled to the sensor and the implantable device 1002, and in this embodiment, the sensor is responsive to flow through the implantable device 1002.

In another embodiment, the implantable device system may include a micro-electromechanical motor system in conjunction with or instead of a separate adjustment tool to commence rotational movement in an adjustment mechanism. Power and control of the micro-electromechanical motor system can be provided by electromagnetic radiation or through a direct wire connection as previously described herein.

Figure 50:
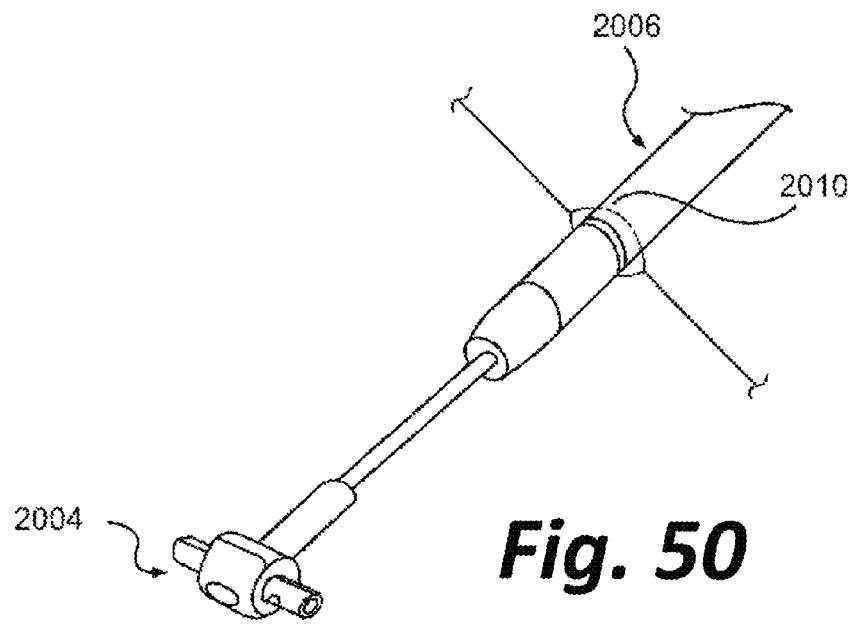
FIGS. 50-57 show one embodiment of an adjustment tool that can be reinserted into the body and reconnected to an adjustment mechanism so that additional adjustments to an implantable device can be made post-operatively.
Figure 51:
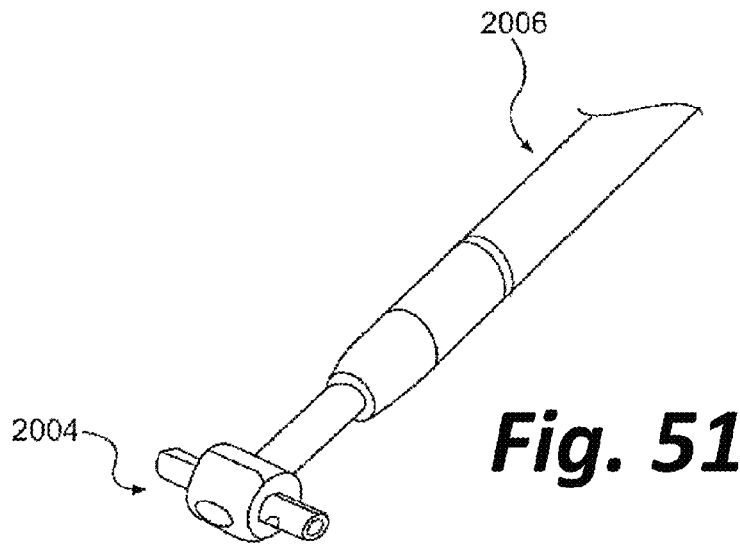

As discussed above, it is contemplated that the flexible adjustment tool may be removed and then reinserted at some future time to engage with the adjustment mechanism of an implantable device. FIGS. 50-57 show one embodiment of an adjustment tool 2006 that can be reinserted into the body and reconnected to an adjustment mechanism 2004 so that additional adjustments to the implantable device can be made post-operatively. More specifically, FIG. 50 shows the adjustment tool 2006 after it has been re-inserted into the left atrium, but before it has been reconnected to the adjustment mechanism 2004. In this example, the adjustment tool 2006 is re-inserted into the left atrium via a purse string suture 2010. This procedure can be performed using a purse string suture tensioning device. FIG. 51 shows the adjustment tool 2006 after it has been reconnected to the adjustment mechanism 2004.

Figure 52:
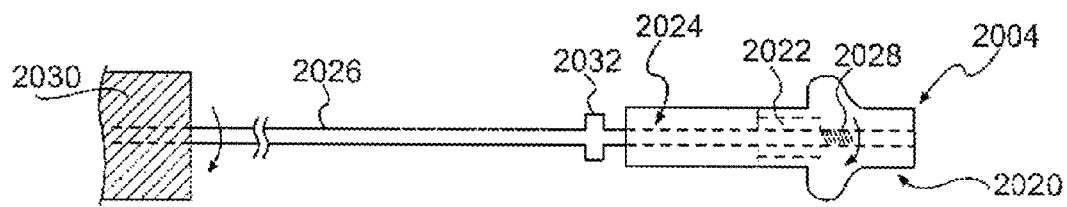
Figure 53:
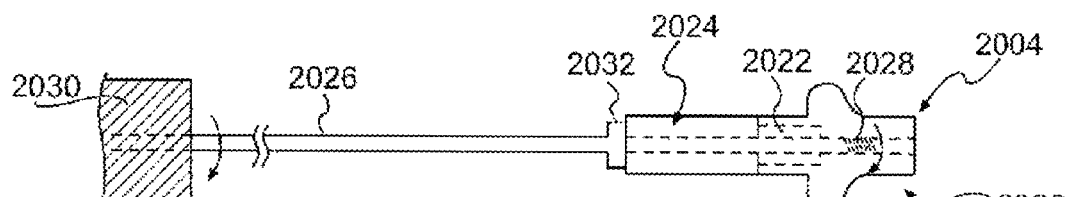
Figure 54:
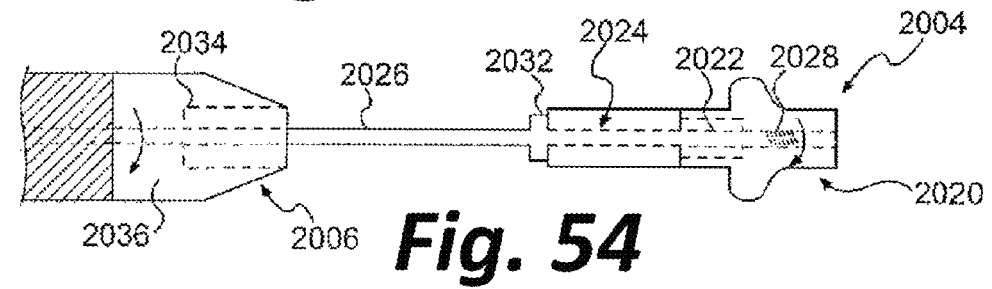

FIGS. 52-57 show the procedure for reconnecting the adjustment tool 2006 to the adjustment mechanism 2004 of the implantable device. FIG. 54 shows an adjustment mechanism 2004 with a gear 2020 that can be designed to control the size and/or shape of the implantable device, in accordance with any of the embodiments of the present disclosure previously described herein. The gear 2020 of the adjustment mechanism 2004 is functionally connected to a gear hex fitting 2022, which in turn is functionally connected to a shaft hex fitting 2024. In one embodiment, the shaft hex fitting 2024 is made of a rigid material that will allow it to effectively transmit torque to the gear 2020. After the implantable device has been attached to an anatomic orifice or lumen, both the gear hex fitting 2022 and the shaft hex fitting 2024 remain connected to the adjustment mechanism 2004 so that the adjustment tool 2006 can be reconnected to the adjustment mechanism 2004 at a later time. In order to post-operatively reconnect the adjustment tool 2006 to the adjustment mechanism 2004, first, a guidewire 2026 is inserted into the body and connected to the gear 2020 of the adjustment mechanism 2004 by rotating a threaded screw 2028 on the distal end of the guidewire 2026 using a knob component 2030 attached to the proximal end of the guidewire 2026, as shown in FIG. 52. The knob component 2030 and screw 2028 are rotated until a shoulder portion 2032 of the guidewire 2026 contacts the shaft hex fitting 2024, as shown in FIG. 53.

Figure 55:
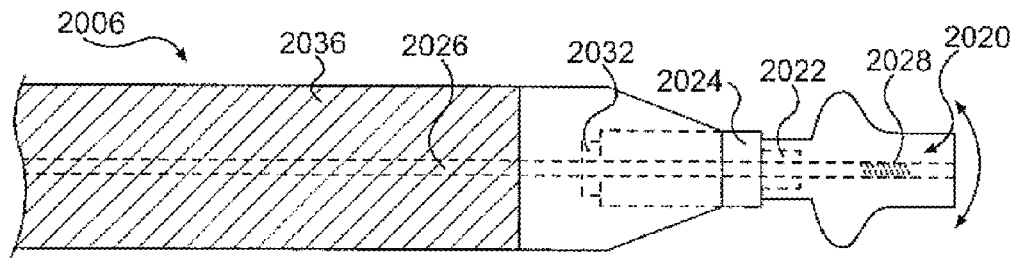
Figure 56:
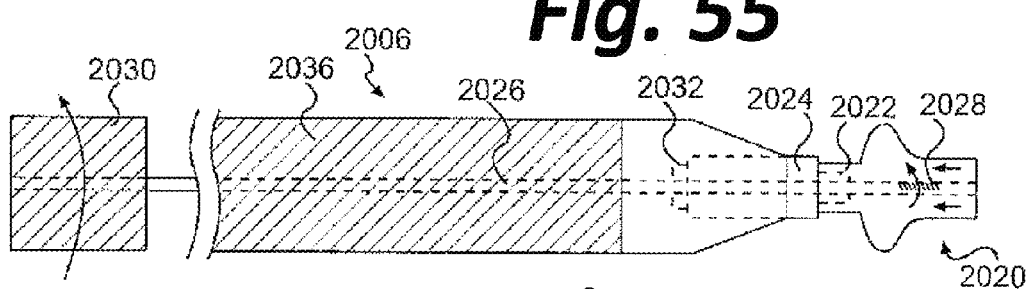
Figure 57:
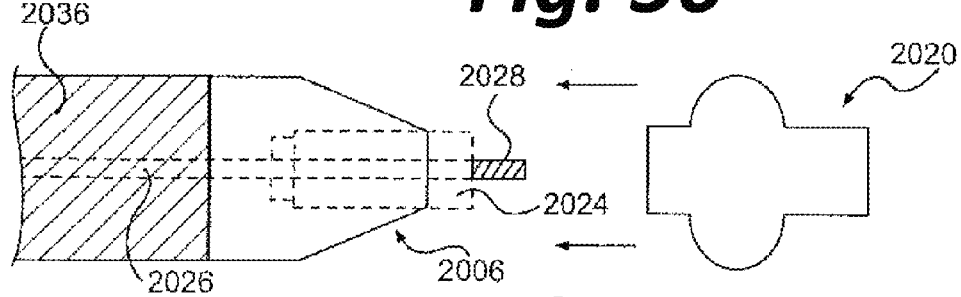

FIG. 54 shows the adjustment tool 2006 being reinserted along the guidewire 2026. The distal end of the adjustment tool 2006 includes a shaft hex tip 2034 with an internal hex that mates with shaft hex fitting 2024 connected to the adjustment mechanism 2004. Once the adjustment tool 2006 has been mated with the shaft hex fitting 2024, the shaft 2036 of the adjustment tool 2006 can be rotated in order to impart rotation to the shaft hex fitting 2024. As shown in FIG. 55, this will cause the gear 2020 to rotate, which will cause the implantable device to change shape and/or size, as was explained above with respect to embodiments of the implantable device. After the desired adjustment has been completed, the adjustment tool 2006 can be detached from the adjustment mechanism 2004 by rotating the knob component 2030 and unscrewing the guidewire 2026 from the gear 2020, as shown in FIG. 56. Finally, FIG. 57 shows that, after the guidewire 2026 has been unscrewed, the adjustment tool 2006, guidewire 2026, and shaft hex fitting 2024 can all be removed from the body.

Figure 58:
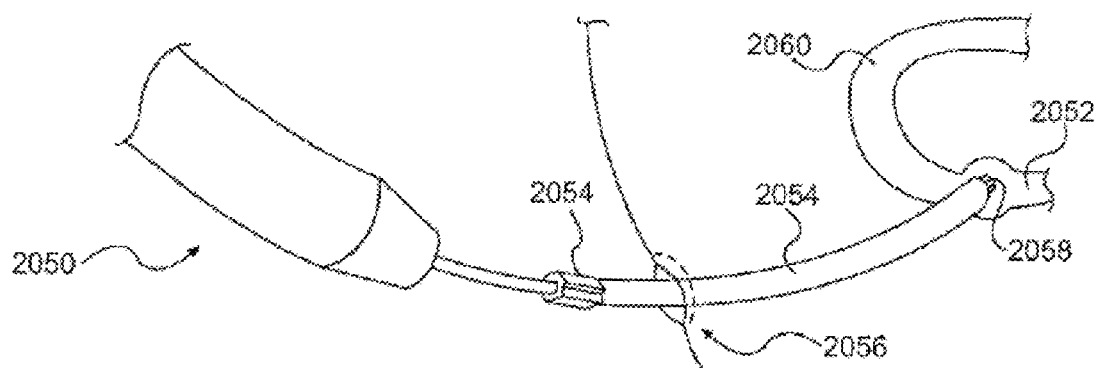
FIGS. 58-60 show a second embodiment of an adjustment tool that can be reinserted into the body and reconnected to an adjustment mechanism so that additional adjustments to an implantable device can be made post-operatively.
Figure 59:
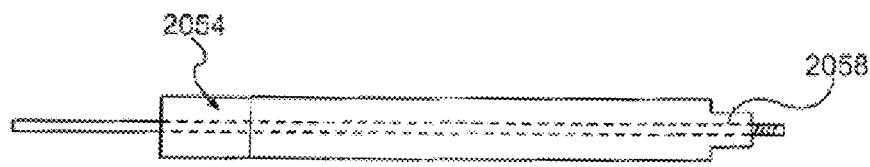
Figure 60:
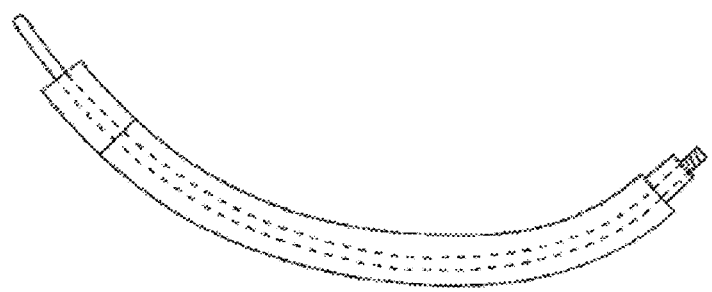

FIGS. 58-60 show a second embodiment of an adjustment tool 2050 that can be reinserted into the body and reconnected to an adjustment mechanism 2052 so that additional adjustments to the implantable device can be made post-operatively. In this embodiment, the shaft hex fitting 2054 is constructed so that it is long enough to extend through the purse string suture 2056. Similar to the previous embodiment, the shaft hex fitting 2054 and gear hex fitting 2058 are left in the body when the implantable device 2060 is attached to the anatomic orifice or lumen. The advantage of this embodiment is that, as shown in FIG. 58, it allows the adjustment tool 2050 to connect to the shaft hex fitting 2054 without having to be re-inserted through the purse string suture 2056. This is beneficial because it reduces the stress placed on the purse string suture during reconnection of the adjustment tool. The process for re-inserting and reconnecting the adjustment tool 2050 to the adjustment mechanism 2052 is similar to that discussed above with respect to FIGS. 52-57, with one difference being that the connection takes place outside the purse string suture 2056. Furthermore, because the shaft hex fitting 2054 is longer in this embodiment, it may need to be flexible (rather than rigid) to accommodate the anatomy of the heart, as shown in FIGS. 59-60.

As noted above, upon initial implantation of any of the prosthetic implants described above into a native orifice, such as the mitral valve, it is preferable that the native orifice is functioning as desired. While certain embodiments described above indicate diagnostic tools, including TEE, to determine the functioning of the orifice, a particularly suitable method of determining functioning is through microelectromechanical (MEM) sensors, for example, that sense pressure. As is described in greater detail below, the use of these sensors on or with any of the implants described above may provide significant benefits, including the ability to not only immediately determine implant effectiveness upon initial implantation and prior to completing the surgery, but further on an ongoing basis to track functioning over time. In addition, it would be beneficial to track patient cardiac health after device implantation. Exemplary sensors and implant systems incorporating the sensors are described in greater detail below.

Figure 61:
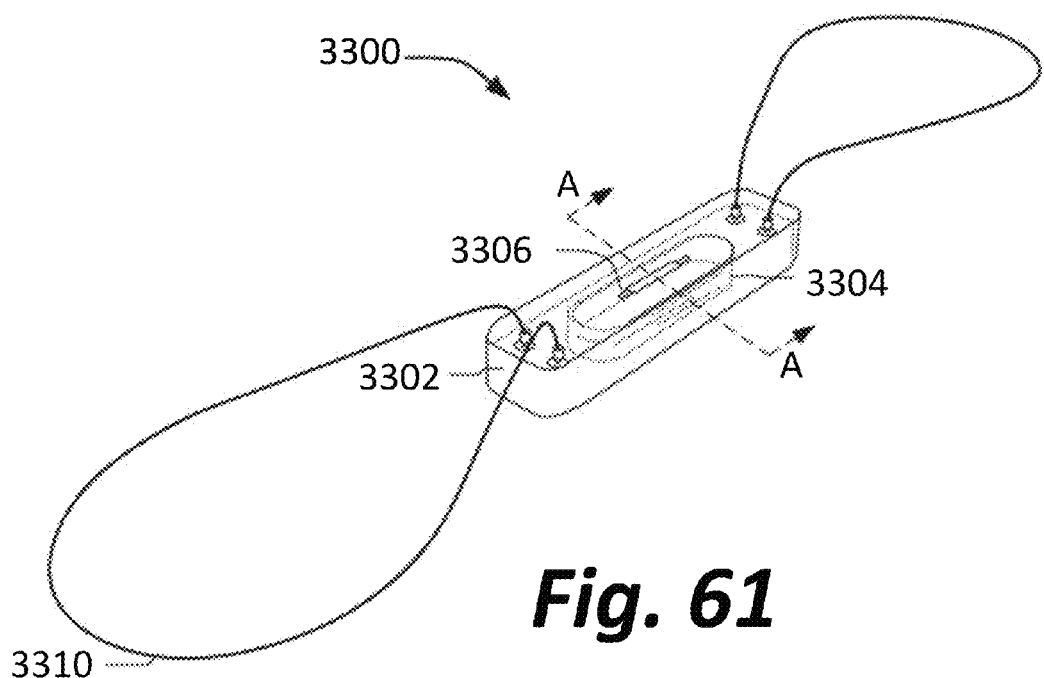
FIG. 61 is a perspective view of a microelectromechanical (MEM) sensor.
Figure 62:
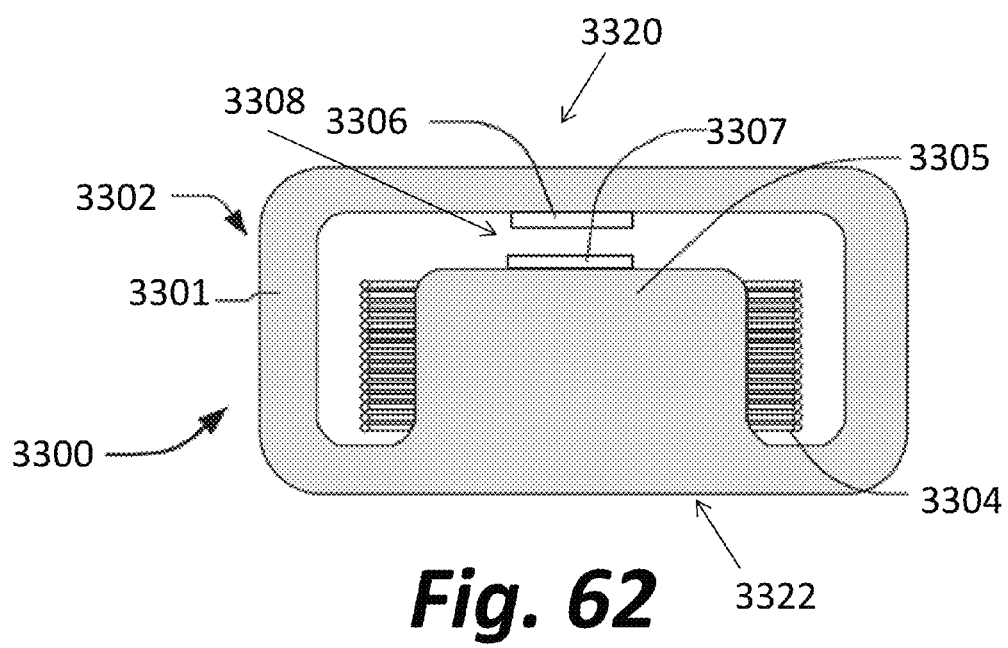
FIG. 62 is a cross-sectional view taken along line A-A of FIG. 61.

FIGS. 61 and 62 illustrate one example of a microelectromechanical (MEM) sensor for diagnostic usage. Sensor 3300 generally includes body 3302 formed of a generally hollow fused silica housing 3301. An elongated boss 3305, also formed from fused silica, may project into the interior of housing 3301 and may be formed integrally therewith. A plurality of electrically conductive windings may wrap around boss 3305 to form an inductor coil 3304. Capacitive plates 3306 and 3307 are separated by micrometer spacing, forming a variable capacitor 3308. The exterior of housing 3301 is coated with silicone, forming a hermetically sealed assembly that does not come in contact with blood.

Capacitive plate 3306 is sensitive to pressure and experiences nanometer scale deflections due to changes in blood pressure acting on the sensor 3300. In that regard, body 3302 includes an active face 3320 and a passive face 3322, the measurements being taken at the active face. The nanometer scale deflections of plate 3306 result in a change in the resonant frequency of the circuit formed by the inductor coil 3304 and the pressure-sensitive capacitor 3308. The resonant frequency is given by the equation:

$$\text{Resonant Frequency } f_R = \frac{1}{2\pi\sqrt{L \times C(p)}},$$

where L is the inductance of inductor coil 3304 and C(p) is the capacitance of capacitor 3308 which varies with pressure.

The sensor 3300 can be electromagnetically coupled to a transmitting/receiving antenna (not shown). As a current is induced in the sensor 3300, the sensor oscillates at the resonant frequency of the circuit formed by the inductor coil 3304 and capacitor 3308. This oscillation causes a change in the frequency spectrum of the transmitted signal. From this change, the bandwidth and resonant frequency of the particular sensor may be determined, and the corresponding blood pressure can then be calculated. Time-resolved blood pressure measurements can be correlated to flow using empirical relationships established in clinical literature. In one example, an external device may interrogate sensor 3300 when in close proximity and may be placed near a location in which a patient is often located, such as in a pillow or in or near a bed. The external device may store data and have software for interpreting and/or displaying data, or may be used in conjunction with another device having software for interpreting and/or displaying data. Apparatus and methods for determining sensed data, such as blood pressure or data correlating to blood pressure, are discussed in greater detail in U.S. Pat. No. 6,855,115, the contents of which are hereby incorporated by reference herein.

As shown, sensor 3300 includes optional Nitinol loops 3310 extending from each end of body 3302 to stabilize the sensor at an implant location. It will be appreciated that sensor 3300 includes no additional leads, batteries, or active-fixation mechanisms. Sensor 3300 is an externally modulated inductor-capacitor circuit, which is powered using radio frequency by the antenna. Additionally, sensor 3300 may be relatively small (e.g., 3.5×2×15 mm). Other advantages of sensor 3300 include its accuracy, durability, biocompatibility, and insensitivity to changes in body chemistry, temperature, or biology. Sensor 3300 may optionally include one or more radiopaque components to aid in localization and imaging of the device.

Sensor 3300 may be modified for various applications and tuned to selectively emphasize different parameters. For example, by varying the width of the windings of inductor coil 3304, the number of turns and the size of a gap between adjacent upper and lower windings, the resonant frequency that the device operates at and the pressure sensitivity (i.e., the change in frequency as a result of deflection of capacitor plate 3306) can be optimized for different applications. In general, the design allows for a very small gap between the capacitor plates (typically between about 0.5 and about 35 microns) that, in turn, provides a high degree of sensitivity while requiring only a minute movement of the capacitive plates 3306 and 3307 to sense pressure changes.

The thickness of sensor 3300 may also be varied to alter mechanical properties. Thicker substrates for forming housing 3301 are more durable for manufacturing. Thinner substrates allow for the creation of thin pressure sensitive membranes for added sensitivity. In order to optimize both properties, sensor 3300 may be manufactured using two complementary substrates of different thicknesses. For example, one side of sensor 3300 may be constructed from a substrate having a thickness of about 200 microns. This provides the ability to develop and tune the sensor based on the operational environment in which the implanted sensor 3300 is implanted. In addition to changes to housing 3301, other modifications may be made to the sensor depending on the application. For example, nitinol loops 3310 may be omitted and replaced with suture holes for attaching the sensor to a support, and cantilevers or other structural members may be added. In some variations, the sensors may be powered by kinetic motion, the body's heat pump, glucose, electron flow, Quantum Dot Energy, and similar techniques.

Sensors 3300 may be used to measure one or more parameters including real time blood pressure; flow velocity (e.g., blood flow); apposition forces based on pressure changes due to interaction between two surfaces of the prosthetic valve; impingement forces, which are correlated to pressure changes caused by the interaction between a surface of the prosthetic device and native tissue; cardiac output; effective orifice area; pressure drop; temperature; motion; and aortic regurgitation. Sensor 3300 provides time-resolved pressure data which may be correlated to the parameters of interest based on empirical correlations that have been presented in literature. In some examples, sensors 3300 may function similarly to piezo-electric strain gauges to directly measure a parameter. Other parameters may be indirectly calculated. One specific method of using sensors 3300 to measure aortic regurgitation will be described in greater detail below. Certain sensors and applications for sensors are described in greater detail in U.S. Patent Application No. 62/038,512 titled "Prosthetic Heart Devices Having Diagnostic Capabilities," the disclosure of which is hereby incorporated by reference herein.

It may be desirable to use one or more sensors 3300 with different implantable devices, including any of the prosthetic implants described above, such as implantable devices 10, 100, 645, 700, 800, 1002, 1102, 1202, 1302, 1402, or 1502. In particular, it may be desirable to be able to "bolt on" one or more sensors similar to sensor 3300 to a pre-existing implantable device. However, different implantable devices may provide for different challenges in achieving easy and effective attachment of sensors. To that end, the housing 3301 of sensor 3300 may be modified to facilitate easy and effective attachment of the sensor to a pre-existing implantable device. In embodiments of the disclosure described below, sensors coupled to implantable devices may remain in the body as long as desired, including for the life of the implantable device, so that blood pressure or other data may be taken as long as desired.

Figure 63:
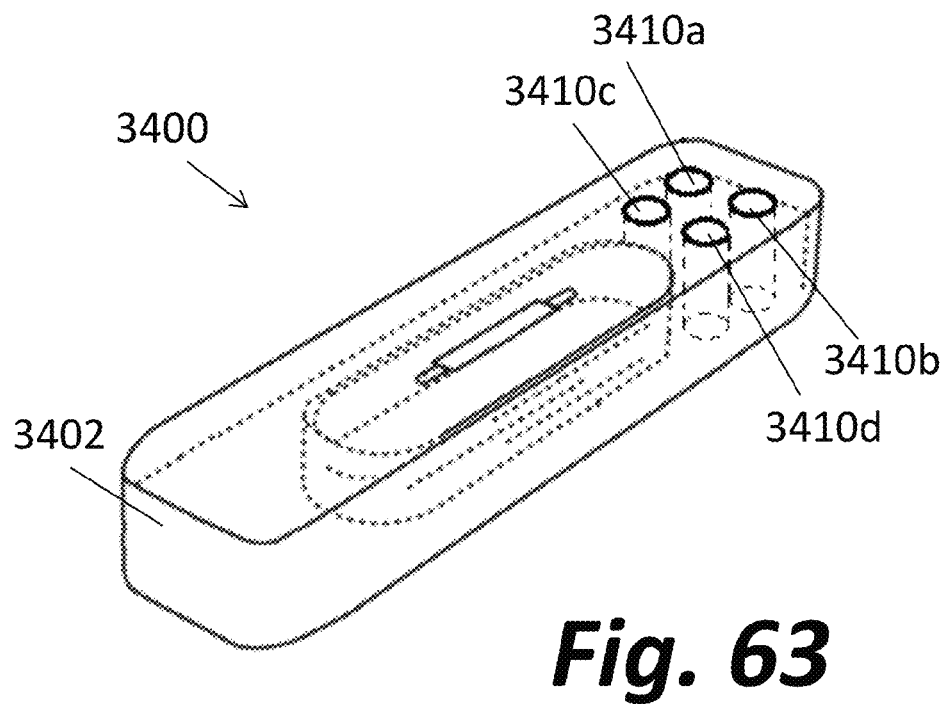
FIG. 63 is a perspective view of a wireless MEM sensor according to one embodiment of the disclosure.
Figure 64:
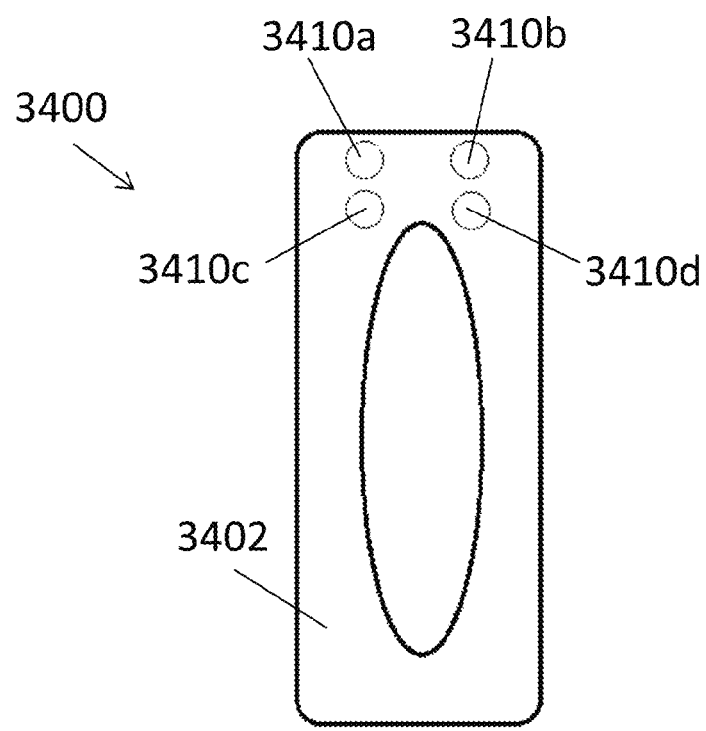
FIG. 64 is a plan view of the sensor of FIG. 63.

One example of a modified MEM sensor 3400 is shown in FIGS. 63-64. Sensor 3400 may be identical to sensor 3300 with certain exceptions. For example, sensor 3400 includes a different attachment mechanism than sensor 3300. Instead of having the Nitinol loops 3310 of sensor 3300, the body 3402 of sensor 3400 may include a plurality of through holes or apertures extending from a front surface of the body to a rear surface of the body. In particular, body 3402 may include four apertures 3410a-d provided in a generally rectangular configuration at one end of body 3402. Apertures 3410a-d may all be positioned a spaced longitudinal distance from functional components of sensor 3400, such as any capacitive plates or windings within body 3402. Apertures 3410a and 3410b may be positioned along a first plane extending transversely through body 3402, and apertures 3410c and 3410d may be positioned along a second plane extending transversely through body 3402. Similarly, apertures 3410a and 3410c may be positioned along a first plane extending longitudinally through body 3402, and apertures 3410b and 3410d may be positioned along a second plane extending longitudinally through body 3402. Apertures 3410a-d may be used to attach sensor 3400 to a device, such as implantable device 1102, with the use of attachment means such as sutures, described in greater detail below. Sensor 3400 may also be provided with rounded corners to minimize the chance of a sharp edge of sensor 3400 damaging any portion of the implantable device to which it is attached or the anatomy adjacent the implantable device.

Figure 65:
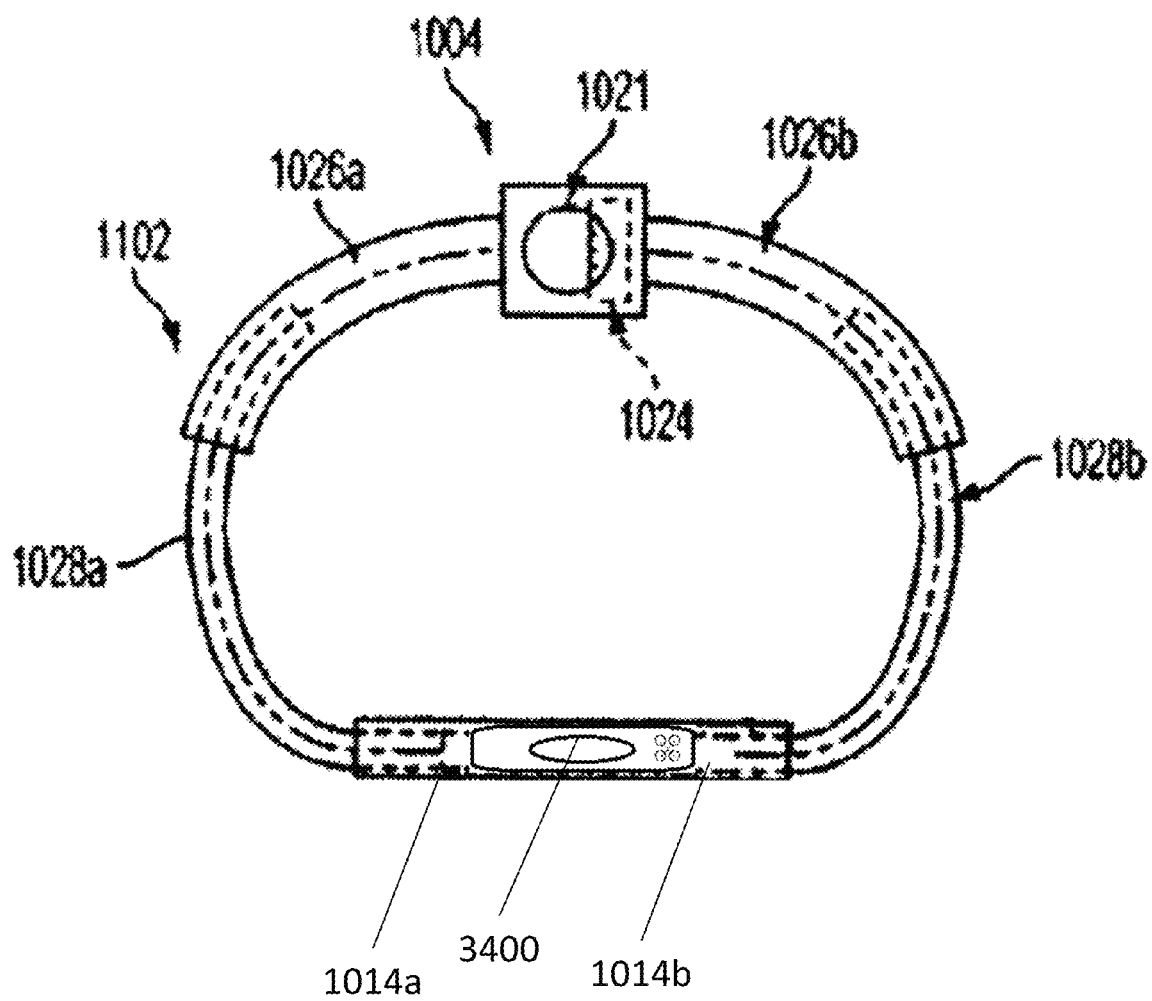
FIG. 65 is a front view of the implantable device of FIG. 31 with a sensor attached thereto.

FIG. 65 illustrates implantable device 1102 with sensor 3400 attached thereto. In particular, sensor 3400 is coupled to hollow tubing 1014a, 1014b. In one example, sutures are used to couple sensor 3400 to hollow tubing 1014a, 1014b via apertures 3410a-d. It should be understood that other methods of attachment, for example via stapling or adhesives, may be suitable. It should also be understood that other suitable combinations of apertures may be provided on sensor 3400 to provide any desired attachment locations, for example one aperture extending through each corner of body 3402. When implantable device 1102 is used as an annuloplasty ring in the mitral valve, for example, it is preferable that sensor 3400 is coupled to hollow tubing 1014a, 1014b so that, upon implantation of implantable device 1102 onto the mitral valve annulus, sensor 3400 is exposed to the left atrium to sense blood pressure in the left atrium. When sensor 3400 is in the position shown on implantable device 1102 and implanted into the native mitral valve, sensor 3400 may be referred to as an inflow sensor. It should be noted that, for implantable device 1102, connection to hollow tubing 1014a, 1014b may be preferred because, even during adjustment of the size of implantable device 1102, hollow tubing 1014a, 1014b undergoes little or no change in size or position because of its rigidity and its structural relation to other components of implantable device 1102. In addition, when attaching sensor 3400 to hollow tubing 1014a, 1014b with sutures, the sutures may pass directly through the hollow tubing, or additional material, such as a fabric covering, may be provided on the hollow tubing to facilitate the suturing.

Although physiological relevant data, such as pressure in the left atrium over time or flow across a single sensor, may be gained from the use of a single sensor on implantable device 1102, the use of two or more sensors coupled to implantable device 1102 may provide for additional physiological data. A pair of sensors may be positioned with respect to implantable device 1102 so that one sensor is exposed to the left atrium and one sensor is exposed to the left ventricle, allowing a pressure differential between the left atrium and left ventricle to be determined.

Figure 66:
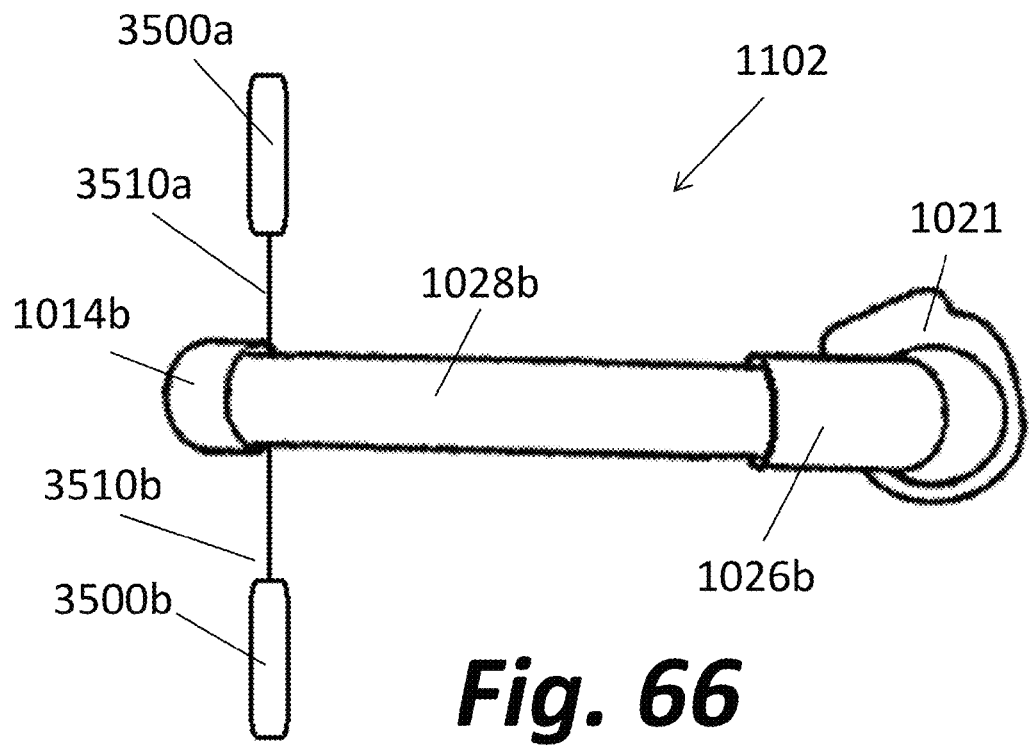
FIG. 66 is a side view of the implantable device of FIG. 31 with a pair of sensors attached thereto according to an embodiment of the disclosure.

FIG. 66 shows a side view of implantable device 1102 with an inflow sensor 3500a and an outflow sensor 3500b attached thereto. Inflow sensor 3500a and outflow sensor 3500b may each be similar or identical to sensor 3300, with the exception that sensors 3500a and 3500b do not include Nitinol loops for attachment. Rather, inflow sensor 3500a includes coupling element 3510a and outflow sensor 3500b includes coupling element 3510b. Coupling elements 3510a and 3510b may each be thin, stiff pieces of material, such as wire, including Nitinol wires. It should be understood that coupling elements 3510a and 3510b need not be separate elements, but rather may form a single, integral member, such as a single elongated wire of Nitinol. Coupling elements 3510a and 3510b may be coupled to inflow sensor 3500a and outflow sensor 3500b by any suitable means, including adhesives or welding. Coupling elements 3510a and 3510b may be attached to implantable device 1102 via hollow tubing 1014a, 1014b in a similar manner, including adhesives or welding. Alternately, coupling elements 3510a and 3510b may be sutured to hollow tubing 1014a, 1014b, or to a covering, such as a fabric covering, that is provided over hollow tubing 1014a, 1014b. Coupling elements 3510a and 3510b are preferably coupled to hollow tubing 1014a, 1014b because of its relative rigidity and lack of motion during any adjustment of implantable device 1102. However, in some embodiments, coupling elements 3510a and 3510b may be coupled to other portions of implantable device 1102.

When implantable device 1102 is implanted in the native mitral valve annulus, for example, inflow sensor 3500a extends into the left atrium and outflow sensor 3500b extends through the native valve and into the left ventricle. As noted above, the coupling elements, particularly coupling element 3510b, is thin to minimize any interference with the coapting of the native mitral valve leaflets over coupling element 3510b. Preferably, coupling elements 3510a and 3510b are positioned on the internal circumference of implantable device 1102 and pass through the inside of implantable device 1102 to better align the sensors, and particularly outflow sensor 3500b, through the native mitral valve leaflets. However, in other embodiments, coupling elements 3510a and 3510b may be connected on the outer circumference of implantable device 1102. Further, outflow sensor 3500b could be attached directly to a structure of implantable device 1102, preferably so that it aligns with a valve and extends past a valve commissure so that it is positioned within the left ventricle. This may be accomplished by attaching outflow sensor 3500b at any point along the circumference of implantable device 1102 that aligns with a valve commissure. Also, rather than extending through the native valve leaflets, coupling element 3510b and outflow sensor 3500b could be passed through tissue of the annulus (or leaflet tissue near the annulus) to position outflow sensor 3500b in the left ventricle. This could be accomplished, for example, by using a needle to pierce the tissue and passing the outflow sensor 3500b through the tissue, or modifying the leading end of outflow sensor 3500b to be sharp enough to pierce the tissue. In one of these cases, the pierced tissue should be at a location that is likely to close around the piercing and still provide a seal, for example a portion of the tissue adjacent or in contact with cuff material of implantable device 1102.

Figure 67:
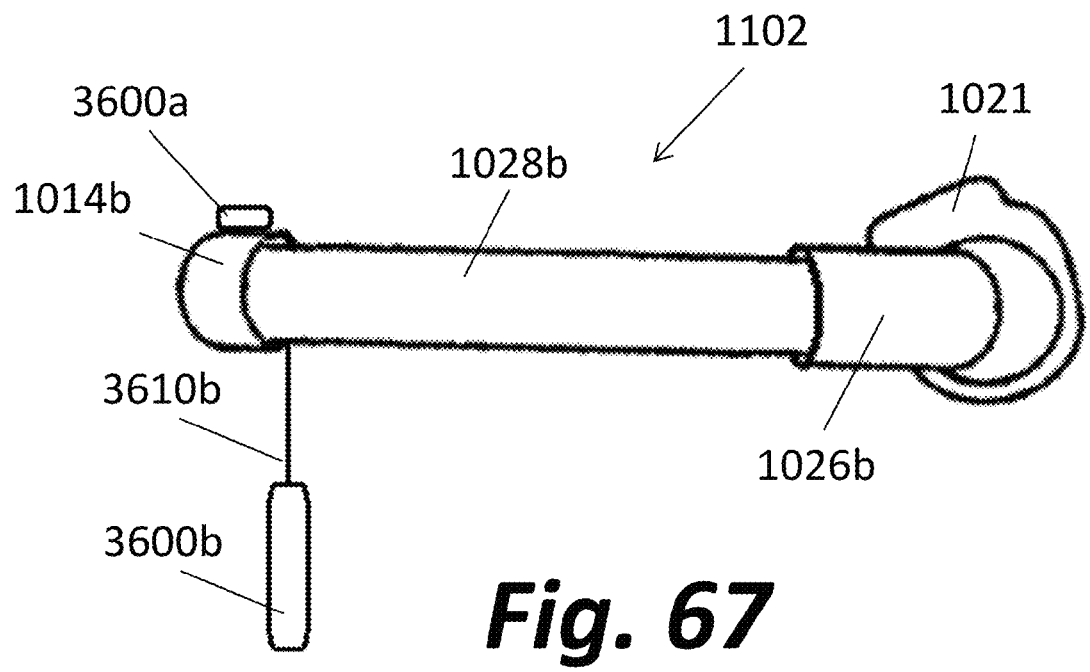
FIG. 67 is a side view of the implantable device of FIG. 31 with a pair of sensors attached thereto according to another embodiment of the disclosure.

In another embodiment, shown in FIG. 67, implantable device 1102 includes an inflow sensor 3600a coupled to the implantable device in a substantially similar manner as sensor 3400 is coupled to the implantable device in FIG. 65. Implantable device 1102 also includes an outflow sensor 3600b coupled to implantable device 1102 via coupling element 3610b in substantially the same way that outflow sensor 3500b is coupled to implantable device 1102 in FIG. 66. With the configuration shown, inflow sensor 3600a is exposed to blood in the left atrium when implantable device 1102 is implanted into the native mitral valve annulus, while coupling element 3610b extends through the native heart valve so that outflow sensor 3600b is positioned within the left ventricle.

Figure 68:
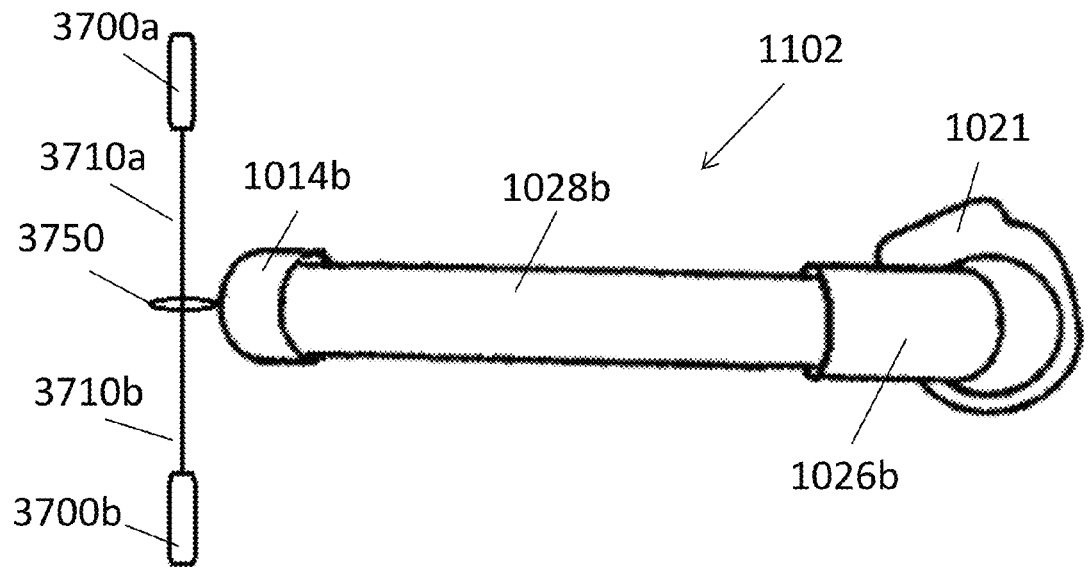
FIG. 68 is a side view of the implantable device of FIG. 31 with a pair of sensors attached to a securement feature of the implantable device.

FIG. 68 illustrates an embodiment with an inflow sensor 3700a and outflow sensor 3700b similar to those shown in FIG. 66. Sensors 3700a, 3700b and coupling elements 3710a, 3710b may be substantially similar or identical to those described in connection to FIG. 66. However, instead of coupling members 3710a and 3710b being coupled directly to hollow tubing 1014a, 1014b (or to a covering positioned on hollow tubing 1014a, 1014b), implantable device 1102 is provided with a securement feature 3750. Securement feature 3750 may take the form of a ring, as illustrated, or any other suitable form. Preferably, securement feature 3750 is a rigid member, such as a stiff Nitinol wire formed into a ring. Coupling elements 3710a and 3710b, whether formed separately or as an integral member, may pass through securement feature 3750 and be coupled thereto by any suitable means, including suture connections, adhesives, welding, or any other suitable mechanism. Although securement feature 3750 is shown extending from an outer circumferential portion of implantable device 1102, securement feature 3750 may alternately be coupled to and extend from an inner circumferential portion of implantable device 1102. In the illustrated configuration, when implantable device 1102 is implanted into a native mitral valve annulus, inflow sensor 3700a is positioned in the left atrium and outflow sensor 3700b is positioned in the left ventricle.

Figure 69:
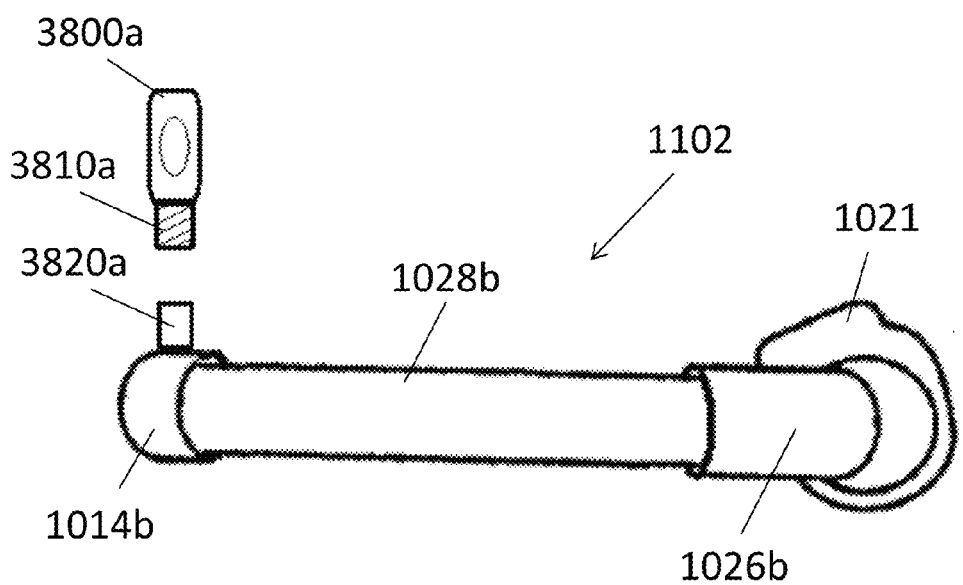
FIG. 69 is a side view of the implantable device of FIG. 31 with a sensor disassembled from the implantable device.

FIG. 69 illustrates an embodiment with an inflow sensor 3800a unassembled to implantable device 1102. Sensor 3800a may be substantially similar to sensor 3300 with certain exceptions. For example, instead of Nitinol loops, inflow sensor 3800a may include a connecting portion 3810a extending from an end of sensor 3800a. Connecting portion 3810a may be coupled to a body of sensor 3800a or may be formed integrally therewith. In the illustrated example, connecting portion 3810a is a substantially cylindrical threaded member. A docking member 3820a may be coupled to hollow tubing 1014a, 1014b, the docking member having a complementary shape to connecting portion 3810a and including an opening for receiving connecting portion 3810a. As illustrated, docking member 3820a is substantially cylindrical and is open on at least a first end, and may include complementary threading internally so that inflow sensor 3800a, via connecting portion 3810a, may be screwed into docking member 3820a. Docking member 3820a may be attached to hollow tubing 1014a, 1014b in any suitable fashion, including via suturing or welding. Alternatively, docking member 3820a may be formed integrally with hollow tubing 1014a, 1014b. In other embodiments, docking member 3820a may be connected to implantable device 1102 in other locations to provide a different location for securing inflow sensor 3800a to implantable device 1102. In some embodiments, a docking member similar or identical to docking member 3820a may be coupled to the outflow end of implantable device 1102 to provide a location for connecting an outflow sensor similar to sensor 3800a to implantable device 1102. Still further, although connecting portion 3810a is illustrated as a threaded cylindrical member, other structures may be suitable. For example, connecting portion 3810a and docking member 3820a may have any suitable complementary designs, such as male/female press-fit connecting members. With such a male/female design, inflow sensor 3800a may be coupled to implantable device 1102 quickly and securely after implantable device 1102 has been implanted in the patient, although inflow sensor 3800a may be connected to implantable device 1102 prior to or during implantation.

It should be understood that any inflow sensor design and/or connection mechanism illustrated or described in connection with FIGS. 65-69 may be used in combination with any outflow sensor design and/or connection mechanism illustrated or described in connection with FIGS. 65-69 so as to provide measurements of physiological data, such as blood pressure, on each side of the implantable device 1102. In addition, although inflow and outflow sensors are described and illustrated in relation to implantable device 1102 in FIGS. 65-69, it should be understood that other implantable devices described above, such as implantable devices 10, 100, 645, 700, 800, 1002, 1202, 1302, 1402, or 1502, may be employed with inflow and/or outflow sensors in similar or identical configurations to those described and illustrated in connection with implantable device 1102.

As noted above, there are many applications for sensors 3300 and modified versions of sensor 3300 described above. When utilized on adjustable annuloplasty rings implanted in the native mitral valve, one such application is the assessment of the severity of mitral regurgitation upon initial implantation of an annuloplasty ring to optimize the initial implantation, and then to continue to assess mitral regurgitation on an ongoing basis as time passes. If the implanted annuloplasty ring begins to lose effectiveness, for example if the native mitral valve leaflets fail to fully coapt, a user may learn of the issue in a timely manner by interpreting the data provided by the sensors on the annuloplasty ring. If the mitral regurgitation is determined to be significant enough, immediate intervention may be performed to correct the problem, for example by adjusting the size of the annuloplasty ring in a manner similar to that shown and described in connection with FIGS. 50-57, before the mitral regurgitation worsens and/or causes additional health problems.

Although adjustable annuloplasty rings are generally described above for use in the mitral valve annulus, annuloplasty rings may be used in a similar manner for other heart valves, such as the aortic valve. In these embodiments, sensors used with the adjustable aortic annuloplasty ring may be used to measure physiological data across the aortic valve, such as pressure drop, which may be indicative of aortic regurgitation. One measure of regurgitation in aortic heart valves is the aortic regurgitation index, which may be defined as the ratio of the transvalvular gradient between the diastolic blood pressure (RRdia) in the aorta and the left-ventricular end-diastolic blood pressure (LVEDP) to the systolic blood pressure (RRsys) in the aorta: $[(RRdia-LVEDP)/RRsys] \times 100$. The aortic regurgitation index has an inverse correlation to the severity of aortic regurgitation and allows a physician to differentiate between patients with mild, moderate, or severe aortic regurgitation. The aortic regurgitation index may also be independently used to predict the associated 1-year mortality risk for a given patient upon collection of data.

Figure 74:
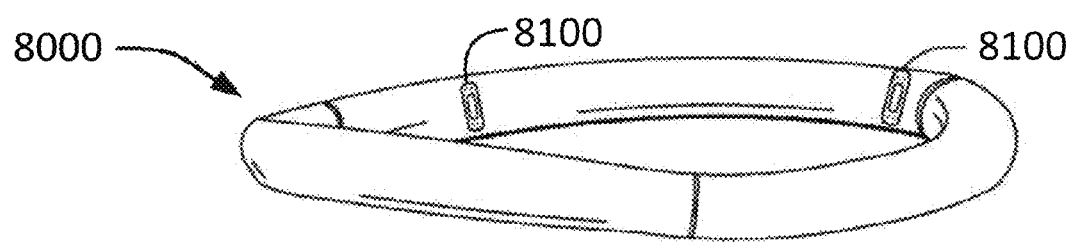
FIG. 74 is a perspective view of a non-adjustable annuloplasty ring with sensors attached thereto according to an embodiment of the disclosure.

Although described generally in terms of adjustable annuloplasty rings, the sensors described herein may be similarly attached to non-adjustable annuloplasty rings to track relevant patient data in a similar fashion. For example, inflow and/or outflow sensors may be coupled to a non-adjustable annuloplasty ring in a similar fashion as shown in any of FIGS. 65-69. One embodiment of a non-adjustable annuloplasty ring 8000 is illustrated in FIG. 74, with one or more sensors 8100 attached thereto. Generally, inflow and outflow sensors would be used with a non-adjustable annuloplasty ring in the same manner and with the same effects as described herein for adjustable annuloplasty rings, with at least one exception. Because non-adjustable annuloplasty rings generally do not change sizes, sensors may be coupled to a non-adjustable annuloplasty ring at any suitable location without consideration of how moving or adjustable parts of the annuloplasty ring may interfere with the attachments of the sensors thereto.

Figure 70:
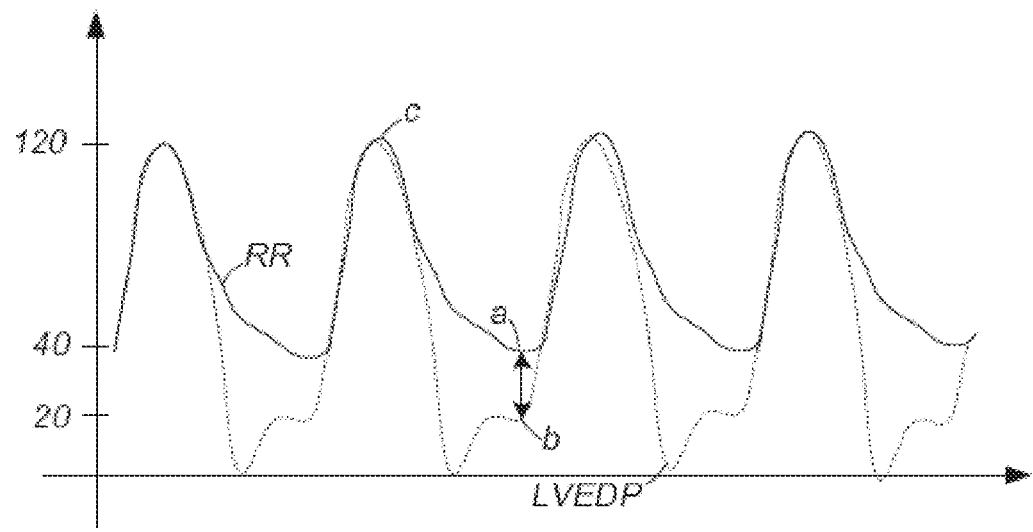
FIGS. 70 and 71 are graphs showing examples of hemodynamic assessments during a valve annuloplasty procedure.

FIG. 70 illustrates the aortic regurgitation index in a patient with moderate aortic regurgitation. As seen in the graph, the patient has an aortic diastolic blood pressure (RRdia) of 40, a left-ventricular end-diastolic blood pressure (LVEDP) of 20, and an aortic systolic blood pressure (RRsys) of 120. Using the formula for the aortic regurgitation index defined above yields the following:

$$(RR\text{dia}-LVEDP)/RR\text{sys} \times 100 = (a-b)/c \times 100 = (40-20)/120 \times 100 = 16.7$$

Figure 71:
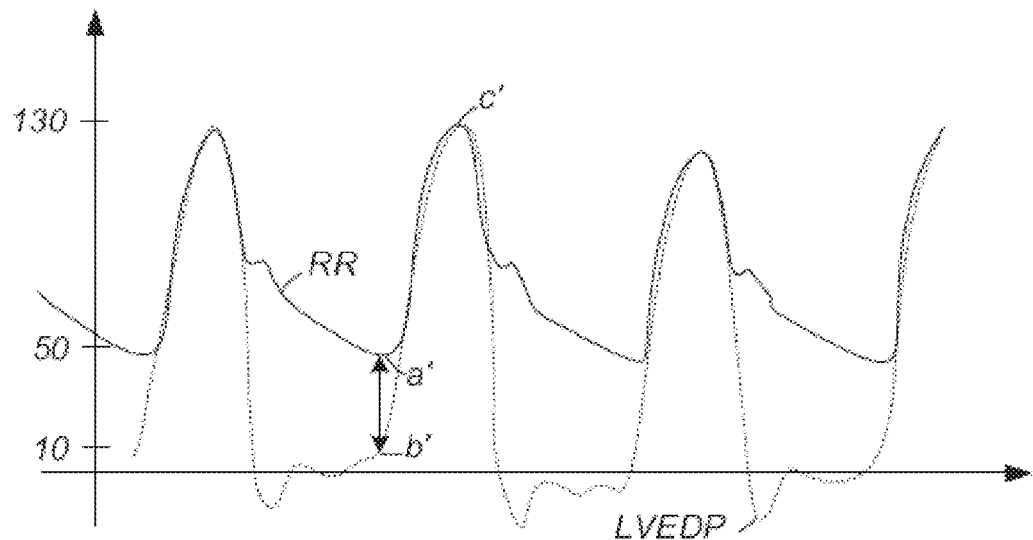

For a second patient, the aortic regurgitation index indicates a trivial amount of aortic regurgitation as shown in FIG. 71. For this patient, the aortic diastolic blood pressure (RRdia) is 50, the left-ventricular end-diastolic blood pressure (LVEDP) is 10 and the aortic systolic blood pressure is 130, yielding an aortic regurgitation index as calculated below:

$$(RR\text{dia}-LVEDP)/RR\text{sys} \times 100 = (a'-b')/c' \times 100 = (50-10)/130 \times 100 = 30.8$$

When used in conjunction with annuloplasty rings, sensors 3300 and the variations described above may measure blood pressure to determine an aortic regurgitation index and thus reveal the severity of the regurgitation. As described above, the measurements may be taken initially prior to completion of the original implantation to determine if the annuloplasty ring should be adjusted before completing the surgery, and then measurements may be taken on a continuing basis to determine if the annuloplasty ring is losing effectiveness. Based on the calculated aortic regurgitation index, follow-up treatment may be advised, such as a re-adjustment of the annuloplasty ring.

Figure 72:
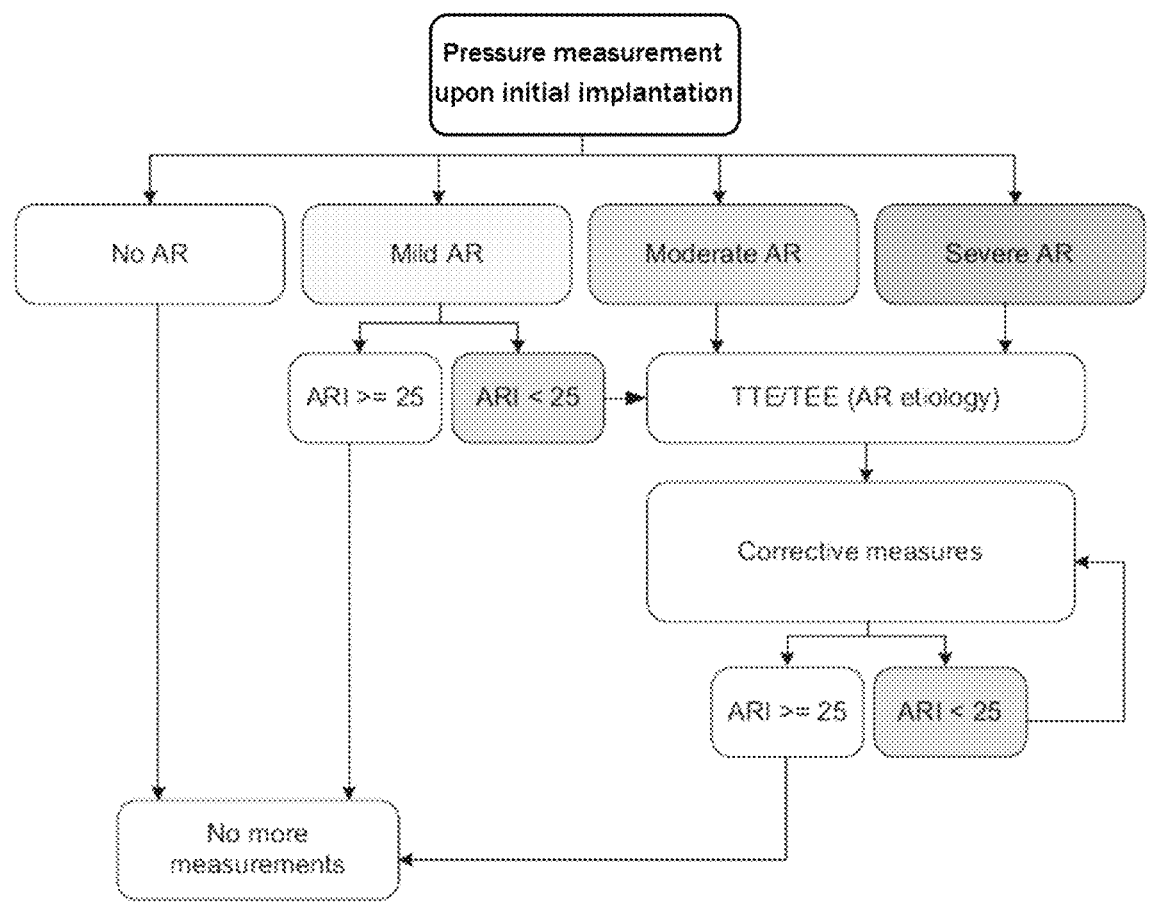
FIG. 72 is a flow chart showing one possible method of using a prosthetic heart device with sensors attached thereto.

One example of a method using an adjustable annuloplasty ring having sensors is shown in FIG. 72. In this method, with the annuloplasty ring implanted into the native aortic valve annulus and the incision closed with a purse-string suture over an adjustment tool still coupled to the annuloplasty ring, the heart is re-started and the pressure drop across the aortic valve annulus is measured using inflow and outflow sensors coupled to the annuloplasty ring. A preliminary assessment of aortic regurgitation is made and may provide a rough classification of the regurgitation into four groups: no aortic regurgitation, mild aortic regurgitation, moderate aortic regurgitation, and severe aortic regurgitation. If the preliminary technique shows no aortic regurgitation, the adjustment tool may be decoupled from the annuloplasty ring and the incision fully closed, with no more preliminary measurements being taken. In this case, the procedure may be considered successful. If the preliminary technique shows that mild aortic regurgitation is present, then the sensors may be used to quantify the amount of aortic regurgitation by making measurements used to calculate an aortic regurgitation index (ARI), as described above. An aortic regurgitation index greater than or equal to 25 may indicate that the aortic regurgitation is negligible, which may result in decoupling the adjustment tool and fully closing the incision. If, however, the index is less than 25, then the aortic regurgitation may be classified as either moderate or severe. In either case, further diagnostic techniques, such as, for example, transesophageal echocardiography (TEE) or transthoracic echocardiography (TTE), may be performed to further assess the situation, followed by a corrective measure. The corrective measure may include decreasing the size of the annuloplasty ring with the adjustment tool which is still coupled to the annuloplasty ring. Following the corrective measure, the sensors may be used to recalculate the aortic regurgitation index. If the aortic regurgitation index is greater than or equal to 25, then the corrective measure may be considered successful, the adjustment tool decoupled from the annuloplasty ring, and the incision fully closed. If, however, the aortic regurgitation index remains below 25, then the size of the annuloplasty ring may be adjusted again. This loop from corrective measure to aortic regurgitation index calculation may continue until it is determined that the annuloplasty ring is providing adequate function. It should be understood that, even after the implantation is complete, the same or similar procedure described above may be continued on an ongoing and/or periodic schedule to assess the effectiveness of the annuloplasty ring in the days, weeks, months, and years following implantation. If the aortic regurgitation index is calculated to be an undesirable level at any point after implantation, another procedure may be performed on the patient to re-adjust the annuloplasty ring until the aortic regurgitation is eliminated or otherwise sufficiently mitigated. Such a procedure may be accomplished, for example, using adjustment tools 2006 or 2050 and related methods described in connection with FIGS. 50-60.

When implanting a non-adjustable annuloplasty ring with sensors attached thereto, the procedure may be similar to that described directly above in relation to an adjustable annuloplasty ring. However, because non-adjustable annuloplasty rings generally do not change in size, the sensors may be used to first confirm function upon the initial implantation procedure, and then to continue monitoring effectiveness of the non-adjustable annuloplasty ring and/or the health of the patient on an ongoing basis.

Figure 73:
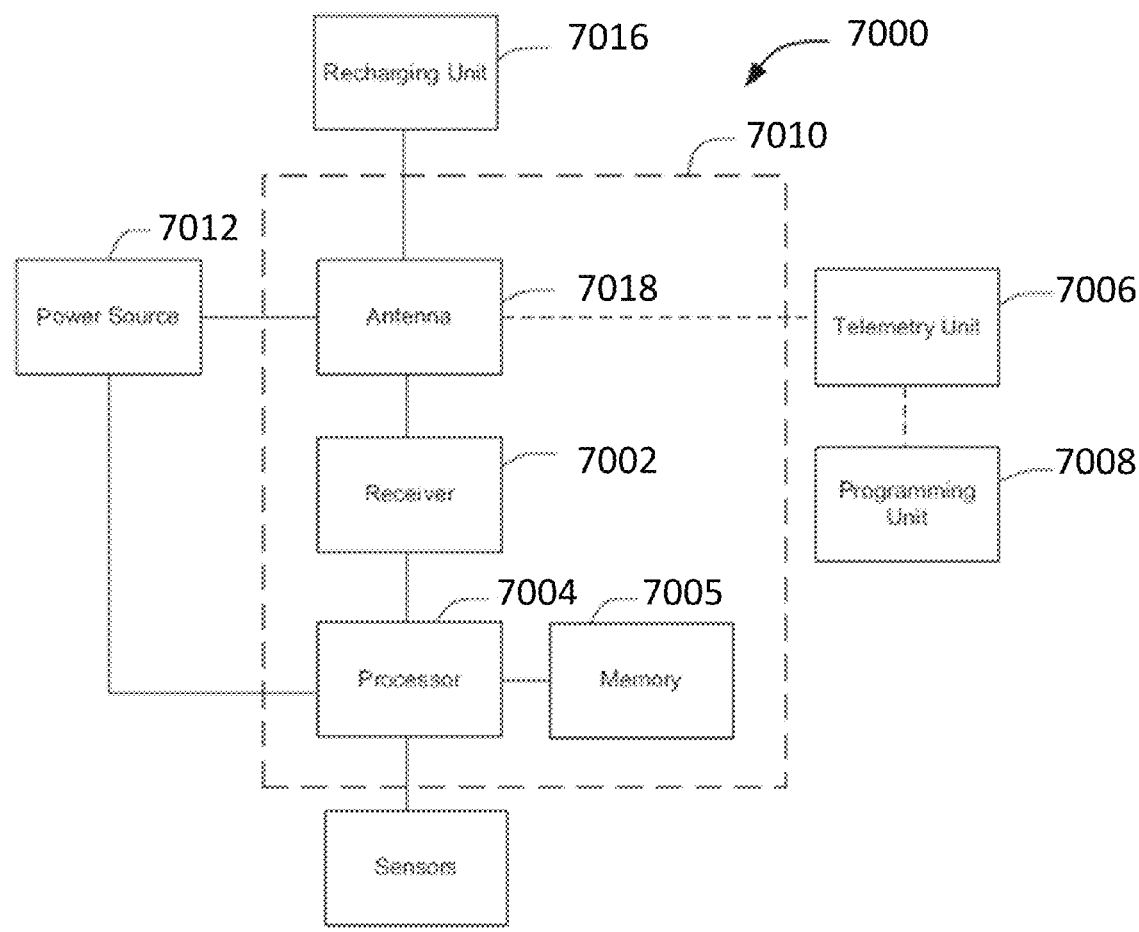
FIG. 73 is a schematic representation of a system for valve evaluation using the sensors of the present disclosure.

FIG. 73 is a schematic overview of one embodiment of the components of a valve diagnostic system 7000 including an electronic subassembly 7010 disposed within a control module. It will be understood that the valve diagnostic system can include more, fewer, or different components and can have a variety of different configurations.

Some of the components (for example, power source 7012, antenna 7018, receiver 7002, and processor 7004) of valve diagnostic system 7000 can be positioned on one or more circuit boards or similar carriers. Any power source 7012 can be used including, for example, a battery, such as a primary battery or a rechargeable battery. Examples of other power sources include super capacitors, nuclear or atomic batteries, mechanical resonators, infrared collectors, thermally powered energy sources, flexural powered energy sources, bioenergy power sources, fuel cells, bioelectric cells, osmotic pressure pumps, and the like.

If the power source 7012 is a rechargeable battery, the battery may be recharged using the optional antenna 7018, if desired. Power can be provided to the battery for recharging by inductively coupling the battery through the antenna to a recharging unit 7016 external to the user.

A processor 7004 is included to obtain data from the sensors relating to force, pressure or elasticity measured by each of the sensors. Any processor can be used and can be as simple as an electronic device that, for example, is capable of receiving and interpreting instructions from an external programming unit 7008 and performing calculations based on the various algorithms described above. A memory 7005 may include data in the form of a dataset for performing various steps of the algorithm. In some examples, data from the sensors relating to pressure, forces and the like may be passed to processor 7004 and compared against a dataset stored in memory 7005 to determine if further treatment and/or diagnosis is necessary. Additionally, data relating to valve diagnosis may be sent from programming unit 7008 to processor 7004 and the processor may determine the appropriate course of action or send an alert to a clinician. Communication between programming unit 7008 and processor 7004 may be accomplished via communication between antenna 7018 and telemetry unit 7006. Additionally, sensors may be in communication with one or more wearable devices to enable the user to continuously monitor or track the functionality of a therapeutic device. Such wearable devices may track or log data, and if necessary, provide the data to a clinician or alert emergency personnel if immediate attention is needed.

According to one embodiment of the disclosure, an implantable device system comprises:

an implantable device for controlling at least one of a shape and a size of a heart valve annulus, the implantable device including:
 an arcuate body; and
 a sensor system configured to be coupled to the implantable device, the sensor system including:

a first sensor configured to measure physiological data when the implantable device is implanted into the valve annulus; and/or a second sensor configured to measure physiological data when the implantable device is implanted into the valve annulus, the first sensor configured to measure data at an inflow portion of the valve annulus and the second sensor configured to measure data at an outflow portion of the valve annulus; and/or an adjustment system configured to adjust at least one of a shape and a size of the arcuate body; and/or an adjustment tool configured to be coupled to the adjustment system so that the adjustment tool can be used to activate and control adjustment of the arcuate body; and/or the arcuate body includes a first body portion configured to slide with respect to a second body portion upon adjustment of the arcuate body; and/or the first body portion is positioned at least partially within the second body portion; and/or the second body portion is more rigid than the first body portion; and/or the first sensor is directly coupled to the second body portion; and/or the first sensor is coupled to the second body portion by an adhesive; and/or the first sensor includes a body with a plurality of apertures extending therethrough, the first sensor being sutured to the second body portion; and/or the first sensor includes a first coupling element extending therefrom and the second sensor includes a second coupling element extending therefrom, at least one of the first and second coupling elements being configured to attach to the implantable device; and/or the first and second coupling elements are wires; and/or the first coupling element is integral with the second coupling element; and/or the arcuate body is at least partially covered by a fabric suitable for attachment to at least one of the first and second coupling elements; and/or a wire ring coupled the arcuate body and configured to attach to at least one of the first and second coupling elements; and/or the wire ring is positioned on an outer diameter of the arcuate body; and/or the wire ring is positioned on an inner diameter of the arcuate body; and/or the first sensor includes a first docking member extending therefrom and the arcuate body includes a second docking member configured to mate with the first docking member, the second docking member extending into an inflow portion of the valve annulus when the implantable device is implanted into the valve annulus; and/or the first and second docking members include complementary threads; and/or the first docking member has one of a male and a female press-fit connection mechanism and the second docking member has the other of the male and the female press-fit connection mechanism; and/or the adjustment system includes a flexible element and an adjustment mechanism operable to adjust a length of the flexible element.

According to another embodiment of the disclosure, a method of performing a first surgical procedure in a patient comprises:

forming an incision in a heart of the patient;

implanting a device into a heart valve annulus of the patient, the device configured to control at least one of a shape and size of the heart valve annulus and including an arcuate body;

coupling a sensor system to the device, the sensor system including a first sensor;

measuring a first set of physiological data using the sensor system; and/or determining from the first set of physiological data a first amount of regurgitation across the heart valve annulus; and/or the sensor system further includes a second sensor, the first sensor being positioned in an inflow portion of the heart valve annulus and the second sensor being positioned in an outflow portion of the heart valve annulus, the first set of physiological data being measured across the heart valve annulus; and/or coupling an adjustment tool to an adjustment system of the device, the adjust system configured to adjust at least one of a shape and size of the arcuate body; and at least partially closing the incision over a portion of the adjustment tool while the adjustment tool is coupled to the adjustment system; and/or using the adjustment tool to adjust at least one of the shape and the size of the arcuate body if the determined first amount of regurgitation across the heart valve annulus is greater than or equal to a predetermined value; and/or measuring a second set of physiological data across the heart valve annulus using the sensor system after adjusting the arcuate body; and determining from the second set of physiological data a second amount of regurgitation across the heart valve annulus; and/or uncoupling the adjustment tool from the adjustment system if the second amount of regurgitation across the heart valve annulus is less than the predetermined value; and fully closing the incision after uncoupling the adjustment tool from the adjustment system; and/or at least periodically measuring additional sets of physiological data across the heart valve annulus using the sensor system after fully closing the incision; and determining from the additional sets of physiological data additional amounts of regurgitation across the heart valve annulus; and/or performing a second surgical procedure in the patient if one of the additional amounts of regurgitation across the heart valve annulus is greater than or equal to the predetermined value, the second surgical procedure including adjusting at least one of the shape and the size of the arcuate body; and/or uncoupling the adjustment tool from the adjustment system if the first amount of regurgitation across the heart valve annulus is less than a predetermined value; and fully closing the incision after uncoupling the adjustment tool from the adjustment system; and/or at least periodically measuring additional sets of physiological data across the heart valve annulus using the sensor system after fully closing the incision; and determining from the additional sets of physiological data additional amounts of regurgitation across the heart valve annulus; and/or performing a second surgical procedure in the patient if one of the additional amounts of regurgitation across the heart valve annulus is greater than or equal to the predetermined value, the second surgical procedure including adjusting at least one of the shape and the size of the arcuate body.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, features described in connection with one embodiment may be combined with features described in connection with other embodiments.

The invention claimed is:

1. An implantable device system comprising:
an implantable device for controlling at least one of a shape and a size of a heart valve annulus, the implantable device including:
an arcuate body; and
a sensor system configured to be coupled to the implantable device, the sensor system including:
a first sensor configured to measure physiological data when the implantable device is implanted into the valve annulus; and
a second sensor configured to measure physiological data when the implantable device is implanted into the valve annulus, the first sensor configured to measure data at an inflow portion of the valve annulus and the second sensor configured to measure data at an outflow portion of the valve annulus;
wherein the first sensor includes a first coupling element extending therefrom and the second sensor includes a second coupling element extending therefrom, at least one of the first and second coupling elements being configured to attach to the implantable device,
wherein a wire ring is coupled to the arcuate body and configured to attach to at least one of the first and second coupling elements.

2. The implantable device system of claim 1, wherein the implantable device includes an adjustment system configured to adjust at least one of a shape and a size of the arcuate body, and the adjustment system includes an adjustment tool configured to be coupled to the adjustment system so that the adjustment tool can be used to activate and control adjustment of the arcuate body.

3. The implantable device system of claim 2, wherein the arcuate body includes a first body portion configured to slide with respect to a second body portion upon adjustment of the arcuate body.

4. The implantable device system of claim 3, wherein the first body portion is positioned at least partially within the second body portion.

5. The implantable device system of claim 4, wherein the second body portion is more rigid than the first body portion.

6. The implantable device system of claim 2, wherein the adjustment system includes a flexible element and an adjustment mechanism operable to adjust a shape of the flexible element.

7. The implantable device system of claim 1, wherein the first and second coupling elements are wires.

8. The implantable device system of claim 7, wherein the first coupling element is integral with the second coupling element.

9. The implantable device system of claim 1, wherein the arcuate body is at least partially covered by a fabric suitable for attachment to at least one of the first and second coupling elements.

10. The implantable device system of claim 1, wherein the wire ring is positioned on an outer diameter of the arcuate body.

11. The implantable device system of claim 1, wherein the wire ring is positioned on an inner diameter of the arcuate body.

12. An implantable device system comprising:
an implantable device for controlling at least one of a shape and a size of a heart valve annulus, the implantable device including:
an arcuate body; and
a sensor system configured to be coupled to the implantable device, the sensor system including:
a first sensor configured to measure physiological data when the implantable device is implanted into the valve annulus,
wherein the first sensor includes a first docking member extending therefrom and the arcuate body includes a second docking member configured to mate with the first docking member, the second docking member extending into an inflow portion of the valve annulus when the implantable device is implanted into the valve annulus,
wherein the first and second docking members include complementary threads.

13. An implantable device system comprising:
an implantable device for controlling at least one of a shape and a size of a heart valve annulus, the implantable device including:
an arcuate body; and
a sensor system configured to be coupled to the implantable device, the sensor system including:
a first sensor configured to measure physiological data when the implantable device is implanted into the valve annulus,
wherein the first sensor includes a first docking member extending therefrom and the arcuate body includes a second docking member configured to mate with the first docking member, the second docking member extending into an inflow portion of the valve annulus when the implantable device is implanted into the valve annulus,
wherein the first docking member has one of a male and a female press-fit connection mechanism and the second docking member has the other of the male and the female press-fit connection mechanism.

* * * * *